US009481885B2

(12) United States Patent
Croce et al.

(10) Patent No.: US 9,481,885 B2
(45) Date of Patent: Nov. 1, 2016

(54) METHODS AND COMPOSITIONS RELATED TO MIR-21 AND MIR-29A, EXOSOME INHIBITION, AND CANCER METASTASIS

(71) Applicant: Ohio State Innovation Foundation, Columbus, OH (US)

(72) Inventors: Carlo M. Croce, Columbus, OH (US); Muller Fabbri, Los Angeles, CA (US)

(73) Assignee: Ohio State Innovation Foundation, Columbus, OH (US)

( * ) Notice: Subject to any disclaimer, the term of this patent is extended or adjusted under 35 U.S.C. 154(b) by 24 days.

(21) Appl. No.: 14/364,159

(22) PCT Filed: Dec. 13, 2012

(86) PCT No.: PCT/US2012/069484
§ 371 (c)(1),
(2) Date: Jun. 10, 2014

(87) PCT Pub. No.: WO2013/090556
PCT Pub. Date: Jun. 20, 2013

(65) Prior Publication Data
US 2014/0323553 A1    Oct. 30, 2014

Related U.S. Application Data

(60) Provisional application No. 61/569,862, filed on Dec. 13, 2011, provisional application No. 61/644,980, filed on May 9, 2012.

(51) Int. Cl.
| A61K 48/00 | (2006.01) |
| C12N 15/113 | (2010.01) |
| A61K 31/7125 | (2006.01) |
| A61K 45/06 | (2006.01) |
| C12Q 1/68 | (2006.01) |

(52) U.S. Cl.
CPC ......... *C12N 15/113* (2013.01); *A61K 31/7125* (2013.01); *A61K 45/06* (2013.01); *A61K 48/00* (2013.01); *C12Q 1/6886* (2013.01); *C12N 2310/113* (2013.01); *C12N 2310/3231* (2013.01); *C12N 2320/31* (2013.01); *C12Q 2600/118* (2013.01)

(58) Field of Classification Search
None
See application file for complete search history.

(56) References Cited

U.S. PATENT DOCUMENTS

| 4,172,124 A | 10/1979 | Koprowski et al. |
| 4,196,265 A | 4/1980 | Koprowski et al. |
| 4,608,337 A | 8/1986 | Croce |
| 4,693,975 A | 9/1987 | Kozbor et al. |
| 4,701,409 A | 10/1987 | Croce |
| 5,015,568 A | 5/1991 | Tsujimoto et al. |
| 5,149,628 A | 9/1992 | Croce |
| 5,198,338 A | 3/1993 | Croce |
| 5,202,429 A | 4/1993 | Tsujimoto et al. |
| 5,459,251 A | 10/1995 | Tsujimoto et al. |
| 5,506,106 A | 4/1996 | Croce et al. |
| 5,506,344 A | 4/1996 | Tsujimoto et al. |
| 5,523,393 A | 6/1996 | Tsujimoto et al. |
| 5,567,586 A | 10/1996 | Croce |
| 5,595,869 A | 1/1997 | Tsujimoto et al. |
| 5,633,135 A | 5/1997 | Croce et al. |
| 5,633,136 A | 5/1997 | Croce et al. |
| 5,674,682 A | 10/1997 | Croce et al. |
| 5,688,649 A | 11/1997 | Croce et al. |
| 5,695,944 A | 12/1997 | Croce et al. |
| 5,928,884 A | 7/1999 | Croce et al. |
| 5,939,258 A | 8/1999 | Croce et al. |
| 5,985,598 A | 11/1999 | Russo et al. |
| 6,040,140 A | 3/2000 | Croce et al. |
| 6,130,201 A | 10/2000 | Croce et al. |
| 6,187,536 B1 | 2/2001 | Weinberg et al. |
| 6,242,212 B1 | 6/2001 | Croce et al. |
| 6,255,293 B1 | 7/2001 | Kimchi |
| 6,258,541 B1 | 7/2001 | Chapkin et al. |
| 6,649,396 B1 | 11/2003 | Curiel et al. |
| 6,774,217 B1 | 8/2004 | Croce et al. |
| 6,924,414 B2 | 8/2005 | Croce et al. |
| 7,060,811 B2 | 6/2006 | Aldaz et al. |
| 7,141,417 B1 | 11/2006 | Croce et al. |

(Continued)

FOREIGN PATENT DOCUMENTS

| AU | 2007/243475 B2 | 5/2013 |
| CA | 2533701 A1 | 2/2005 |

(Continued)

OTHER PUBLICATIONS

Australian Examination Report No. 1, Application No. 2008262252 dated Feb. 15, 2013.

(Continued)

*Primary Examiner* — Kimberly Chong
(74) *Attorney, Agent, or Firm* — MacMillan, Sobanski & Todd, LLC

(57) ABSTRACT

The present invention provides materials and methods related to the discovery that tumor secreted miR-21 and miR-29a can function by binding as ligands to receptors of the Tolllike receptor family, murine TLR7 and human TLR8, in immune cells, triggering a TLR-mediated prometastatic inflammatory response, which leads to tumor growth and metastasis. Thus, by acting as paracrine agonists of TLRs, secreted miRNAs are key regulators of the tumor microenvironment. This mechanism of action of miRNAs is important in the tumor-immune system communication, in tumor growth and spread, and in cancer treatment.

20 Claims, 28 Drawing Sheets
(14 of 28 Drawing Sheet(s) Filed in Color)

(56) References Cited

U.S. PATENT DOCUMENTS

| | | |
|---|---|---|
| 7,175,995 B1 | 2/2007 | Russo et al. |
| 7,217,568 B2 | 5/2007 | Jamieson et al. |
| 7,220,834 B2 | 5/2007 | Croce et al. |
| 7,232,806 B2 | 6/2007 | Tuschl et al. |
| 7,390,792 B2 | 6/2008 | Srivastava et al. |
| 7,455,995 B2 | 11/2008 | Tanner et al. |
| 7,585,969 B2 | 9/2009 | Stoffel et al. |
| 7,592,441 B2 | 9/2009 | Bentwich et al. |
| 7,618,814 B2 | 11/2009 | Bentwich et al. |
| 7,642,348 B2 | 1/2010 | Bentwich et al. |
| 7,667,090 B2 | 2/2010 | Croce |
| 7,670,840 B2 | 3/2010 | Croce et al. |
| 7,709,616 B2 | 5/2010 | Bentwich et al. |
| 7,723,030 B2 | 5/2010 | Croce et al. |
| 7,723,035 B2 | 5/2010 | Croce et al. |
| 7,728,189 B2 | 6/2010 | Croce |
| 7,749,715 B2 | 7/2010 | Russo et al. |
| 7,777,005 B2 | 8/2010 | Croce et al. |
| 7,811,759 B2 | 10/2010 | Han |
| 7,888,010 B2 | 2/2011 | Brown et al. |
| 7,919,245 B2 | 4/2011 | Brown et al. |
| 8,084,199 B2 | 12/2011 | Croce et al. |
| 8,361,710 B2 | 1/2013 | Croce et al. |
| 8,691,232 B2 | 4/2014 | Derynck et al. |
| 8,709,732 B2 | 4/2014 | Lo et al. |
| 8,728,745 B2 | 5/2014 | Martin et al. |
| 2001/0026796 A1 | 10/2001 | Croce et al. |
| 2002/0086331 A1 | 7/2002 | Croce et al. |
| 2002/0116726 A1 | 8/2002 | Croce et al. |
| 2002/0132290 A1 | 9/2002 | Frazer |
| 2003/0143646 A1 | 7/2003 | Laskey et al. |
| 2003/0206958 A1 | 11/2003 | Cattaneo et al. |
| 2004/0033502 A1 | 2/2004 | Williams et al. |
| 2004/0078834 A1 | 4/2004 | Croce |
| 2004/0152112 A1 | 8/2004 | Croce et al. |
| 2004/0265316 A1 | 12/2004 | Croce et al. |
| 2004/0265930 A1 | 12/2004 | Sun et al. |
| 2005/0013247 A1 | 1/2005 | Sipola et al. |
| 2005/0019890 A1 | 1/2005 | Croce |
| 2005/0059005 A1 | 3/2005 | Tuschl et al. |
| 2005/0069918 A1 | 3/2005 | Claret |
| 2005/0074797 A1 | 4/2005 | Croce et al. |
| 2005/0075492 A1 | 4/2005 | Chen et al. |
| 2005/0112630 A1 | 5/2005 | Shaughnessy et al. |
| 2005/0164252 A1 | 7/2005 | Yeung |
| 2005/0176025 A1 | 8/2005 | McSwiggen et al. |
| 2005/0181385 A1 | 8/2005 | Linsley et al. |
| 2005/0186589 A1 | 8/2005 | Kowalik et al. |
| 2005/0256072 A1 | 11/2005 | Aronin et al. |
| 2005/0260639 A1 | 11/2005 | Nakamura et al. |
| 2005/0266443 A1 | 12/2005 | Croce et al. |
| 2005/0287530 A1 | 12/2005 | Croce et al. |
| 2006/0019286 A1 | 1/2006 | Horvitz et al. |
| 2006/0024780 A1 | 2/2006 | Aldaz et al. |
| 2006/0037088 A1 | 2/2006 | Li |
| 2006/0075511 A1 | 4/2006 | Croce et al. |
| 2006/0084059 A1 | 4/2006 | Yip et al. |
| 2006/0099619 A1 | 5/2006 | Remacle et al. |
| 2006/0105340 A1 | 5/2006 | Croce et al. |
| 2006/0105360 A1 | 5/2006 | Croce et al. |
| 2006/0116321 A1 | 6/2006 | Robbins et al. |
| 2006/0121085 A1 | 6/2006 | Warren et al. |
| 2006/0127895 A1 | 6/2006 | Sabapathy |
| 2006/0134639 A1 | 6/2006 | Huffel et al. |
| 2006/0165659 A1 | 7/2006 | Croce et al. |
| 2006/0166918 A1 | 7/2006 | Heidenreich et al. |
| 2006/0185027 A1 | 8/2006 | Bartel et al. |
| 2006/0188924 A1 | 8/2006 | Russo et al. |
| 2006/0188959 A1 | 8/2006 | Croce et al. |
| 2006/0189557 A1 | 8/2006 | Slack et al. |
| 2006/0199233 A1 | 9/2006 | Dahlberg et al. |
| 2006/0247448 A1 | 11/2006 | Boivin et al. |
| 2006/0292616 A1 | 12/2006 | Neely et al. |
| 2007/0015841 A1 | 1/2007 | Tawa et al. |
| 2007/0036765 A1 | 2/2007 | Civin et al. |
| 2007/0050146 A1 | 3/2007 | Bentwich et al. |
| 2007/0054849 A1 | 3/2007 | Nakamura et al. |
| 2007/0065840 A1 | 3/2007 | Naguibneva et al. |
| 2007/0065844 A1 | 3/2007 | Golub et al. |
| 2007/0072230 A1 | 3/2007 | Croce et al. |
| 2007/0092882 A1 | 4/2007 | Wang et al. |
| 2007/0099196 A1 | 5/2007 | Kauppinen et al. |
| 2007/0123482 A1 | 5/2007 | Stoffel et al. |
| 2007/0161004 A1 | 7/2007 | Brown et al. |
| 2007/0178105 A1 | 8/2007 | Croce et al. |
| 2007/0178502 A1 | 8/2007 | Reed |
| 2007/0212727 A1 | 9/2007 | Szalay et al. |
| 2007/0213292 A1 | 9/2007 | Stoffel et al. |
| 2007/0259352 A1 | 11/2007 | Bentwich et al. |
| 2007/0292878 A1 | 12/2007 | Raymond |
| 2008/0026951 A1 | 1/2008 | Brown et al. |
| 2008/0050744 A1* | 2/2008 | Brown ............... C12N 15/111 435/6.14 |
| 2008/0171667 A1 | 7/2008 | Brown et al. |
| 2008/0176766 A1 | 7/2008 | Brown et al. |
| 2008/0182245 A1 | 7/2008 | Brown et al. |
| 2008/0193943 A1 | 8/2008 | Murray |
| 2008/0254473 A1 | 10/2008 | Chen et al. |
| 2008/0256650 A1 | 10/2008 | Croce |
| 2008/0261908 A1 | 10/2008 | Croce et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0005336 A1 | 1/2009 | Wang |
| 2009/0023149 A1 | 1/2009 | Knudsen |
| 2009/0023594 A1 | 1/2009 | Mouritzen et al. |
| 2009/0029932 A1 | 1/2009 | Voinnet et al. |
| 2009/0061424 A1 | 3/2009 | Chen |
| 2009/0092974 A1 | 4/2009 | Davison et al. |
| 2009/0099034 A1 | 4/2009 | Ahlquist et al. |
| 2009/0123533 A1 | 5/2009 | Croce et al. |
| 2009/0123912 A1 | 5/2009 | Raymond |
| 2009/0123933 A1 | 5/2009 | Mishra |
| 2009/0131348 A1 | 5/2009 | Labourier et al. |
| 2009/0131354 A1 | 5/2009 | Bader et al. |
| 2009/0131356 A1 | 5/2009 | Bader et al. |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1 | 7/2009 | Brown et al. |
| 2009/0192102 A1 | 7/2009 | Bader et al. |
| 2009/0192111 A1 | 7/2009 | Bader et al. |
| 2009/0192114 A1 | 7/2009 | Ovcharenko et al. |
| 2009/0209450 A1 | 8/2009 | Croce et al. |
| 2009/0220589 A1 | 9/2009 | Trieu et al. |
| 2009/0222934 A1 | 9/2009 | Croce |
| 2009/0227533 A1 | 9/2009 | Bader et al. |
| 2009/0232893 A1 | 9/2009 | Bader et al. |
| 2009/0233297 A1 | 9/2009 | Mambo et al. |
| 2009/0239818 A1 | 9/2009 | Cheng |
| 2009/0253780 A1 | 10/2009 | Takeshita et al. |
| 2009/0263803 A1 | 10/2009 | Beaudenon et al. |
| 2009/0270484 A1 | 10/2009 | Croce et al. |
| 2009/0281167 A1 | 11/2009 | Shen et al. |
| 2009/0306194 A1 | 12/2009 | Ford et al. |
| 2010/0004320 A1* | 1/2010 | Elmen ............... C12N 15/113 514/44 R |
| 2010/0004322 A1 | 1/2010 | Croce |
| 2010/0021734 A1 | 1/2010 | Uemoto et al. |
| 2010/0048681 A1 | 2/2010 | Croce |
| 2010/0099200 A1 | 4/2010 | Nazabal et al. |
| 2010/0104662 A1 | 4/2010 | Oren et al. |
| 2010/0120898 A1 | 5/2010 | Croce et al. |
| 2010/0137410 A1 | 6/2010 | Croce |
| 2010/0144850 A1 | 6/2010 | Croce |
| 2010/0151480 A1 | 6/2010 | Taylor et al. |
| 2010/0173319 A1 | 7/2010 | Croce et al. |
| 2010/0179213 A1 | 7/2010 | Patrawala et al. |
| 2010/0184032 A1 | 7/2010 | Georgantas et al. |
| 2010/0184830 A1 | 7/2010 | Croce et al. |
| 2010/0184842 A1 | 7/2010 | Croce |
| 2010/0192235 A1 | 7/2010 | Croce |
| 2010/0196426 A1 | 8/2010 | Skog et al. |

(56) References Cited

U.S. PATENT DOCUMENTS

| | | | |
|---|---|---|---|
| 2010/0197770 A1 | 8/2010 | Wang et al. | |
| 2010/0197774 A1 | 8/2010 | Croce et al. | |
| 2010/0203544 A1 | 8/2010 | Croce et al. | |
| 2010/0234241 A1 | 9/2010 | Croce et al. | |
| 2010/0249213 A1 | 9/2010 | Croce | |
| 2010/0257618 A1* | 10/2010 | Croce | C12Q 1/6809 800/10 |
| 2010/0285471 A1 | 11/2010 | Croce et al. | |
| 2010/0298410 A1 | 11/2010 | Obad et al. | |
| 2010/0305188 A1 | 12/2010 | Nakano et al. | |
| 2010/0317610 A1 | 12/2010 | Croce | |
| 2011/0003704 A1 | 1/2011 | Skog et al. | |
| 2011/0021601 A1 | 1/2011 | Park et al. | |
| 2011/0054006 A1 | 3/2011 | Slack et al. | |
| 2011/0054009 A1 | 3/2011 | Croce et al. | |
| 2011/0107440 A1 | 5/2011 | Pivaresi et al. | |
| 2011/0136124 A1 | 6/2011 | Roa et al. | |
| 2011/0166200 A1 | 7/2011 | Zhang | |
| 2011/0251150 A2 | 10/2011 | Bennett et al. | |
| 2011/0275534 A1 | 11/2011 | Cohn et al. | |

FOREIGN PATENT DOCUMENTS

| | | |
|---|---|---|
| CA | 2587189 A1 | 12/2006 |
| CN | 1719973 A | 1/2006 |
| CN | 101215560 B | 9/2010 |
| CN | 1282422 A | 1/2011 |
| EP | 1662259 A1 | 5/2006 |
| EP | 1676914 A1 | 7/2006 |
| EP | 1795203 A2 | 6/2007 |
| EP | 2354246 A1 | 8/2011 |
| EP | 2487240 A1 | 8/2012 |
| EP | 2481806 A3 | 10/2012 |
| FR | 2877350 A1 | 5/2006 |
| JP | 2005/503827 A | 2/2005 |
| JP | 2005/517452 A | 6/2005 |
| JP | 2005/192484 A | 7/2005 |
| JP | 2005/296014 A | 10/2005 |
| JP | 2008/086201 A | 4/2008 |
| JP | 5395439 B2 | 1/2014 |
| WO | 90/15156 A1 | 12/1990 |
| WO | 91/00364 A1 | 1/1991 |
| WO | 91/07424 A1 | 5/1991 |
| WO | 93/12136 A1 | 6/1993 |
| WO | 94/10343 A1 | 5/1994 |
| WO | 94/24308 A1 | 10/1994 |
| WO | 94/26930 A1 | 11/1994 |
| WO | 96/13514 A1 | 5/1996 |
| WO | 96/35124 A1 | 11/1996 |
| WO | 97/29119 A1 | 8/1997 |
| WO | 98/09510 A1 | 3/1998 |
| WO | 00/03685 A2 | 1/2000 |
| WO | 00/50565 A2 | 8/2000 |
| WO | 00/55169 A1 | 9/2000 |
| WO | 00/76524 A1 | 12/2000 |
| WO | 01/07914 A1 | 2/2001 |
| WO | 01/44466 A1 | 6/2001 |
| WO | 01/68666 A1 | 9/2001 |
| WO | 01/77343 A1 | 10/2001 |
| WO | 01/87958 A2 | 11/2001 |
| WO | 02/064171 A1 | 8/2002 |
| WO | 02/064172 A2 | 8/2002 |
| WO | 03/029459 A2 | 4/2003 |
| WO | 03/078662 A1 | 9/2003 |
| WO | 03/092370 A1 | 11/2003 |
| WO | 2004/033659 A2 | 4/2004 |
| WO | 2004/043387 A2 | 5/2004 |
| WO | 2004/079013 A1 | 9/2004 |
| WO | 2004/098377 A2 | 11/2004 |
| WO | 2005/013901 A3 | 2/2005 |
| WO | 2005/017711 A2 | 2/2005 |
| WO | 2005/020795 A2 | 3/2005 |
| WO | 2005/060661 A2 | 7/2005 |
| WO | 2005/078139 A2 | 8/2005 |
| WO | 2005/079397 A2 | 9/2005 |
| WO | 2005/080601 A2 | 9/2005 |
| WO | 2005/094263 A2 | 10/2005 |
| WO | 2005/103298 A2 | 11/2005 |
| WO | 2005/111211 A2 | 11/2005 |
| WO | 2005/118806 A2 | 12/2005 |
| WO | 2006/105486 A2 | 10/2006 |
| WO | 2006/108718 A1 | 10/2006 |
| WO | 2006/119266 A2 | 11/2006 |
| WO | 2006/119365 A3 | 11/2006 |
| WO | 2006/133022 A2 | 12/2006 |
| WO | 2006/137941 A2 | 12/2006 |
| WO | 2007/016548 A2 | 2/2007 |
| WO | 2007/033023 A2 | 3/2007 |
| WO | 2007/044413 A2 | 4/2007 |
| WO | 2007/073737 A1 | 7/2007 |
| WO | 2007/081680 A2 | 7/2007 |
| WO | 2007/081720 A2 | 7/2007 |
| WO | 2007/081740 A2 | 7/2007 |
| WO | 2007/084486 A2 | 7/2007 |
| WO | 2007/109236 A2 | 9/2007 |
| WO | 2007/112097 A2 | 10/2007 |
| WO | 2007/112754 A2 | 10/2007 |
| WO | 2007/115134 A2 | 10/2007 |
| WO | 2007/127190 A2 | 11/2007 |
| WO | 2008/008430 A2 | 1/2008 |
| WO | 2008/029295 A2 | 3/2008 |
| WO | 2008/036168 A2 | 3/2008 |
| WO | 2008/036776 A2 | 3/2008 |
| WO | 2008/054828 A2 | 5/2008 |
| WO | 2008/064519 A1 | 6/2008 |
| WO | 2008/068047 A1 | 6/2008 |
| WO | 2008/070082 A2 | 6/2008 |
| WO | 2008/073915 A2 | 6/2008 |
| WO | 2008/073920 A2 | 6/2008 |
| WO | 2008/094545 A2 | 8/2008 |
| WO | 2008/097277 A2 | 8/2008 |
| WO | 2008/136971 A1 | 11/2008 |
| WO | 2008/153987 A2 | 12/2008 |
| WO | 2008/157319 A1 | 12/2008 |
| WO | 2009/018303 A2 | 2/2009 |
| WO | 2009/020905 A2 | 2/2009 |
| WO | 2009/026487 A1 | 2/2009 |
| WO | 2009/033140 A1 | 3/2009 |
| WO | 2009/036236 A1 | 3/2009 |
| WO | 2009/049129 A1 | 4/2009 |
| WO | 2009/055773 A2 | 4/2009 |
| WO | 2009/064590 A2 | 5/2009 |
| WO | 2009/070653 A1 | 6/2009 |
| WO | 2009/100029 A1 | 8/2009 |
| WO | 2009/108853 A1 | 9/2009 |
| WO | 2009/108856 A2 | 9/2009 |
| WO | 2009/108860 A2 | 9/2009 |
| WO | 2009/108866 A2 | 9/2009 |
| WO | 2009/152300 A1 | 12/2009 |
| WO | 2010/012667 A1 | 2/2010 |
| WO | 2010/019694 A1 | 2/2010 |
| WO | 2010/059779 A1 | 5/2010 |
| WO | 2010/065156 A1 | 6/2010 |
| WO | 2010/099161 A1 | 9/2010 |
| WO | 2011/057304 A2 | 5/2011 |
| WO | 2011/059776 A2 | 5/2011 |
| WO | 2011/063382 A1 | 5/2011 |
| WO | 2011/119553 A2 | 9/2011 |
| WO | 2011/163116 A3 | 12/2011 |
| WO | 2012/019053 A2 | 2/2012 |
| WO | 2012/065049 A2 | 5/2012 |
| WO | 2012/097047 A1 | 7/2012 |
| WO | 2012/122239 A1 | 9/2012 |

OTHER PUBLICATIONS

Australian Examination Report No. 2, Application No. 2007272947 dated May 21, 2012.
Australian Examination Report No. 2, Application No. 2007205163 dated Nov. 15, 2012.
Australian Examination Report No. 1, Application No. 2008248319 dated Jul. 12, 2012.

(56) References Cited

OTHER PUBLICATIONS

Australian Examination Report No. 1, Application No. 2008310704 dated Jun. 24, 2013.
Australian Examination Report No. 1, Application No. 2007346101 dated Jun. 21, 2012.
Australian Examination Report No. 2, Application No. 2007205257 dated Jul. 16, 2012.
Australian Examination Report No. 2, Application No. 2008282318 dated Nov. 19, 2013.
Australian Examination Report No. 1, Application No. 2007227423 dated Apr. 13, 2012.
Australian Examination Report No. 2, Application No. 2007314212 dated Apr. 29, 2013.
Australian Examination Report No. 2, Application No. 2009281969 dated Jun. 30, 2014.
Australian Examination Report No. 1, Application No. 2009281969 dated Jan. 16, 2014.
Australian Examination Report No. 2, Application No. 2007346101 dated May 24, 2013.
Australian Examination Report No. 3, Application No. 2007205163 dated Mar. 28, 2013.
Australian Examination Report No. 3, Application No. 2006291165 dated Sep. 12, 2012.
Australian Examination Report No. 1, Application No. 2008316577 dated Feb. 11, 2013.
Australian Examination Report No. 4, Application No. 2006291165 dated Jan. 7, 2013.
Australian Examination Report No. 2, Application No. 2008248319 dated Apr. 9, 2013.
Australian Examination Report No. 1, Application No. 2007314212 dated Aug. 28, 2012.
Australian Examination Report No. 2, Application No. 2006291165 dated Feb. 13, 2012.
Australian Examination Report No. 1, Application No. 2008266014 dated Jul. 6, 2012.
Australian Examination Report No. 1, Application No. 2008282318 dated Feb. 7, 2013.
Australian Examination Report No. 3, Application No. 2007205257 dated Jan. 9, 2013.
Australian Examination Report No. 1, Application No. 2008283997 dated Aug. 20, 2007.
Australian Examination Report No. 2, Application No. 2007227423 dated Mar. 1, 2013.
Australian Examination Report No. 1, Application No. 2007205257 dated Oct. 24, 2011.
Australian Examination Report No. 2, Application No. 2008288806 dated Mar. 25, 2014.
Australian Examination Report No. 1, Application No. 2007205234 dated Jun. 17, 2011.
Australian Examination Report No. 1, Application No. 2007242475 dated Mar. 30, 2012.
Australian Examination Report No. 1, Application No. 2009219197 dated Sep. 19, 2013.
Canadian Office Action, Application No. 2,635,616 dated Feb. 27, 2012.
Canadian Office Action, Application No. 2,685,840 dated Jun. 5, 2014.
Canadian Office Action, Application No. 2,621,441 dated Apr. 8, 2013.
Canadian Office Action, Application No. 2,617,581 dated Apr. 2, 2012.
Canadian Office Action, Application No. 2,617,581 dated Feb. 1, 2011.
Canadian Office Action, Application No. 2,646,051 dated Feb. 25, 2011.
Canadian Office Action, Application No. 2,621,441 dated Feb. 1, 2011.
Canadian Office Action, Application No. 2,667,617 dated Jan. 2, 2014.
Canadian Office Action, Application No. 2,811,486 dated Aug. 6, 2014.
Canadian Office Action, Application No. 2,657,030 dated Jan. 13, 2014.
Chinese 1st Office Action, Application No. 200980135456.6 dated Nov. 13, 2012.
Chinese 1st Office Action, Application No. 200780033066.9 dated Sep. 18, 2011.
Chinese 1st Office Action, Application No. 200980114564.5 dated Dec. 19, 2013.
Chinese 1st Office Action, Application No. 200980126520.4 dated Dec. 4, 2012.
Chinese 1st Office Action, Application No. 200880108625.2 dated Feb. 13, 2012.
Chinese 1st Office Action, Application No. 200980155340.9 dated Jan. 21, 2013.
Chinese 1st Office Action, Application No. 201080059339.9 dated Aug. 26, 2013.
Chinese 1st Office Action, Application No. 201210380806.9 dated Nov. 5, 2013.
Chinese 1st Office Action, Application No. 200980112966.1 dated Sep. 20, 2012.
Chinese 1st Office Action, Application No. 200880022612.3 dated Apr. 24, 2012.
Chinese 1st Office Action, Application No. 200780023093.8 dated Dec. 27, 2010.
Chinese 1st Office Action, Application No. 200880112581.0 dated Aug. 13, 2012.
Chinese 1st Office Action, Application No. 200780040146.7 dated May 25, 2011.
Chinese 1st Office Action, Application No. 200980113258.X dated Mar. 13, 2013.
Chinese 1st Office Action, Application No. 1180022637.5 dated Aug. 20, 2014.
Chinese 1st Office Action, Application No. 201110319534.7 dated Jun. 8, 2013.
Chinese 1st Office Action, Application No. 201310396056.9 dated Jul. 31, 2014.
Chinese 1st Office Action, Application No. 200780005821.2 dated Jan. 26, 2011.
Chinese 1st Office Action, Application No. 200880025276.8 dated Nov. 23, 2011.
Chinese 1st Office Action, Application No. 200880119206.9 dated May 3, 2012.
Chinese 1st Office Action, Application No. 200880112585.9 dated May 24, 2012.
Chinese 1st Office Action, Application No. 200880116343.7 dated Jan. 31, 2012.
Chinese 1st Office Action, Application No. 200880103023.8 dated Oct. 9, 2012.
Chinese 1st Office Action, Application No. 200880108689.2 dated Feb. 13, 2012.
Chinese 1st Office Action, Application No. 200980111708.1 dated Aug. 27, 2012.
Chinese 1st Office Action, Application No. 200780005791.5 dated Mar. 24, 2011.
Chinese 1st Office Action, Application No. 201310230787.6 dated May 19, 2014.
Chinese 1st Office Action, Application No. 201210312507.1 dated Jul. 29, 2013.
Chinese 1st Office Action, Application No. 200780018496.3 dated Mar. 22, 2011.
Chinese 2nd Office Action, Application No. 200880103023.8 dated Jun. 20, 2013.
Chinese 2nd Office Action, Application No. 200980135456.6 dated Aug. 1, 2013.
Chinese 2nd Office Action, Application No. 200880112581.0 dated May 10, 2013.
Chinese 2nd Office Action, Application No. 200880003736.7 dated Nov. 5, 2012.
Chinese 2nd Office Action, Application No. 200780005791.5 dated May 3, 2012.

(56) References Cited

OTHER PUBLICATIONS

Chinese 2nd Office Action, Application No. 200980126520.4 dated Aug. 14, 2013.
Chinese 2nd Office Action, Application No. 200980155340.9 dated Aug. 26, 2013.
Chinese 2nd Office Action, Application No. 200880025276.8 dated Aug. 1, 2012.
Chinese 2nd Office Action, Application No. 200780005821.2 dated Apr. 1, 2012.
Chinese 2nd Office Action, Application No. 200880116343.7 dated Oct. 22, 2012.
Chinese 2nd Office Action, Application No. 200880108689.2 dated Sep. 12, 2012.
Chinese 2nd Office Action, Application No. 200880108625.2 dated Aug. 21, 2012.
Chinese 2nd Office Action, Application No. 200880119206.9 dated Feb. 1, 2013.
Chinese 2nd Office Action, Application No. 201210380806.9 dated Jun. 23, 2014.
Chinese 2nd Office Action, Application No. 200780033066.9 dated Jun. 26, 2012.
Chinese 2nd Office Action, Application No. 200880022612.3 dated Oct. 29, 2012.
Chinese 2nd Office Action, Application No. 200680039776.8 dated Jun. 30, 2011.
Chinese 2nd Office Action, Application No. 200880112585.9 dated Jan. 21, 2013.
Chinese 2nd Office Action, Application No. 200780040146.7 dated Dec. 31, 2011.
Chinese 2nd Office Action, Application No. 200780023093.8 dated Dec. 9, 2011.
Chinese 2nd Office Action, Application No. 200980112966.1 dated May 9, 2013.
Chinese 2nd Office Action, Application No. 200680036598.3 dated Feb. 24, 2011.
Chinese 2nd Office Action, Application No. 201080059339.9 dated Apr. 9, 2014.
Chinese 2nd Office Action, Application No. 200980111708.1 dated May 20, 2013.
Chinese 2nd Office Action, Application No. 200780018496.3 dated Mar. 1, 2012.
Chinese 3rd Office Action, Application No. 200880108689.2 dated Apr. 1, 2013.
Chinese 3rd Office Action, Application No. 200880108625.2 dated Jan. 5, 2013.
Chinese 3rd Office Action, Application No. 200780023093.8 dated Jul. 2, 2012.
Chinese 3rd Office Action, Application No. 200880116343.7 dated Apr. 8, 2013.
Chinese 3rd Office Action, Application No. 200880003736.7 dated Apr. 12, 2013.
Chinese 3rd Office Action, Application No. 200780005821.2 dated Nov. 5, 2012.
Chinese 3rd Office Action, Application No. 200780040146.7 dated Apr. 25, 2012.
Chinese 3rd Office Action, Application No. 200880022612.3 dated May 17, 2013.
Chinese 3rd Office Action, Application No. 200780033066.9 dated Dec. 17, 2012.
Chinese 3rd Office Action, Application No. 200780005791.5 dated Dec. 5, 2012.
Chinese 3rd Office Action, Application No. 200980112966.1 dated Dec. 4, 2013.
Chinese 3rd Office Action, Application No. 200880119206.9 dated Aug. 12, 2013.
Chinese 3rd Office Action, Application No. 200980126520.4 dated Feb. 18, 2014.
Chinese 3rd Office Action, Application No. 200980113258.X dated Jun. 10, 2014.
Chinese 3rd Office Action, Application No. 200980135456.6 dated Feb. 8, 2014.
Chinese 3rd Office Action, Application No. 200980111708.1 dated Nov. 4, 2013.
Chinese 4th Office Action, Application No. 200880022612.3 dated Nov. 19, 2013.
Chinese 4th Office Action, Application No. 200780023093.8 dated Jan. 14, 2013.
Chinese 4th Office Action, Application No. 200780005821.2 dated May 13, 2013.
Chinese 4th Office Action, Application No. 200880116343.7 dated Jul. 10, 2013.
Chinese 4th Office Action, Application No. 200780040146.7 dated Nov. 23, 2012.
Chinese 5th Office Action, Application No. 200780040146.7 dated Apr. 16, 2013.
Chinese Rejection Decision, Application No. 200780033066.9 dated Jun. 13, 2013.
Chinese Rejection Decision, Application No. 200780018496.3 dated Sep. 5, 2012.
Chinese Rejection Decision, Application No. 200980135456.6 dated Aug. 26, 2014.
Chinese Rejection Decision, Application No. 200880103023.8 dated Feb. 13, 2014.
European Examination Report, Application No. 09830750.7 dated Apr. 18, 2013.
European Examination Report, Application No. 12179595.9 dated May 12, 2014.
European Examination Report, Application No. 12154342.5 dated Mar. 20, 2014.
European Examination Report, Application No. 07753450.1 dated Jan. 12, 2009.
European Examination Report, Application No. 09715064.3 dated Feb. 12, 2014.
European Examination Report, Application No. 12165638.3 dated Apr. 2, 2014.
European Examination Report, Application No. 12154246.8 dated Nov. 22, 2013.
European Examination Report, Application No. 12165740.7 dated Apr. 28, 2014.
European Examination Report, Application No. 12165734.0 dated Apr. 29, 2014.
European Examination Report, Application No. 08796821.0 dated Jan. 7, 2013.
European Examination Report, Application No. 07867402.5 dated Nov. 22, 2011.
European Examination Report, Application No. 12154354.0 dated Oct. 23, 2013.
European Examination Report, Application No. 07716208.9 dated Sep. 13, 2012.
European Examination Report, Application No. 07716208.9 dated Sep. 27, 2010.
European Examination Report, Application No. 07716208.9 dated Apr. 20, 2010.
European Examination Report, Application No. 12154343.3 dated Mar. 21, 2014.
European Examination Report, Application No. 12154298.9 dated Nov. 22, 2013.
European Examination Report, Application No. 08841700.1 dated Jun. 13, 2014.
European Examination Report, Application No. 07716208.9 dated Sep. 13, 2011.
European Examination Report, Application No. 06814375.9 dated Oct. 14, 2011.
European Examination Report, Application No. 08799295.4 dated Nov. 18, 2011.
European Examination Report, Application No. 08767439.6 dated Dec. 2, 2011.
European Examination Report, Application No. 06800599.0 dated Nov. 25, 2011.
European Examination Report, Application No. 07717903.4 dated Apr. 25, 2012.

(56) References Cited

OTHER PUBLICATIONS

European Examination Report, Application No. 07867402.5 dated Apr. 10, 2012.
European Examination Report, Application No. 12154348.2 dated Oct. 9, 2013.
European Examination Report, Application No. 11151749.6 dated Dec. 10, 2012.
European Examination Report, Application No. 08841700.1 dated Jun. 1, 2012.
European Examination Report, Application No. 12154341.7 dated Aug. 9, 2013.
European Examination Report, Application No. 08767439.6 dated Mar. 15, 2011.
European Examination Report, Application No. 12154337.5 dated May 19, 2014.
European Examination Report, Application No. 08768266.2 dated Apr. 18, 2011.
European Examination Report, Application No. 12154347.4 dated Oct. 9, 2013.
European Examination Report, Application No. 06800599.0 dated Jul. 25, 2014.
European Examination Report, Application No. 12154339.1 dated May 16, 2014.
European Examination Report, Application No. 12154334.2 dated May 16, 2014.
European Examination Report, Application No. 12154321.9 dated May 26, 2014.
European Examination Report, Application No. 08798444.9 dated May 15, 2014.
European Examination Report, Application No. 13159600.9 dated May 15, 2014.
European Examination Report, Application No. 09715064.3 dated Nov. 5, 2012.
European Examination Report, Application No. 12154322.7 dated May 27, 2014.
European Examination Report, Application No. 07867402.5 dated Jan. 5, 2011.
European Examination Report, Application No. 12154327.6 dated May 26, 2014.
European Examination Report, Application No. 07810382.7 dated Dec. 8, 2010.
European Examination Report, Application No. 12179592.6 dated May 12, 2014.
European Examination Report, Application No. 12154329.2 dated May 26, 2014.
European Examination Report, Application No. 07717903.4 dated Aug. 16, 2011.
European Examination Report, Application No. 09713926.5 dated Jul. 30, 2012.
European Examination Report, Application No. 11196265.0 dated Feb. 22, 2013.
European Examination Report, Application No. 11151769.4 dated Jan. 3, 2013.
European Examination Report, Application No. 12154346.6 dated Jun. 27, 2013.
European Examination Report, Application No. 08770974.7 dated Feb. 25, 2013.
European Examination Report, Application No. 12154304.5 dated Feb. 25, 2013.
European Examination Report, Application No. 09715356.3 dated Jul. 10, 2013.
European Examination Report, Application No. 08799295.4 dated Dec. 10, 2012.
European Examination Report, Application No. 12154307.8 dated Feb. 20, 2013.
European Examination Report, Application No. 11151771.0 dated Jan. 3, 2013.
European Examination Report, Application No. 07717903.4 dated Jan. 29, 2010.
European Examination Report, Application No. 08782609.5 dated Jun. 24, 2011.
European Examination Report, Application No. 08796821.0 dated Jul. 19, 2013.
European Examination Report, Application No. 12165734.0 dated Aug. 14, 2013.
European Examination Report, Application No. 11170608.1 dated May 3, 2012.
European Examination Report, Application No. 12154350.8 dated Aug. 21, 2013.
European Examination Report, Application No. 12185438.4 dated Sep. 18, 2013.
European Examination Report, Application No. 08768266.2 dated Jul. 29, 2010.
European Examination Report, Application No. 12165748.0 dated Sep. 17, 2013.
European Examination Report, Application No. 08782609.5 dated May 24, 2012.
European Extended Search Report, Application No. 12185446.7 dated Mar. 28, 2013.
European Extended Search Report, Application No. 12165734.0 dated Jan. 11, 2013.
European Extended Search Report, Application No. 11840508.3 dated Mar. 19, 2014.
European Extended Search Report, Application No. 12154354.0 dated Jan. 28, 2013.
European Extended Search Report, Application No. 12755097.8 dated Aug. 4, 2014.
European Extended Search Report, Application No. 14164377.5 dated Aug. 13, 2014.
European Extended Search Report, Application No. 07867402.5 dated Nov. 24, 2009.
European Extended Search Report, Application No. 12154351.6 dated Jan. 31, 2013.
European Extended Search Report, Application No. 131754731 dated Jul. 2, 2014.
European Extended Search Report, Application No. 13175161.2 dated Sep. 24, 2013.
European Extended Search Report, Application No. 12154343.3 dated Jul. 10, 2012.
European Extended Search Report, Application No. 12179592.6 dated Jan. 21, 2013.
European Extended Search Report, Application No. 12165636.7 dated Sep. 25, 2012.
European Extended Search Report, Application No. 12165748.0 dated Jan. 11, 2013.
European Extended Search Report, Application No. 12165740.7 dated Jan. 11, 2013.
European Extended Search Report, Application. No. 12154246.8 dated Jun. 4, 2012.
European Extended Search Report, Application No. 12154300.3 dated Dec. 7, 2012.
European Extended Search Report, Application No. 07776079.1 dated Sep. 6, 2011.
European Extended Search Report, Application No. 08767439.6 dated May 12, 2010.
European Extended Search Report, Application No. 11760035.3 dated Jul. 24, 2014.
European Extended Search Report, Application No. 12154301.1 dated Jan. 11, 2013.
European Extended Search Report, Application No. 12185438.4 dated Mar. 28, 2013.
European Extended Search Report, Application No. 12179595.9 dated Jan. 23, 2013.
European Extended Search Report, Application No. 12154353.2 dated Jan. 31, 2013.
European Extended Search Report, Application No. 12154352.4 dated Jan. 28, 2013.
European Extended Search Report, Application No. 12154350.8 dated Jan. 25, 2013.
European Extended Search Report, Application No. 12154349.0 dated Jan. 25, 2013.

(56) References Cited

OTHER PUBLICATIONS

European Extended Search Report, Application No. 10832355.1 dated May 13, 2014.
European Extended Search Report, Application No. 13159600.9 dated Sep. 19, 2013.
European Search Report, Application No. 11196265.0 dated Mar. 5, 2012.
European Search Report, Application No. 12154321.9 dated Jul. 20, 2012.
European Search Report, Application No. 09713926.5 dated Jul. 21, 2011.
European Search Report, Application No. 06825457.2 dated Sep. 16, 2009.
European Search Report, Application No. 07867402.5 dated Mar. 16, 2010.
European Search Report, Application No. 07867402.5 dated Dec. 11, 2009.
European Search Report, Application No. 08841700.1 dated Jan. 4, 2011.
European Search Report, Application No. 09715356.3 dated Jul. 12, 2012.
European Search Report, Application No. 09830750.7 dated Aug. 27, 2012.
European Search Report, Application No. 12165740.7 dated Aug. 27, 2012.
European Search Report, Application No. 12154304.5 dated Jun. 26, 2012.
European Search Report, Application No. 12165638.3 dated Jun. 12, 2012.
European Search Report, Application No. 09714868.8 dated Aug. 1, 2011.
European Search Report, Application No. 11196261.9 dated Feb. 28, 2012.
European Search Report, Application No. 11151769.4 dated Aug. 2, 2011.
European Search Report, Application No. 11151772.8 dated Aug. 2, 2011.
European Search Report, Application No. 11196250.2 dated Apr. 24, 2012.
European Search Report, Application No. 11196253.6 dated Apr. 24, 2012.
European Search Report, Application No. 11196256.9 dated Feb. 28, 2012.
European Search Report, Application No. 11170608.1 dated Aug. 29, 2011.
European Search Report, Application No. 07717903.4 dated Nov. 10, 2009.
European Search Report, Application No. 11196262.7 dated Feb. 28, 2012.
European Search Report, Application No. 11196254.4 dated Feb. 28, 2012.
European Search Report, Application No. 11151749.6 dated Aug. 2, 2011.
European Search Report, Application No. 12154298.9 dated Jun. 4, 2012.
European Search Report, Application No. 11151771.0 dated Aug. 2, 2011.
European Search Report, Application No. 12165636.7 dated Jun. 8, 2012.
European Search Report, Application No. 11196190.0 dated Apr. 24, 2012.
European Search Report, Application No. 11196264.3 dated Feb. 28, 2012.
European Search Report, Application No. 07810382.7 dated Sep. 14, 2009.
European Search Report, Application No. 08713330.2 dated Jul. 22, 2011.
European Search Report, Application No. 12154300.3 dated Jan. 7, 2013.
European Search Report, Application No. 12165734.0 dated Aug. 27, 2012.
European Search Report, Application No. 06800599.0 dated Oct. 19, 2009.
European Search Report, Application No. 12154354.0 dated Oct. 12, 2012.
European Search Report, Application No. 07717734.3 dated Nov. 9, 2009.
European Search Report, Application No. 07716208.9 dated Nov. 10, 2009.
European Search Report, Application No. 08782609.5 dated Oct. 28, 2010.
European Search Report, Application No. 12154341.7 dated Oct. 25, 2012.
European Search Report, Application No. 08770974.4 dated Oct. 21, 2011.
European Search Report, Application No. 12154342.5 dated Jul. 6, 2012.
European Search Report, Application No. 12154352.4 dated Oct. 12, 2012.
European Search Report, Application No. 12154307.8 dated Jun. 26, 2012.
European Search Report, Application No. 09807241.6 dated Dec. 6, 2012.
European Search Report, Application No. 07872618.9 dated Jul. 5, 2010.
European Search Report, Application No. 08768266.2 dated Jul. 1, 2010.
European Search Report, Application No. 09763590.8 dated Aug. 29, 2011.
European Search Report, Application No. 08796821.0 dated Aug. 4, 2010.
European Search Report, Application No. 08841700.1 dated Jun. 2, 2010.
European Search Report, Application No. 08838376.5 dated Mar. 4, 2011.
European Search Report, Application No. 08799295.4 dated Nov. 9, 2010
European Search Report, Application No. 08798444.9 dated Dec. 16, 2010.
European Search Report, Application No. 09715064.3 dated May 24, 2011.
European Search Report, Application No. 12185440.0 dated Apr. 12, 2013.
European Search Report, Application No. 12154327.6 dated Sep. 19, 2012.
European Search Report, Application No. 12154300.3 dated Aug. 20, 2012.
European Search Report, Application No. 12154301.1 dated Aug. 22, 2012.
European Search Report, Application No. 12154334.2 dated Sep. 21, 2012.
European Search Report, Application No. 12154332.6 dated Sep. 21, 2012.
European Search Report, Application No. 12154329.2 dated Sep. 19, 2012.
European Search Report, Application No. 12165748.0 dated Aug. 23, 2012.
European Search Report, Application No. 12154326.8 dated Sep. 6, 2012.
European Search Report, Application No. 07717903.4 dated Oct. 23, 2009.
European Search Report, Application No. 12154322.7 dated Aug. 29, 2012.
European Search Report, Application No. 06814375.9 dated Oct. 8, 2009.
European Search Report, Application No. 12154350.8 dated Sep. 27, 2012.
European Search Report, Application No. 12154346.6 dated Oct. 23, 2012.
European Search Report, Application No. 12154353.2 dated Oct. 15, 2012.

(56) References Cited

OTHER PUBLICATIONS

European Search Report, Application No. 12154351.6 dated Oct. 15, 2012.
European Search Report, Application No. 12154349.0 dated Sep. 27, 2012.
European Search Report, Application No. 12154347.4 dated Sep. 27, 2012.
European Search Report, Application No. 12154345.8 dated Sep. 19, 2012.
European Search Report, Application No. 12154348.2 dated Oct. 9, 2012.
European Search Report, Application No. 12154344.1 dated Sep. 19, 2012.
European Search Report, Application No. 12154339.1 dated Oct. 9, 2012.
European Search Report, Application No. 12154337.5 dated Oct. 9, 2012.
Japanese Notification of Reasons for Rejection, Application No. 2012-183280 dated Mar. 18, 2014.
Japanese Notification of Reasons for Rejection, Application No. 2009-501495 dated Jun. 11, 2013.
Japanese Notification of Reasons for Rejection, Application No. 2010-548904 dated Apr. 1, 2014.
Japanese Notification of Reasons for Rejection, Application No. 2010-511218 dated Mar. 13, 2014.
Japanese Notification of Reasons for Rejection, Application No. 2010-531311 dated Aug. 19, 2014.
Japanese Notification of Reasons for Rejection, Application No. 2010-522058 dated Aug. 1, 2014.
Japanese Notification of Reasons for Rejection, Application No. 2010-522058 dated Aug. 13, 2013.
Japanese Notification of Reasons for Rejection, Application No. 2008-525107 dated Oct. 19, 2012.
Japanese Notification of Reasons for Rejection, Application No. 2008-549555 dated Dec. 12, 2012.
Japanese Notification of Reasons for Rejection, Application No. 2012-284018 dated May 21, 2014.
Japanese Notification of Reasons for Rejection, Application No. 2010-506300 dated Mar. 12, 2014.
Japanese Notification of Reasons for Rejection, Application No. 2009-535366 dated Dec. 21, 2012.
Japanese Notification of Reasons for Rejection, Application No. 2010-506300 dated Apr. 16, 2013.
Japanese Notification of Reasons for Rejection, Application No. 2013-081761 dated May 20, 2014.
Japanese Notification of Reasons for Rejection, Application No. 2008-549532 dated Sep. 27, 2013.
Japanese Notification of Reasons for Rejection, Application No. 2009-501495 dated Jul. 27, 2012.
Japanese Notification of Reasons for Rejection, Appliction No. 2011-539528 dated Oct. 25, 2013.
Japanese Notification of Reasons for Rejection, Application No. 2010-548899 dated Oct. 8, 2013.
Japanese Notification of Reasons for Rejection, Application No. 2009-548281 dated Sep. 3, 2013.
Japanese Notification of Reasons for Rejection, Application No. 2010-548907 dated Sep. 2, 2013.
Japanese Notification of Reasons for Rejection, Application No. 2010-548904 dated Sep. 2, 2013.
Japanese Notification of Reasons for Rejection, Application No. 2010-531311 dated Sep. 2, 2013.
Japanese Notification of Reasons for Rejection, Application No. 2009-529212 dated Oct. 17, 2012.
Japanese Notification of Reasons for Rejection, Application No. 2008-549549 dated Feb. 22, 2012.
Japanese Notification of Reasons for Rejection, Application No. 2009-519525 dated Nov. 1, 2012.
Japanese Notification of Reasons for Rejection, Application No. 2009-519525 dated Jul. 9, 2012.
Japanese Notification of Reasons for Rejection, Application No. 2008-532200 dated Jan. 30, 2012.
Japanese Notification of Reasons for Rejection, Application No. 2010-512377 dated Jun. 4, 2013.
Japanese Notification of Reasons for Rejection, Application No. 2011-523144 dated Feb. 6, 2014.
Japanese Notification of Reasons for Rejection, Application No. 2008-525107 dated Jan. 4, 2012.
Japanese Notification of Reasons for Rejection, Application No. 2008-549555 dated Feb. 24, 2012.
Japanese Notification of Reasons for Rejection, Application No. 2010-511218 dated Jun. 3, 2013.
Japanese Notification of Reasons for Rejection, Application No. 2010-524221 dated Jun. 19, 2013.
Japanese Notification of Reasons for Rejection, Application No. 2010-519269 dated Jul. 12, 2013.
Japanese Notification of Reasons for Rejection, Application No. 2010-519269 dated Jun. 23, 2014.
Japanese Notification of Reasons for Rejection, Application No. 2010-529072 dated Jul. 30, 2013.
Japanese Notification of Reasons for Rejection, Application No. 2009-529212 dated Jul. 19, 2013.
Japanese Notification of Reasons for Rejection, Application No. 2010-529072 dated Jun. 4, 2014.
Japanese Notification of Reasons for Rejection, Application No. 2008-549532 dated Feb. 24, 2012.
PCT International Preliminary Report on Patentability, PCT/US2009/035470 filed Feb. 27, 2009, dated Aug. 31, 2010.
PCT International Preliminary Report on Patentability, PCT/US2008/072081 filed Aug. 4, 2008, dated Feb. 9, 2010.
PCT International Preliminary Report on Patentability, PCT/US2008/007196 filed Jun. 9, 2008, dated Dec. 11, 2009.
PCT International Preliminary Report on Patentability, PCT/US2007/023660 filed Nov. 1, 2007, dated May 5, 2009.
PCT International Preliminary Report on Patentability, PCT/US2007/020215 filed Sep. 17, 2007, dated Mar. 24, 2009.
PCT International Preliminary Report on Patentability, PCT/US2007/009910 filed Apr. 24, 2007, dated Oct. 28, 2008.
PCT International Preliminary Report on Patentability, PCT/US2007/000159 filed Jan. 3, 2007, dated Jul. 8, 2008.
PCT International Preliminary Report on Patentability, PCT/US2007/000103 filed Jan. 3, 2007, dated Jul. 8, 2008.
PCT International Preliminary Report on Patentability, PCT/US2007/006824 filed Mar. 19, 2007, dated Sep. 23, 2008.
PCT International Preliminary Report on Patentability, PCT/US2007/015892 filed Jul. 12, 2007, dated Jan. 13, 2009.
PCT International Preliminary Report on Patentability, PCT/US2007/000024 filed Jan. 3, 2007, dated Jul. 8, 2008.
PCT International Preliminary Report on Patentability, PCT/US2008/081294 filed Oct. 27, 2008, dated Apr. 27, 2010.
PCT International Preliminary Report on Patentability, PCT/US2006/038824 filed Oct. 4, 2006, dated Apr. 9, 2008.
PCT International Preliminary Report on Patentability, PCT/US2008/001157 filed Jan. 29, 2008, dated Aug. 4, 2009.
PCT International Preliminary Report on Patentability, PCT/US2008/079482 filed Oct. 10, 2008, dated Apr. 22, 2010.
PCT International Preliminary Report on Patentability, PCT/US2009/53586 filed Aug. 12, 2009, dated Feb. 24, 2011.
PCT International Preliminary Report on Patentability, PCT/US2011/034451 filed Apr. 29, 2011, dated Nov. 15, 2012.
PCT International Preliminary Report on Patentability, PCT/US2008/005503 filed Apr. 29, 2008, dated Nov. 3, 2009.
PCT International Preliminary Report on Patentability, PCT/US2009/038214 filed Mar. 25, 2009, dated Jun. 16, 2011.
PCT International Preliminary Report on Patentability, PCT/US2010/057758 filed Nov. 23, 2010, dated Jun. 7, 2012.
PCT International Preliminary Report on Patentability, PCT/US2012/068736, filed Dec. 10, 2012, dated Jun. 19, 2014.
PCT International Preliminary Report on Patentability, PCT/US2006/035100 filed Sep. 11, 2006, dated Mar. 18, 2008.
PCT International Preliminary Report on Patentability, PCT/US2009/065072 filed Nov. 19, 2009, dated Jun. 3, 2011.

(56) References Cited

OTHER PUBLICATIONS

PCT International Preliminary Report on Patentability, PCT/US2010/025173 filed Feb. 24, 2010, dated Sep. 9, 2011.
PCT International Preliminary Report on Patentability, PCT/US2008/071532 filed Jul. 30, 2008, dated Feb. 2, 2010.
PCT International Preliminary Report on Patentability, PCT/US2008/066870 filed Jun. 13, 2008, dated Dec. 17, 2009.
PCT International Preliminary Report on Patentability, PCT/US2009/035463 filed Feb. 27, 2009, dated Aug. 31, 2010.
PCT International Preliminary Report on Patentability, PCT/US2009/035482 filed Feb. 27, 2009, dated Aug. 31, 2010.
PCT International Preliminary Report on Patentability, PCT/US2009/035458 filed Feb. 27, 2009, dated Aug. 31, 2010.
PCT International Preliminary Report on Patentability, PCT/US2008/073964 filed Aug. 22, 2008, dated Feb. 24, 2010.
PCT International Preliminary Report on Patentability, PCT/US2008/075565 filed Sep. 8, 2008, dated Mar. 9, 2010.
PCT International Preliminary Report on Patentability, PCT/US2006/029889 filed Jul. 31, 2006, dated Feb. 5, 2008.
PCT International Search Report and the Written Opinion, PCT/US2009/35482 filed Feb. 27, 2009, dated Jul. 17, 2009.
PCT International Search Report and the Written Opinion, PCT/US2009/35470 filed Feb. 27, 2009, dated Jun. 16, 2009.
PCT International Search Report and the Written Opinion, PCT/US2009/35463 filed Feb. 27, 2009, dated Aug. 13, 2009.
PCT International Search Report and the Written Opinion, PCT/US2009/35458 filed Feb. 27, 2009, dated Jul. 28, 2009.
PCT International Search Report and the Written Opinion, PCT/US2008/75565 filed Sep. 8, 2008, dated Dec. 9, 2008.
PCT International Search Report and the Written Opinion, PCT/US2008/79482 filed Oct. 10, 2008, dated Dec. 22, 2008.
PCT International Search Report and the Written Opinion, PCT/US2008/72081 filed Aug. 4, 2008, dated Jan. 14, 2009.
PCT International Search Report and the Written Opinion, PCT/US2008/81294 filed Oct. 27, 2008, dated Mar. 26, 2009.
PCT International Search Report and the Written Opinion, PCT/US2009/38214 filed Mar. 25, 2009, dated Aug. 14, 2009.
PCT International Search Report and the Written Opinion, PCT/US2009/46999 filed Jun. 11, 2009, dated Nov. 23, 2009.
PCT International Search Report and the Written Opinion, PCT/US2009/53586 filed Aug. 12, 2009, dated Oct. 28, 2009.
PCT International Search Report and the Written Opinion, PCT/US2008/71532 filed Jul. 30, 2008, dated Apr. 17, 2009.
PCT International Search Report and the Written Opinion, PCT/US2011/41046 filed Jun. 20, 2011, dated Mar. 5, 2012.
PCT International Search Report and the Written Opinion, PCT/US2007/09910 filed Apr. 24, 2007, dated Feb. 13, 2008.
PCT International Search Report and the Written Opinion, PCT/US2012/62853 filed Oct. 31, 2012, dated Mar. 14, 2013.
PCT International Search Report and the Written Opinion, PCT/US2012/020911 filed Jan. 11, 2012, dated Apr. 25, 2012.
PCT International Search Report and the Written Opinion, PCT/US2011/60838 filed Nov. 15, 2011, dated Mar. 21, 2012.
PCT International Search Report and the Written Opinion, PCT/US2011/060349 filed Nov. 11, 2011, dated Feb. 10, 2012.
PCT International Search Report and the Written Opinion, PCT/US2011/29348 filed Mar. 22, 2011, dated Jun. 3, 2011.
PCT International Search Report and the Written Opinion, PCT/US2013/22492 filed Jan. 22, 2013, dated May 20, 2013.
PCT International Search Report and the Written Opinion, PCT/US2012/28016 filed Mar. 7, 2012, dated Aug. 3, 2012.
PCT International Search Report and the Written Opinion, PCT/US2010/025173 filed Feb. 24, 2010, dated Jul. 6, 2010.
PCT International Search Report and the Written Opinion, PCT/US2009/65072 filed Nov. 19, 2009, dated Mar. 3, 2010.
PCT International Search Report and the Written Opinion, PCT/US2008/73964 filed Aug. 22, 2008, dated Dec. 24, 2008.
PCT International Search Report and the Written Opinion, PCT/US2007/15892 filed Jul. 12, 2007, dated Sep. 30, 2008.
PCT International Search Report and the Written Opinion, PCT/US2007/00159 filed Jan. 3, 2007, dated Apr. 11, 2008.
PCT International Search Report and the Written Opinion, PCT/US2007/00103 filed Jan. 3, 2007, dated Dec. 3, 2007.
PCT International Search Report and the Written Opinion, PCT/US2006/29889 filed Jul. 31, 2006, dated Jul. 10, 2007.
PCT International Search Report, PCT/US2007/006824 filed Mar. 19, 2007, dated May 14, 2008.
PCT International Search Report and the Written Opinion, PCT/US2007/20215 filed Sep. 17, 2007, dated Jul. 25, 2008.
PCT International Search Report and the Written Opinion, PCT/US2012/68736 filed Dec. 10, 2012, dated Apr. 8, 2013.
PCT International Search Report and the Written Opinion, PCT/US2008/66870 filed Jun. 13, 2008, dated Nov. 10, 2008.
PCT International Search Report and the Written Opinion, PCT/US2012/67651 filed Dec. 3, 2012, dated May 13, 2013.
PCT International Search Report and the Written Opinion, PCT/US2012/060225 filed Oct. 15, 2012, dated Jan. 7, 2013.
PCT International Search Report and the Written Opinion, PCT/US2008/84821 filed Nov. 26, 2008, dated Feb. 17, 2009.
PCT International Search Report and the Written Opinion, PCT/US2006/38824 filed Oct. 4, 2006, dated Aug. 9, 2007.
PCT International Search Report and the Written Opinion, PCT/US2006/35100 filed Sep. 11, 2006, dated Sep. 5, 2007.
PCT International Search Report and the Written Opinion, PCT/US2007/00024 filed Jan. 3, 2007, dated Nov. 5, 2007.
PCT International Search Report and the Written Opinion, PCT/US2007/006824 filed Mar. 19, 2007, dated Mar. 3, 2008.
PCT International Search Report and the Written Opinion, PCT/US2007/23660 filed Nov. 1, 2007, dated Sep. 16, 2008.
PCT International Search Report and the Written Opinion, PCT/US2008/01157 filed Jan. 29, 2008, dated Aug. 7, 2008.
PCT International Search Report and the Written Opinion, PCT/US2008/05503 filed Apr. 29, 2008, dated Sep. 25, 2008.
PCT International Search Report and the Written Opinion, PCT/US2008/07196 filed Jun. 9, 2008, dated Nov. 19, 2008.
PCT International Search Report and the Written Opinion, PCT/US2012/69484 filed Dec. 13, 2012, dated Apr. 29, 2013.
PCT Written Opinion, PCT/US2009/051942 filed Jul. 28, 2009, dated Jan. 26, 2010.
Ahmad et al., "Distant Metastases of Nasopharyngeal Carcinoma: A Study of 256 Male Patients", Journal of Surgical Oncology, 1986, vol. 33, pp. 194-197.
Aiba, "Pathology of the Breast Carcinoma from the Viewpoint of the Proliferative Activity and Grade of Malignancy", Jpn J Cancer Clinical, 2000, vol. 46, No. 5, pp. 475-481.
Akahoshi et al., "Myeloproliferative Disorders Terminating in Acute Megakaryoblastic Leukemia with Chromosome 3q26 Abnormality", Cancer, 1987, vol. 60, pp. 2654-2661.
Akao et al., "let-7 MicroRNA Functions as a Potential Growth Suppressor in Human Colon Cancer Cells", Biological & Pharmaceutical Bulletin, 2006, vol. 29, No. 5, pp. 903-906.
Alberts et al., "Molecular Biology of the Cell", 3rd Edition, 1994, p. 465.
Alvarez-Secord et al., "Maspin Expression in Epithelial Ovarian Cancer and Associations with Poor Prognosis: A Gynecologic Oncology Group Study", Gynecologic Oncology, 2006, vol. 101, pp. 390-397.
Ambros et al., "A Uniform System for MicroRNA Annotation", RNA, 2003, vol. 9, pp. 277-279.
Ambros, "MicroRNA Pathways in Flies and Worms: Growth, Death, Fat, Stress, and Timing", Cell, 2003, vol. 113, pp. 673-676.
Ambs et al., "Genomic Profiling of MicroRNA and Messenger RNA Reveals Deregulated MicroRNA Expression in Prostate Cancer", Cancer Research, 2008, vol. 68, No. 15, pp. 6162-6170.
Andriani et al., "Increased Sensitivity to Cisplatin in Non-Small Cell Lung Cancer Cell Line after FHIT Gene Trnasfer", Neoplasia, 2006, vol. 8, No. 1, pp. 9-17.
Aqeilan et al., "Targeted Deletion of WWOX Reveals a Tumor Suppressor Function", Proceedings of the National Academy of Sciences (PNAS), 2007, vol. 104, No. 10, pp. 3949-3954.

(56) References Cited

OTHER PUBLICATIONS

Arata et al., "Cdk2-dependent and -independent Pathways in E2F-mediated S Phase Induction",The Jouranal of Biological Chemistry, 2000, vol. 275, No. 9, pp. 6337-6345.
Asangani et al., "MicroRNA-21 (miR-21) post-transcriptionally downregulates tumor suppressor Pdcd4 and stimulates invasion, intravasation and metastasis in colorectal cancer", Oncogene, 2008, vol. 27, pp. 2128-2136.
Attwooll et al., "The E2F family: specific functions and overlapping interests", The EMBO Journal, 2004, vol. 23, pp. 4709-4716.
Baira et al., "Ultraconserved Elements: Genomics, Function and Disease", RNA Biology, 2008, vol. 5, No. 3, pp. 132-134.
Bakkus et al., "MicroRNA Expression Analysis in Multiple Myeloma Plasma Cells and Cell Lines by a Quantitative Real-Time PCR Approach", Blood, 2007, vol. 110, Abstract 2472.
Bandres et al., "Identification by Real-Time PCR of 13 Mature MicroRNAs Differentially Expressed in Colorectal Cancer and Non-Tumoral Tissues", Molecular Cancer, 2006, vol. 5, No. 29, pp. 1-10.
Bao et al., "Anti-Tumor Activity of a Novel Compound—CDF Is Mediated by Regulating miR-21, miR-200, and PTEN in Pancreatic Caner", PLoS One, 2011, vol. 6, No. 3, pp. 1-12.
Barad et al., "MicroRNA Expression Detected by Oligonucleotide Microarrays: System Establishment and Expression Profiling in Human Tissues", Genome Research, 2004, vol. 14, pp. 2846-2494.
Bartel, "MicroRNAs: Genomics, Biogenesis, Mechanism, and Function", Cell, 2004, vol. 116, pp. 281-297.
Bartel, "MicroRNAs: Target Recognition and Regulatory Functions", Cell, 2009, vol. 136, pp. 215-233.
Basu et al., "MicroRNA-375 and MicroRNA-221:Potential Noncoding RNAs Associated with Antiproliferative Activity of Benzyl Isothiocyanate in Pancreatic Cancer", Genes & Cancer, 2011, vol. 2, No. 2, pp. 108-119.
Baudhuin et al., "Use of Microsatellite Instability and Immunohistochemistry Testing for the Identification of Individuals at Risk for Lynch Syndrome", Fam. Cancer, 2005, vol. 4, No. 3, pp. 255-265, Abstract Only.
Bednarek et al., "WWOX, the FRA16D Gene, Behaves as a Suppressor of Tumor Growth", Cancer Research, 2001, vol. 61, pp. 8068-8073.
Bejerano et al., "Computational Screening of Conserved Genomic DNA", Nature Methods, 2005, vol. 2, No. 7, pp. 535-545.
Bejerano et al., "Ultraconserved Elements in the Human Genome", Science, 2004, vol. 304, pp. 1321-1325, Electronic Supplement Data.
Bejerano et al., "Ultraconserved Elements in the Human Genome", Science, 2004, vol. 304, pp. 1321-1325.
Belinsky et al., "Inhibition of DNA Methylation and Histone Deacetylation Prevents Murine Lung Cancer", Cancer Research, 2003, vol. 63, pp. 7089-7093.
Bell, "Origins and Molecular Pathology of Ovarian Cancer", Modern Pathology, 2005, vol. 18, pp. S19-S32.
Bendoraite et al., "Regulation of miR-200 family microRNAs and ZEB transcription factors in ovarian cancer: evidence supporting a mesothelial-to-epithelial transition", Gynecologic Oncology, 2010, vol. 116, No. 1, pp. 117-125.
Bichi et al., "Human Chronic Lymphocytic Leukemia Modeled in Mouse by Targeted TCL1 Expression", Proceedings of the National Academy of Sciences (PNAS), 2002, vol. 99, No. 10, pp. 6955-6960.
Bloomston et al., "Identification of Molecular Markers Specific for Pancreatic Neuroendocrine Tumors by Genetic Profiling of Core Biopsies", Annals of Surgical Oncology, 2004, vol. 11, No. 4, pp. 413-419.
Bloomston et al., "MicroRNA Expression Patterns to Differentiate Pancreatic Adenocarcinoma from Normal Pancreas and Chronic Pancreatitis", Journal of the American Medical Association (JAMA), 2007, vol. 297, No. 17, pp. 1901-1908.
Blow et al., "Replication licensing—defining the proliferative state?", TRENDS in Cell Biology, 2002, vol. 12, No. 2, pp. 72-78.

Blum et al., "Clinical Response and miR-29b Predictive Significance in Older AML Patients Treated With a 10-Day Schedule of Decitabine", Proceedings of the National Academy of Sciences (PNAS), 2010, vol. 107, No. 16, pp. 7473-7478.
Boland et al., "Lynch Syndrome: Form, Function, Proteins, and Basketball", Gastroenterology, 2005, vol. 129, No. 2, pp. 751-755.
Bonci et al., "'Advanced' Generation Lentiviruses as Efficient Vectors for Cardiomyocyte Gene Transduction in vitro and in vivo", Gene Therapy, 2003, vol. 10, pp. 630-636.
Boominathan, "The Tumor Suppressors p53, p63, and p73 Are Regulators of MicroRNA Processing Complex", PLoS ONE, 2010, vol. 5, No. 5, pp. 1-13.
Braun et al., "p53-Responsive MicroRNAs 192 and 215 are Capable of Inducing Cell Cycle Arrest", Cancer Research, 2008, vol. 68, No. 24, pp. 10094-10104.
Brueckner et al., "The Human let-7a-3 Locus Contains an Epigenetically Regulated MicroRNA Gene with Oncogenic Function", Cancer Research, 2007, vol. 67, No. 4, pp. 1419-1423.
Budhu et al., "Prediction of venous metastases, recurrence, and prognosis in hepatocellular carcinoma based on a unique immune response signature of the liver microenvironment", Cancer Cell, 2006, vol. 10, pp. 99-111.
Budhu et al., "A Unique Metastasis-Related MicroRNA Expression Signature is a Prognostic Indicator of Survival and Recurrence in Hepatocellular Carcinoma", Hepatology, 2007, vol. 46, No. 4, Supplement 1, Abstract # 1249, p. 791A.
Budhu et al., "Identification of Metastasis-Related MicroRNAs in Hepatocellular Carcinoma", Hepatology, 2008, vol. 47, No. 3, pp. 897-907.
Butz et al., "Down-Regulation of Wee1 Kinase by a Specific Subset of microRNA in Human Sporadic Pituitary Adenomas", Journal of Clinical Endocrinology and Metabolism, 2010, vol. 95, No. 10, pp. E181-E191.
Byori to Rinsho, Pathology and Clinical Medicine, 2006, vol. 24, No. 2, pp. 167-172, Japanese Document.
Caldas et al., "Sizing Up miRNAs as Cancer Genes", Nature Medicine, 2005, vol. 11, No. 7, pp. 712-714.
Calin et al., "A MicroRNA Signature Associated with Prognosis and Progression in Chronic Lymphocytic Leukemia", The New England Journal of Medicine, 2005, vol. 353, pp. 1793-1801.
Calin et al., "Chromosomal Rearrangements and microRNAs: A New Cancer Link with Clinical Implications", The Journal of Clinical Investigation, 2007, vol. 117, No. 8, pp. 2059-2066.
Calin et al., "Frequent Deletions and Down-Regulation of MicroRNA Genes miR15 and miR16 at 13q14 in Chronic Lymphocytic Leukemia", Proceedings of the National Academy of Sciences (PNAS), 2002, vol. 99, No. 24, pp. 15524-15529.
Calin et al., "Human microRNA Genes are Frequently Located at Fragile Sites and Genomic Regions Involved in Cancers", Proceedings of the National Academy of Sciences (PNAS), 2004, vol. 101, No. 9, pp. 2999-3004.
Calin et al., "MicroRNA Signatures in Human Cancers", Nature Reviews Cancer, 2006, vol. 6, pp. 857-866.
Calin et al., "MicroRNA Profiling Reveals Distinct Signatures in B Cell Chronic Lymphocytic Leukemias", Proceedings of the National Academy of Sciences (PNAS), 2004, vol. 101, No. 32, pp. 11755-11760.
Calin et al., "MiR-15a and MiR-16-1 Cluster Functions in Human Leukemia", Proceedings of the National Academy of Sciences (PNAS), 2008, vol. 105, No. 13, pp. 5166-5171.
Calin et al., "Ultraconserved Regions Encoding ncRNAs are Altered in Human Leukemias and Carcinomas", Cancer Cell, 2007, vol. 12, pp. 215-229.
Cannistra, "Cancer of the Ovary", The New England Journal of Medicine, 2004, vol. 351, pp. 2519-2529.
Castoldi et al., "A Sensitive Array for microRNA Expression Profiling (miChip) Based on Locked Nucleic Acids (LNA)", RNA, 2006, vol. 12, pp. 913-920.
Chambers et al., "Dissemination and Growth of Cancer Cells in Metastatic Sites", Nature Reviews Cancer, 2002, vol. 2, pp. 563-572.

(56) References Cited

OTHER PUBLICATIONS

Chan et al., "Concordant and Discordant Regulation of Target Genes by miR-31 and Its Isoforms", PLoS ONE, 2013, vol. 8, No. 3, pp. 1-11.
Chan et al., "MicroRNA-21 is an Antiapoptotic Factor in Human Glioblastoma Cells", Cancer Research, 2005, vol. 65, No. 14, pp. 6029-6033.
Chang et al., "Transactivation of miR-34a by p53 Broadly Influences Gene Expression and Promotes Apoptosis", Molecular Cell, 2007, vol. 26, pp. 745-752.
Chang et al., "Molecular Mechanisms Underlying WOX1 Activation During Apoptotic and Stress Responses", Biochemical Pharmacology, 2003, vol. 66, pp. 1347-1354.
Chang et al., "Widespread MicroRNA Repression by Myc Contributes to Tumorigenesis", Nature Genetics, 2008, vol. 40, No. 1, pp. 43-50.
Chen et al., "Downregulation of miR-221/222 sensitizes glioma cells to tempzolomide by regulating apoptosis independently of p53 status", Onocolgy Reports, 2012, vol. 27, pp. 854-860.
Chen et al., "Expanded Polyglutamine-Binding Peptoid as a Novel Therapeutic Agent for Treatment of Huntington's Disease", Chemistry & Biology, 2011, vol. 18, pp. 1113-1125.
Chen et al., "Real-time quantification of microRNAs by stem-loop RT-PCR", Nucleic Acids Research, 2005, vol. 33, No. 20, pp. 1-9.
Chen et al., "MicroRNAs as Regulators of Mammalian Hematopoiesis", Seminars in Immunology, 2005, vol. 17, pp. 155-165.
Cheng et al., "Antisense Inhibition of Human miRNAs and Indications for an Involvement of miRNA in Cell Growth and Apoptosis", Nucleic Acids Research, 2005, vol. 33, No. 4, pp. 1290-1297.
Chim et al., "Detection and Characterization of Placental MicroRNAs in Maternal Plasma", Clinical Chemistry, 2008, vol. 54, No. 3, pp. 482-490.
Cho, "OncomiRs: The Discovery and Progress of MicroRNAs in Cancers", Molecular Cancer, 2007, vol. 6, No. 60, pp. 1-7.
Chun-Zhi et al., "MicroRNA-221 and microRNA-222 regulate gastric carcinoma cell proliferation and radioresistance by targeting PTEN", BMC Cancer, 2010, vol. 10, No. 367, pp. 1-10.
Ciafre et al., "Extensive Modulation of a Set of microRNAs in Primary Glioblastoma", Biochemical and Biophysical Research Communications, 2005, vol. 334, pp. 1351-1358.
Cillo et al., "The critical issue of hepatocellular carcinoma prognostic classification: which is the best tool available?", Journal of Hepatology, 2004, vol. 40, pp. 124-131.
Cimmino et al., "miR-15 and miR-16 Induce Apoptosis by Targeting BCL2", Proceedings of the National Academy of Sciences (PNAS), 2005, vol. 102, No. 39, pp. 13944-13949.
Cimmino et al., Corrections to "miR-15 and miR-16 Induce Apoptosis by Targeting BCL2", Proceedings of the National Academy of Sciences (PNAS), 2006, vol. 103, No. 7, pp. 2464-2465.
Costinean et al., "Pre-B Cell Proliferation and Lymphoblastic Leukemia/ High-Grade Lymphoma in Eμ-miR155 Transgenic Mice", Proceedings of the National Academy of Sciences (PNAS), 2006, vol. 103, No. 18, pp. 7024-7029.
Cowgill et al., "The genetics of pancreatic cancer" The American Journal of Surgery, 2003, vol. 186, pp. 279-286.
Croce et al., "miRNAs, Cancer, and Stem Cell Division", Cell, 2005, pp. 6-7.
Croce et al., "Role of FHIT in Human Cancer", Journal of Clinical Oncology, 1999, vol. 17, No. 5, pp. 1618-1624.
Croce, "Causes and Consequences of MicroRNA Dysregulation in Cancer", Nature Reviews Genetics, 2009, vol. 10, pp. 704-714.
Croce, "Oncogenes and Cancer", The New England Journal of Medicine, 2008, vol. 358, pp. 502-511.
Cui et al., "MicroRNAs that Underlie Ovarian Cancer Development and Response to Chemotherapy", American Association for Cancer Research (AACR), 98th Annual Meeting, 2007, Abstract #4514.
Dahiya et al., "MicroRNA Expression and Identification of Putative miRNA Targets in Ovarian Cancer", PLoS ONE, 2008, vol. 3, No. 6, pp. 1-11.

Dalmay et al., "MicroRNAs and the Hallmarks of Cancer", Oncogene, 2006, vol. 25, pp. 6170-6175.
Davies et al., "AZD6244 (ARRY-142886), a Potent Inhibitor of Mitogen-activated Protein Kinase/Extracellular Signal-Regulated Kinase Kinase 1/2 Kinases: Mechanism of Action in vivo, Pharmacokinetic/Pharmacodynamic Relationship, and Potential for Combination in Preclinical Needs", Molecular Cancer Therapeutics, 2007, vol. 6, No. 8, pp. 2209-2219.
Davies et al., "Insights into the Multistep Transformation of MGUS to Myeloma Using Microarray Expression Analysis", Blood, 2003, vol. 102, No. 13, pp. 4504-4511.
De Caestecker et al., "Role of Transforming Growth Factor-β Signaling in Cancer", Journal of the National Cancer Institute, 2000, vol. 92, No. 17, pp. 133-1402.
Debernardi et al., "MicroRNA miR-181a Correlates with Morphological Sub-Class of Acute Myeloid Leukemia and the Expression of its Target Genes in Global Genome-Wide Analysis", Leukemia, 2007, vol. 21, pp. 912-916.
Delott et al., "CDX2 Is a Useful Marker of Intestinal-Type Differentiation", Archives of Pathology & Laboratory Medicine, 2005, vol. 129, pp. 1100-1105.
Diccianni et al., "MicroRNA profiles of childhood T cell acute lymphoblastic leukemia", Proceedings of the American Association for Cancer Research (AACR), Meeting Abstracts, 2006, Abstract #124.
Dignam et al., "Accurate transcription initiation by RNA polymerase II in a soluble extract from isolated mammalian nuclei", Nucleic Acids Research, 1983, vol. 11, No. 5, pp. 1475-1489.
Dohner et al., "Genomic Aberrations and Survival in Chronic Lymphocytic Leukemia", The New England Journal of Medicine, 2000, vol. 343, No. 26, pp. 1910-1916.
Druck, "FHIT (Fragile Histidine Triad)", Atlas of Genetics and Cytogenetics in Oncology and Haematology, 2006, vol. 2, pp. 171-178.
Enrich et al., "Quantitative High-Throughput Analysis of DNA Methylation Patterns by Base-Specific Cleavage and Mass Spectrometry", Proceedings of the National Academy of Sciences (PNAS), 2005, vol. 102, No. 44, pp. 15785-15790.
Eiriksdottir et al., "Mapping Loss of Heterozygosity at Chromosome 13q: Loss at 13q12-q13 is Associated with Breast Tumour Progression and Poor Prognosis", European Journal of Cancer, 1998, vol. 34, No. 13, pp. 2076-2081.
Eis et al., "Accumulation of miR-155 and BIC RNA in Human B Cell Lymphomas", Proceedings of the National Academy of Sciences (PNAS), 2005, vol. 102, No. 10, pp. 3627-3632.
Esquela-Kerscher et al., "Oncomirs—MicroRNAs with a Role in Cancer", Nature Reviews Cancer, 2006, vol. 6, pp. 259-269.
Eychene et al., "A New MAFia in Cancer", Nature Reviews Cancer, 2008, vol. 8, pp. 683-693.
Fabbri et al., "MicroRNAs", The Cancer Journal, 2008, vol. 14, No. 1, pp. 1-6.
Fabbri et al., "MicroRNA-29 Family Reverts Aberrant Methylation in Lung Cancer by Targeting DNA Methyltransferases 3A and 3B", Proceedings of the National Academy of Sciences (PNAS), 2007, vol. 104, No. 40, pp. 15805-15810.
Fabbri et al., "WWOX Gene Restoration Prevents Lung Cancer Growth In Vitro and In Vivo", Proceedings of the National Academy of Sciences (PNAS), 2005, vol. 102, No. 43, pp. 15611-15616.
Faguet, "Chronic Lymphocytic Leukemia: An Updated Review", Journal of Clinical Oncology, 1994, vol. 12, No. 9, pp. 1974-1990.
Faraoni et al., "miR-155 gene: A typical multifunctional microRNA", Biochimica et Biophysica Acta, 2009, vol. 1792, pp. 497-505.
Farazi et al., "MicroRNA Sequence and Expression Analysis in Breast Tumors by Deep Sequencing", Cancer Research, 2011, vol. 71, No. 13, pp. 4443-4453.
Felli et al., "MicroRNAs 221 and 222 Inhibit Normal Erythropoiesis and Erythroleukemic Cell Growth via Kit Receptor Down-Modulation", Proceedings of the National Academy of Sciences (PNAS), 2005, vol. 102, No. 50, pp. 18081-18086.
Feng et al., "Elevated Serum-Circulating RNA in Patients with Conventional Renal Cell Cancer", Anticancer Research, 2008, vol. 28, pp. 321-326.

(56) References Cited

OTHER PUBLICATIONS

Flavin et al., "MicroRNA Gene Expression Profiling in Human Ovarian and Primary Peritoneal Serous Carcinomas", United States and Canadian Academy of Pathology (USCAP), 96th Annual Meeting, 2007, Abstract #897.

Fong et al., "Muir-Torre-Like Syndrome in FHIT-Deficient Mice", Proceedings of the National Academy of Sciences (PNAS), 2000, vol. 97, No. 9, pp. 4742-4747.

Ford, "Using Synthetic miRNA Mimics for Diverting Cell Fate: A Possibility of miRNA-base Therapeutics?", Leukemia Research, 2006, vol. 30, pp. 511-513.

Fornari et al., "MiR-221 controls CDKN1C/p57 and CDKN1B/p27 expression in human hepatocellular carcinoma", Oncogene, 2008, vol. 27, pp. 5651-5661.

Fox et al., "A Single Amino Acid Substitution Makes ERK2 Susceptible to Pyridinyl Imidazole Inhibitors of p38 MAP Kinase", Protein Science, 1998, vol. 7, pp. 2249-2255.

Fujita et al., "miR-21 Gene Expression Triggered by AP-1 is Sustained Through a Double-Negative Feedback Mechanism", Journal of Molecular Biology, 2008, vol. 378, No. 3, pp. 492-504, Abstract Only.

Fulci et al., "Quantitative Technologies Establish a Novel MicroRNA Profile of Chronic Lymphocytic Leukemia", Blood, 2007, vol. 109, No. 11, pp. 4944-4951.

Gailiun, "Single microRNA Causes Cancer in Transgenic Mice", Research Communications, The Ohio State University, 2006, pp. 1-3.

Gang et al., "Expression of Programmed Cell Death 4 and Its Clinicopathological Significance in Human Pancreatic Cancer", Acta Academae Medicinae Sinicae, 2005, vol. 27, No. 5, p. 597, Abstract Only.

Garcea et al., "Molecular prognostic markers in pancreatic cancer: A systematic review", European Journal of Cancer, 2005, vol. 41, pp. 2213-2236.

Garofalo et al., "miR-221 &222 Regulate TRAIL Resistance and Enhance Tumorigenicity through PTEN and TIMP3 Downregulation", Cancer Cell, 2009, vol. 16, pp. 498-509.

Garofalo et al., "MiR-221&222 enchance migration and invasiveness of NSCLC and hepatocarcinoma cells by targeting PTEN tumor suppressor", American Association for Cancer Research (AACR), Annual Meeting, 2009, Abstract #1319.

Garofalo et al., "miR221/222 in Cancer: Their Role in Tumor Progression and Response to Therapy", Current Molecular Medicine, 2012, vol. 12, No. 1, pp. 27-33.

Garofalo et al., "MicroRNA Signatures of TRAIL Resistance in Human Non-Small Cell Lung Cancer", Oncogene, 2008, vol. 27, pp. 3845-3855.

Garzon et al., "MicroRNA Expression and Function in Cancer", TRENDS in Molecular Medicine, 2006, vol. 12, No. 12, pp. 580-587.

Garzon et al., "MicroRNA signatures associated with cytogenetics and prognosis in acute myeloid leukemia", Blood, 2008, vol. 111, No. 6, pp. 3183-3189.

Garzon et al., "MicroRNA Signatures Associated with Cytogenetics and Outcome in Acute Myeloid Leukemia", American Society of Hematology (ASH), Annual Meeting Abstracts, Part 1, 2006, vol. 108, No. 11, p. 49a, Abstract #151.

Garzon et al., "MicroRNA Signatures Associated with Cytogenetics and Prognosis in Acute Myeloid Leukemia", Blood, 2006, vol. 108, Abstract #151.

Garzon et al., "MicroRNA Fingerprints During Human Megakaryocytopoiesis", Proceedings of the National Academy of Sciences (PNAS), 2006, vol. 103, No. 13, pp. 5078-5083.

Garzon, et al., "MicroRNA 29b Functions in Acute Myeloid Leukemia", Blood, 2009, vol. 114, No. 26, pp. 5331-5341.

Ghaneh et al., "Molecular prognostic markers in pancreatic cancer", Journal of Hepato-Biliary Pancreatic Surgery, 2002, vol. 9, pp. 1-11.

Ghoshal et al., "Up-regulation of oncogenic microRNAs and down-regulation of their tumor suppressor targets play a casual role in the initiation of hepatocarcinogenesis in mice fed choline-deficient and amino acid defined diet", American Association for Cancer Research (AACR), 99th Annual Meeting, 2008, Abstract #5033.

Gironella et al., "Tumor protein 53-induced nuclear protein 1 expression is repressed by miR-155, and its restoration inhibits pancreatic tumor development", Proceedings of the National Academy of Sciences (PNAS), 2007, vol. 104, No. 41, pp. 16170-16175.

Godlewski et al., "Targeting of the Bmi-1 Oncogene/Stem Cell Renewal Factor by MicroRNA-128 Inhibits Glioma Proliferation and Self-Renewal", Cancer Research, 2008, vol. 68, No. 22, pp. 9125-9130.

Goel et al., "A Novel Mechanism for Aspirin Mediated Growth Inhibition of Human Colon Cancer Cells", Clinical Cancer Research, 2003, vol. 9, pp. 383-390.

Goel et al., "Recent insights into the pathogenesis of colorectal cancer", Current Opinion in Gastroenterology, 2010, vol. 26, pp. 47-52.

Gottardo, et al., Micro-RNAs profiling in kidney and bladder cancers, Proc. Amer. Assoc. Cancer Res., 2005, vol. 46.

Gourley et al., "WWOX Gene Expression Abolishes Ovarian Cancer Tumorigenicity In vivo and Decreases Attachment to Fibronectin via Integrin α3", Cancer Research, 2009, vol. 69, No. 11, pp. 4835-4842.

Greenbaum et al., "Comparing Protein Abundance and mRNA Expression Levels on a Genomic Scale", Genome Biology, 2003, vol. 4, No. 9, pp. 117.1-117.8.

Gregory et al., "MicroRNA Biogenesis and Cancer", Cancer Research, 2005, vol. 65, No. 9, pp. 3509-3512.

Gregory et al., "The Microprocessor complex mediates the genesis of microRNAs", Nature, 2004, vol. 432, pp. 235-240.

Greither et al., "Elevated Expression of microRNAs 155, 203, 210 and 222 in Pancreatic Tumors is Assocaited with Poorer Survival", International Journal of Cancer, 2010, vol. 126, pp. 73-80.

Grier et al., "The Pathophysiology of HOX Genes and Their Role in Cancer", Journal of Pathology, 2005, vol. 205, pp. 154-171.

Griffiths-Jones et al., "miRBase: Tools for microRNA Genomics", Nucleic Acids Research, 2008, vol. 36, pp. D154-D158.

Griffiths-Jones et al., "miRBase: microRNA Sequences, Targets and Gene Nomenclature", Nucleic Acids Research, 2006, vol. 34, pp. D140-D144.

Griffiths-Jones, "The microRNA Registry", Nucleic Acids Research, 2004, vol. 32, pp. D109-D111.

Gu et al., "The t(4;11) Chromosome Translocation of Human Acute Leukemias Fuses the ALL-7 Gene, Related to *Drosophila* trithorax, to the AF-4 Gene", Cell, 1992, vol. 71, pp. 701-708.

Guenther et al., "Global and Hox-specific roles for the MLL1 methyltransferase", Proceedings of the National Academy of Sciences (PNAS), 2005, vol. 102, No. 24, pp. 8603-8608.

Guerrette et al., "Interactions of Human hMSH2 with hMSH3 and hMSH2 with hMSH6: Examination of Mutations Found in Hereditary Nonpolyposis Colorectal Cancer", Molecular and Cellular Biology, 1998, vol. 18, No. 11, pp. 6616-6623.

Guimaraes-Sternberg et al., "MicroRNA Modulation of Megakaryoblast Fate Involves Cholinergic Signaling", Leukemia Research, 2006, vol. 30, pp. 583-595.

Guweidhi et al. "Enhanced Expression of 14-3-3sigma in Pancreatic Cancer and its Role in Cell Cycle Regulation and Apoptosis", Carcinogenesis, 2004, vol. 25, No. 9, pp. 1575-1585.

Habbe et al., "MicroRNA miR-155 is a biomarker of early pancreatic neoplasia", Cancer Biology & Therapy, 2009, vol. 8, No. 4, pp. 340-346.

Han et al., "The Drosha-DGCR8 Complex in Primary microRNA Processing", Genes & Development, 2004, vol. 18, pp. 3016-3027.

Havelange et al., "MicroRNAs: New Players in Acute Myeloid Leukemia", British Journal of Cancer, 2009, vol. 101, pp. 743-748.

Hayashita et al., "A Polycistronic MicroRNA Cluster, miR-17-92, is Overexpressed in Human Lung Cancers and Enhances Cell Proliferation", Cancer Research, 2005, vol. 65, No. 21, pp. 9628-9632.

He et al., "A MicroRNA Polycistron as a Potential Human Oncogene", Nature, 2005, vol. 435, pp. 828-833.

He et al., "MicroRNA and Esophageal Carcinoma", Journal of Nanjing Medical University, 2007, vol. 21, No. 4, pp. 201-206.

(56) References Cited

OTHER PUBLICATIONS

He et al., "The Role of microRNA Genes in Papillary Thyroid Carcinoma," Proceedings of the National Academy of Sciences (PNAS), 2005, vol. 102, No. 52, pp. 19075-19080.
Herling et al., "TCL1 Shows a Regulated Expression Pattern in Chronic Lymphocytic Leukemia that Correlates with Molecular Subtypes and Proliferative State", Leukemia, 2006, vol. 20, pp. 280-285.
Hezel et al., "Genetics and biology of pancreatic ductal adenocarcinoma", Genes & Development, 2006, vol. 20, pp. 1218-1249.
Hiromura et al., "Identification of Nerve Growth Factor-Responsive Element of the TCL1 Promoter as a Novel Negative Regulatory Element", The Journal of Biological Chemistry, 2006, vol. 281, No. 38, pp. 27753-27764.
Hitchins, "Inheritance of Epigenetic Aberrations (Constitutional Epimutations) in Cancer Susceptibility", Advances in Genetics, 2010, vol. 70, pp. 202-243.
Hu et al., "A miR-200 microRNA cluster as prognostic marker in advanced ovarian cancer", Gynecologic Oncology, 2009, vol. 114, pp. 457-464.
Huang et al., "Evaluation of predictive value of CLIP, Okuda, TNM and JIS staging systems for hepatocellular carcinoma patients undergoing surgery", Journal of Gastroenterology and Hepatology, 2005, vol. 20, pp. 765-771.
Huang et al., "Microarray Analysis of microRNA Expression in Hepatocellular Carcinoma and Non-Tumorous Tissues Without Viral Hepatitis", Journal of Gastroenterology and Hepatology, 2008, vol. 23, pp. 87-94.
Hudlebusch et al., "Expression of HOXA Genes in Patients with Multiple Myeloma", Leukemia & Lymphoma, 2004, vol. 45, No. 6, pp. 1215-1217.
Hutvagner et al., "A microRNA in a Multiple Turnover RNAi Enzyme Complex", Science, 2002, vol. 297, pp. 2056-2060.
Iizuka et al., "Oligonucleotide microarray for prediction of early intrahepatic recurrence of hepatocellular carcinoma after curative resection", The Lancet, 2003, vol. 361, pp. 923-929.
Iliopoulos et al., "Fragile Genes as Biomarkers: Epigenetic Control of WWOX and FHIT in Lung, Breast and Bladder Cancer", Oncogene, 2005, vol. 24, pp. 1625-1633.
Iliopoulos et al., "Inhibition of Breast Cancer Cell Growth In vitro and In vivo: Effect of Restoration of WWOX Expression", Clinical Cancer Research, 2007, vol. 13, No. 1, pp. 268-274.
Iorio et al., "Causes and Consequences of microRNA Dysregulation", Cancer Journal, 2012, vol. 18, No. 3, pp. 215-222.
Iorio et al., "MicroRNA dysregulation in cancer: diagnostics, monitoring and therapeutics. A comprehensive review", EMBO Molecular Medicine, 2012, vol. 4, pp. 143-159.
Iorio et al., "MicroRNAs in Cancer: Small Molecules With a Hugh Impact", Journal of Clinical Oncology, 2009, vol. 27, No. 34, pp. 5848-5856.
Iorio et al., "MicroRNA Involvement in Human Cancer", Advance Access, 2012, pp. 1126-1133.
Iorio et al., "MicroRNA Gene Expression Deregulation in Human Breast Cancer", Cancer Research, 2005, vol. 65, No. 16, pp. 7065-7070.
Iorio et al., "MicroRNA Signatures in Human Ovarian Cancer", Cancer Research, 2007, vol. 67, No. 18, pp. 8699-8707.
Ishii et al., "Effect of Adenoviral Transduction of the Fragile Histidine Triad Gene into Esophageal Cancer Cells", Cancer Research, 2001, vol. 61, pp. 1578-1584.
Ivanovska et al., "MicroRNAs in the miR-106b Family Regulate p21/CDKN1A and Promote Cell Cycle Progression", Molecular and Cellular Biology, 2008, vol. 28, No. 7, pp. 2167-2174.
Izzotti et al., "Relationships of microRNA Expression in Mouse Lung with Age and Exposure to Cigarette Smoke and Light", The FASEB Journal, 2009, vol. 23, pp. 3243-3250.
Jacobs et al., "Prevalence Screening for Ovarian Cancer in Postmenopausal Women by CA 125 Measurement and Ultrasonography", BMJ, 1993, vol. 306, pp. 1030-1034.

Jacobs et al., "Progress and Challenges in Screening for Early Detection of Ovarian Cancer", Molecular & Cellular Proteomics, 2004, vol. 3, pp. 355-366.
Janis, "Ephrin-A Binding and EphA Receptor Expression Delineate the Matrix Compartment of the Striatum", The Journal of Neuroscience, 1999, vol. 19, No. 12, pp. 4962-4971.
Jannot et al., "Tumour-related mircoRNAs Functions in Caenorhabditis elegans", Oncogene, 2006, vol. 25, pp. 6197-6201.
Jansen et al., "Epidermal Expression of the Translation Inhibitor Programmed Cell Death 4 Suppresses Tumorigenesis", Cancer Research, 2005, vol. 65, No. 14, pp. 6034-6041.
Jazbutyte et al., "MicroNRA-21: From Cancer to Cardiovascular Disease", Current Drug Targets, 2010, vol. 11, No. 8, pp. 926-935, Abstract Only.
Jemal et al., "Cancer Statistics, 2007", CA: A Cancer Journal for Clinicians, 2007, vol. 57, No. 1, pp. 43-66.
Jemal et al., "Cancer Statistics, 2008", CA: A Cancer Journal for Clinicians, 2008, vol. 58, No. 2, pp. 71-96.
Ji et al., "Induction of Apoptosis and Inhibition of Tumorigenicity and Tumor Growth by Adenovirus Vector-mediated Fragile Histidine Triad (FHIT) Gene Overexpression", Cancer Research, 1999, vol. 59, pp. 3333-3339.
Ji et al., "MicroRNA Expression, Survival, and Response to Interferon in Liver Cancer", The New England Journal of Medicine, 2009, vol. 361, No. 15, pp. 1437-1447.
Ji et al., "New Kids on the Block: Diagnostic and Prognostic MicroRNAs in Hepatocellular Carcinoma", Cancer Biology & Therapy, 2009, vol. 8, No. 16, pp. 1-8.
Jiang et al., "MicroRNA-155 Functions as an OncomiR in Breast Cancer by Trageting the Suppressor of Cytokine Signaling 1 Gene", Cancer Research, 2010, vol. 70, pp. 3119-3127.
Jiang et al., "Association of MicroRNA Expression in Hepatocellular Carcinomas with Hepatitis Infection, Cirrhosis, and Patient Survival", Clinical Cancer Research, 2008, vol. 14, No. 2, pp. 419-427.
Jiang et al., "Real-Time Expression Profiling of MicroRNA Precursors in Human Cancer Cell Lines", Nucleic Acids Research, 2005, vol. 33, No. 17, pp. 5394-5403.
Johansson et al., "Hematologic malignancies with t(4;11)(q21;q23)—a cytogenetic, morphologic, immunophenotypic and clinical study of 183 cases", Leukemia, 1998, vol. 12, pp. 779-787.
John et al., "Human MicroRNA Targets", PLoS Biology, 2004, vol. 2, No. 11, pp. 1862-1879.
Johnson et al., "RAS is Regulated by the let-7 MicroRNA Family", Cell, 2005, vol. 120, pp. 635-647, Supplemental Data.
Johnson et al., "RAS is Regulated by the let-7 MicroRNA Family", Cell, 2005, vol. 120, pp. 635-647.
Johnson, "Treatment of Chronic Lymphocytic Leukemia by Total Body Irradiation Alone and Combined With Chemotherapy", International Journal of Radiation Oncology • Biology • Physics, 1979, vol. 5, No. 2, pp. 159-164.
Jover et al., "The efficacy of adjuvant chemotherapy with 5-fluorouracil in colorectal cancer depends on the mismatch repair status", European Journal of Cancer, 2009, vol. 45, pp. 365-373.
Kan et al., "Elevated Levels of Circulating microRNA-200 Family Members Correlate with Serous Epithelial Ovarian Cancer, BMC Cancer", 2012, vol. 12, No. 627, pp. 1-9.
Kane et al., "Methylation of the hMLH1 Promoter Correlates with Lack of Expression of hMLH1 in Sporadic Colon Tumors and Mismatch Repair-defective Human Tumor Cell Lines", Cancer Research, 1997, vol. 57, pp. 808-811.
Kawasaki et al., "MicroRNA-196 Inhibits HOXB8 Expression in Myeloid Differentiation of HL60 Cells", Nucleic Acids Symposium Series, 2004, vol. 48, pp. 211-212.
Kelly et al., "CT53518, A Novel Selective FLT3 Antagonist for the Treatment of Acute Myelogenous Leukemia (AML)", Cancer Cell, 2002, vol. 1, pp. 421-432.
Kim et al., "FHIT Protein Enhances Paclitaxel-Induced Apoptosis in Lung Cancer Cells", International Journal of Cancer, 2006, vol. 118, pp. 1692-1698.
Kim et al., "Processing of intronic microRNAs", The EMBO Journal, 2007, vol. 26, No. 3, pp. 775-783.

(56) References Cited

OTHER PUBLICATIONS

Kim et al., "Elevated mRNA Levels of DNA Methyltransferase-1 as an Independent Prognostic Factor in Primary Nonsmall Cell Lung Cancer", Cancer, 2006, vol. 107, No. 5, pp. 1042-1049.
Kim, "MicroRNA Biogenesis: Coordinated Cropping and Dicing", Nature Reviews Molecular Cell Biology, 2005, vol. 6, pp. 376-385.
Kluiver et al., "Lack of BIC and MicroRNA miR-155 Expression in Primary Cases of Burkitt Lymphoma", Genes, Chromosomes & Cancer, 2006, vol. 45, pp. 147-153.
Kluiver et al.,"BIC and miR-155 are highly expressed in Hodgkin, primary mediastinal and diffuse large B cell lymphomas", Journal of Pathology, 2005, vol. 207, pp. 243-249.
Kotoula et al., "In Situ Detection of microRNAs 146b, 221 and 222 in Human Carcinoma Tissues Reveals Tumor-Type Specific Expression Patterns", American Association for Cancer Research (AACR), 98th Annual Meeting, 2007, Abstract #1780.
Koturbash et al., "Role of Epigenetic Effectors in Maintenance of the Long-Term Persistent Bystander Effect in Spleen In vivo", Carcinogenesis, 2007, vol. 28, No. 8, pp. 1831-1838.
Kozomara et al., "miRBase: Integrating MicroRNA Annotation and Deep-Sequencing Data", Nucleic Acids Research, 2011, vol. 39, pp. D152-D157.
Krek et al., "Combinatorial MicroRNA Target Predictions", Nature Genetics, 2005, vol. 37, No. 5, pp. 495-500.
Kudo et al., "Prognostic staging system for hepatocellular carcinoma (CLIP score): its value and limitations, and a proposal for a new staging system, the Japan Integrated Staging Score (JIS score)", Journal of Gastroenterol, 2003, vol. 38, pp. 207-215.
Kulshreshtha et al., "A MicroRNA Signature of Hypoxia", Molecular and Cellular Biology, 2007, vol. 27, No. 5, pp. 1859-1867.
Kuroki et al., "Genetic Alterations of the Tumor Suppressor Gene WWOX in Esophageal Squamous Cell Carcinoma", Cancer Research, 2002, vol. 62, pp. 2258-2260.
Kutay et al., "Downregulation of miR-122 in the Rodent and Human Hepatocellular Carcinomas", Journal of Cellular Biochemistry, 2006, vol. 99, pp. 671-678.
Lacombe et al., "Efficient knockdown of MMR proteins in human CRC cells using chained microRNA contructs", American Association for Cancer Research (AACR), 100th Annual Meeting, 2009, Abstract #1291.
Lagos-Quintana et al., "Identification of Tissue-Specific MicroRNAs from Mouse", Current Biology, 2002, vol. 12, pp. 735-739.
Lagos-Quintana et al., "Identification of Novel Genes Coding for Small Expressed RNAs", Science, 2001, vol. 294, pp. 853-858.
Lagos-Quintana et al., "New MicroRNAs From Mouse to Human", RNA, 2003, vol. 9, No. 2, pp. 175-179.
Lall et al., "A Genome-Wide Map of Conserved MicroRNA Targets in C. elegans", Current Biology, 2006, vol. 16, pp. 460-471.
Landgraf et al., "A Mammalian MicroRNA Expression Atlas Based on Small RNA Library Sequencing", Cell, 2007, vol. 129, pp. 1401-1414.
Landi et al., "Gene Expression Signature of Cigarette Smoking and Its Role in Lung Adenocarcinoma Development and Survival", PLoS ONE, 2008,vol. 3, No. 2, pp. 1-8.
Landthaler et al., "The Human DiGeorge Syndrome Critical Region Gene 8 and Its *D. melanogaster* Homolog Are Required for miRNA Biogenesis", Current Biology, 2004, vol. 14, pp. 2162-2167.
Lanza et al., "mRNA/microRNA Gene Expression Profile in Microsatellite Unstable Colorectal Cancer", Molecular Cancer, 2007, vol. 6, No. 54, pp. 1-11.
Lau et al., "An Abundant Class of Tiny RNAs With Probable Regulatory Roles in Caenorhabditis elegans", Science, 2001, vol. 294, pp. 858-862.
Lawrie C. H. "MicroRNAs and Haematology: Small Molecules, Big Function", British Journal of Haematology, 2007, vol. 137, pp. 503-512.
Lawrie et al., "Detection of Elevated Levels of Tumour-Associated MicroRNAs in Serum of Patients with Diffuse Large B-Cell Lymphoma", British Journal of Haematology, 2008, vol. 141, pp. 672-675.
Lawrie, "MicroRNA, Expression in Lymphoma", Expert Opinion on Biological Therapy, 2007, vol. 7, No. 9, pp. 1363-1374.
Lecellier et al., "A Cellular MicroRNA mediates Antiviral Defense in Human Cells", Science, 2005, vol. 308, pp. 557-560.
Lee et al., "An Extensive Class of Small RNAs in Caenorhabditis Elegans", Science, 2001, vol. 294, pp. 862-864.
Lee et al., "MicroRNA maturation: stepwise processing and subcellular localization", The EMBO Journal, 2002, vol. 21, No. 17, pp. 4663-4670.
Lee et al., "MicroRNAs: Small but Potent Onogenes or Tumor Suppressors", Current Opinion in Investigational Drugs, 2006, vol. 7, No. 6, pp. 560-564.
Lee et al., "Expression Profiling Identifies MicroRNA Signature in Pancreatic Cancer", International Journal of Cancer, 2006, vol. 120, pp. 1046-1054.
Lee, "Expression and Function of MicroRNA in Human Cancer", Dissertation, The Ohio State University, 2008.
Levitt et al., "Dissociation of corticothalamic and thalamocortical axon targeting by an ephA7-mediated mechanism", International Journal of Developmental Neuroscience, 2006, vol. 24, p. 489 Abstract #S40.
Levy et al., "Staging of hepatocellular carcinoma: assessment of the CLIP, Okuda, and Child-Pugh staging systems in a cohort of 257 patients in Toronto", Gut, 2002, vol. 50, pp. 881-885.
Lewis et al., "Conserved Seed Pairing, Often Flanked by Adenosines, Indicates that Thousands of Human Genes are MicroRNA Targets", Cell, 2005, vol. 120, pp. 15-20.
Lewis et al., "Prediction of Mammalian MicroRNA Targets", Cell, 2003, vol. 115, pp. 787-798.
Li et al., "Bioinformatic Discovery of microRNA Precursors from Human ESTs and Introns", BMC Genomics, 2006, vol. 7, No. 164, pp. 1-11.
Li et al., "DNA mismatch repair (MMR)-dependent 5-fluorouracil cytotoxicity and the potential for new therapeutic targets", British Journal of Pharmacology, 2009, vol. 158, pp. 679-692.
Li et al., "Expression of serum miR-221 in human heptocellular carcinoma and its prognostic significance", Biochemical and Biophysical Research Communications, 2011, vol. 406, pp. 70-73.
Li et al., "Inhibition of PRL-3 Gene Expression in Gastric Cancer Cell Line SGC7901 via MicroRNA Suppressed Reduces Peritoneal Metastasis", Biochemical and Biophysical Research Communications, 2006, vol. 384, pp. 229-237.
Li et al., "miR-181a Is an Intrinsic Modulator of T Cell Sensitivity and Selection", Cell, 2007, vol. 129, pp. 147-161.
Lin et al., "Alteration of DNA methyltransferases contributes to 5'CpG methylation and poor prognosis in lung cancer", Lung Cancer, 2007, vol. 55, pp. 205-213.
Lipp, "MicroRNAs Inform Cancer Research: Alterations in the Expression of miRNA Genes Contribute to Pathogenesis on Broad Basis", Genetic Engineering & Biotechnology News, 2009, pp. 38-39.
Liu et al., "Characterization of in vitro and in vivo hypomethylating effects of decitabine in acute myeloid leukemia by a rapid, specific and sensitive LC-MS/MS method", Nucleic Acids Research, 2007, vol. 35, No. 5, pp. 1-8.
Liu et al., "Increased Expression of MicroRNA-221 in Gastric Cancer and Its Clinical Significance", The Journal of International Medical Research, 2012, vol. 40, pp. 467-474.
Liu et al., "Tissue Inhibitor of Metalloroteinase-1 Protects Human Breast Epithelial Cells From Extrinsic Cell Death: A Potential Oncogenic Activity of Tissue Inhibitor of Metalloproteinase-1", Cancer Research, vol. 65, No. 3, pp. 898-906.
Liu et al., "An Oligonucleotide Microchip for Genome-Wide MicroRNA Profiling in Human and Mouse Tissues", Proceedings of the National Academy of Sciences (PNAS), 2004, vol. 101, No. 26, pp. 9740-9744.
Loffler et al., "Interleukin-6-Dependent Survival of Multiple Myeloma Cells Involves the Stat3-Mediated Induction of

(56) References Cited

OTHER PUBLICATIONS

MicroRNA-21 Through a Highly Conserved Enhancer", Blood, 2007, vol. 110, No. 4, pp. 1330-1333.
Lu et al., "MicroRNA Expression Profiles Classify Human Cancers", Nature, 2005, vol. 435, pp. 834-838.
Lujambio et al., "A MicroRNA DNA Methylation Signature for Human Cancer Metastasis", Proceedings of the National Academy of Sciences (PNAS), 2008, vol. 105, No. 36, pp. 13556-13561.
Ma et al., "MicroRNAs in NF-kB signaling", Journal of Molecular Cell Biology, 2011, vol. 3, pp. 159-166.
Ma et al., "Expression of Programmed Cell Death 4 and Its Clinicopathological Significance in Human Pancreatic Cancer", Medline, 2005, pp. 597-600, Abstract Only.
Mack, "MicroRNA Gets Down to Business", Nature Biotechnology, 2007, vol. 25, No. 6, pp. 631-638.
Maiseyeu et al., "Gadolinium Containing Phosphatidylserine Liposomes for Molecular Imaging of Atherosclerosis", Journal of Lipid Research, 2010, pp. 1-9.
Marchetti et al., "EGFR Mutations in Non-Small-Cell Lung Cancer: Analysis of a Large Series of Cases and Development of a Rapid and Sensitive Method for Diagnostic Screening with Potential Implications on Pharmacologic Treatment", Journal of Clinical Oncology, 2005, vol. 23, No. 4, pp. 857-865.
Marcucci et al., "MicroRNA Expression in Cytogenetically Normal Acute Myeloid Leukemia", The New England Journal of Medicince, 2008, vol. 358, No. 18, pp. 1919-1928.
Marsit et al., "MicroRNA Responses to Cellular Stress", Cancer Research, 2006, vol. 66, No. 22, pp. 10843-10848.
Martin et al., "MicroRNA-155 Regulates Human Angiotensin II Type 1 Receptor Expression in Fibroblasts", The Journal of Biological Chemistry, 2006, vol. 281, No. 27, pp. 18277-18284.
Mascellani et al., "Using miRNA Expression Data for the Study of Human Cancer", Minerva Biotec, 2008, vol. 20, No. 1, pp. 23-30.
Masri et al., "MicroRNA Expression Analysis in Mutiple Myeloma", Blood, 2005, vol. 106, Abstract #1554.
Mattie et al., "Optimized High-Throughput MicroRNA Expression Profiling Provides Novel Biomarker Assessment of Clinical Prostate and Breast Cancer Biopsies", Molecular Cancer, 2006, vol. 5, No. 24, pp. 1-14.
Mazurek et al., "Phosphorylated Galectin-3 Mediates Tumor Necrosis Factor-Related Apoptosis-Inducing Ligand Signaling by Regulating Phosphatase and Tensin Homologue Deleted on Chromosome 10 in Human Breast Carcinoma Cells," The Journal of Biological Chemistry, 2007, vol. 282, No. 29, pp. 21337-21348.
McManus, "MicroRNAs and Cancer", Seminars in Cancer Biology, 2003, vol. 13, pp. 253-258.
Medina et al., "MicroRNAs 221 and 222 Bypass Quiescence and Compromise Cell Survival", Cancer Research, 2008, vol. 68, No. 8, pp. 2773-2780.
Medina et al., "OncomiR Addiction in an In Vivo Model of microRNA-21-Induced Pre-B-Cell Lymphoma", Nature, 2010, vol. 467, pp. 86-91.
Medina et al., "OncomiR Addicton in an in vivo Model of MicroRNA-21-Induced Pre-B-Cell Lymphoma", Nature, 2010, vol. 467, p. 1-22, Supplementary Information.
Megraw et al., "miRGen: A Database for the Study of Animal MicroRNA Genomic Organization and Function", Nucleic Acids Research, 2007, vol. 35, pp. D149-D155.
Mendell, "miRiad Roles for the miR-17-92 Cluster in Development and Disease", Cell, 2008, vol. 133, pp. 217-222.
Meng et al., "MicroRNA-21 Regulates Expression of the PTEN Tumor Suppressor Gene in Human Hepatocellular Cancer", Gastroenterology, 2007, vol. 133, pp. 647-658.
Meng et al., "Involvement of Human Micro-RNA in Growth and Response to Chemotherapy in Human Cholangiocarcinoma Cell Lines", Gastroenterology, 2006, vol. 130, pp. 2113-2129.
Mercatelli et al., "The Inhibition of the Highly Expressed Mir-221 and Mir-222 Impairs the Growth of Prostate Carcinoma Xenografts in Mice", PLoS ONE, 2008, vol. 3, No. 12, pp. 1-10.

Metzler et al., "High Expression of Precursor MicroRNA-155/BIC RNA in Children with Burkitt Lymphoma", Genes, Chromosomes & Cancer, 2004, vol. 39, pp. 167-169.
Mi et al., "MicroRNA Expression Signatures Accurately Discriminate Acute Lymphoblastic Leukemia from Acute Myeloid Leukemia", Proceedings of the National Academy of Sciences (PNAS), 2007, vol. 104, No. 50, pp. 19971-19976.
Michael et al., "Reduced Accumulation of Specific MicroRNAs in Colorectal Neoplasia", Molecular Cancer Research, 2003, vol. 1, pp. 882-891.
Miller et al., "Concurrent Chronic Lymphocytic Leukemia Cutis and Acute Myelogenous Leukemia Cutis in a Patient with Untreated CLL", The American Journal of Dermatopathology, 2001, vol. 23, No. 4, pp. 334-340.
Mishra et al., "Cancer Biomarkers: Are We Ready for the Prime Time?", Cancers, 2010, vol. 2, pp. 190-208.
Mitchell et al., "Circulating microRNAs as Stable Blood-Based Markers for Cancer Detection", Proceedings of the National Academy of Sciences (PNAS), 2008, vol. 105, No. 30, pp. 10513-10518.
Mitrovic et al., "Cancer Gene Therapy", Archive of Oncology, 2005, vol. 13, No. 1, pp. 23-26.
Mizusawa et al., "Differentiation phenotypes of pancreatic islet β- and α-cells are closely related with homeotic genes and a group of differentially expressed genes", Gene, 2004, vol. 331, pp. 53-63.
Mountzios et al., "Mechanisms of Disease: Signal Transduction in Lung Carcinogenesis—A Comparison of Smokers and Never-Smokers", Nature Clinical Practice Oncology, 2008, vol. 5, No. 10, pp. 610-618.
Mueller et al., "Comprehensive Molecular Analysis of Mismatch Repair Gene Defects in Suspected Lynch Syndrome (Hereditary Nonpoluposis Colorectal Cancer) Cases", Cancer Research, 2009, vol. 69, No. 17, pp. 7053-7061.
Murakami et al., "Comprehensive Analysis of microRNA Expression Patterns in Hepatocellular Carcinoma and Non-Tumorous Tissues", Oncogene, 2006, vol. 25, pp. 2537-2545.
Naegeli et al., "Novel Mechanisms of Ovarian Cancer Growth Inhibition, via MicroRNA Downregulation and Oxidative Damage, by a Ratioanlly Designed Histone Deacetylase Inhibitor", American Association for Cancer Research (AACR), 98th Annual Meeting, 2007, Abstract #2475.
Nakajima et al., "Non-Coding MicroRNAs hsa-let-7g and hsa-miR-181b are Associated with Chemoresponse to S-1 in Colon Cancer", Cancer Genomics & Proteomics, 2006, vol. 3, pp. 317-324.
Nakamura et al., "ALL-1 Is a Histone Methyltransferase that Assembles a Supercomplex of Proteins Involved in Transcriptional Regulation", Molecular Cell, 2002, vol. 10, pp. 1119-1128.
Nakanishi et al., "ALL1 Fusion Proteins Induce Deregulation of EphA7 and ERK Phosphorylation in Human Acute Leukemias", Proceedings of the National Academy of Sciences (PNAS), 2007, vol. 104, No. 36, pp. 14442-14447.
Nam et al., "MicroRNA Expression Profiles in Serous Ovarian Carcinoma", Clinical Cancer Research, 2008, vol. 14, No. 9, pp. 2690-2695.
Nana-Sinkam et al., "Clinical Applications for microRNAs in Cancer", Nature, 2013, vol. 93, No. 1, pp. 98-104.
Nazarov et al., "Interplay of microRNAs, transcription factors and target genes: linking dynamic expression changes to function", Nucleic Acids Research, 2013, vol. 41, No. 5, pp. 2817-2831.
Negrini et al., "MicroRNAs in Human Cancer: From Research to Therapy", Journal of Cell Science, 2007, vol. 120, No. 11, pp. 1833-1840.
Nicoloso et al., "MicroRNAs—The Micro Steering Wheel of Tumour Metastases", Nature Reviews Cancer, 2009, vol. 9, pp. 293-302.
Nippon, Journal of the Japanese Society, 1993, vol. 82, pp. 1053-1057.
Nurden, "Qualitative Disorders of Platelets and Megakaryocytes", Journal of Thrombosis and Haemostasis, 2005, vol. 3, pp. 1773-1782.
O'Connell et al., "Inositol Phosphatase SHIP1 is a Primary Target of miR-155", Proceedings of the National Academy of Sciences (PNAS), 2009, vol. 106, No. 17, pp. 7113-7118.

(56) References Cited

OTHER PUBLICATIONS

O'Donnell et al., "c-Myc-regulated microRNAs modulate E2F1 expression", Nature, 2005, vol. 435, pp. 839-843.
Okada et al., "MicroRNAs in Immune Regulation—Opportunities for Cancer Immunotherapy", The International Journal of Biochemistry & Cell Biology, 2010, vol. 42, pp. 1256-1261.
Okuda et al., "Natural History of Hepatocellular Carcinoma and Prognosis in Relation to Treatment", Cancer, 1985, vol. 56, No. 4, pp. 918-928.
Olivier et al., "CA125 and Transvaginal Ultrasound Monitoring in High-Risk Women Cannot Prevent the Diagnosis of Advanced Ovarian Cancer", Gynecologic Oncology, 2006, vol. 100, pp. 20-26.
Palamarchuk et al., "Akt Phosphorylates Tal1 Oncoprotein and Inhibits Its Repressor Activity", Cancer Research, 2005, vol. 65, No. 11, pp. 4515-4519.
Pallante et al., "MicroRNA deregulation in human thyroid papillary carcinomas", Endocrine-Related Cancer, 2006, vol. 13, pp. 497-508.
Pan et al., "Non-Steroidal Anti-Inflammatory Drugs Suppress the ERK Signaling Pathway via Block of Ras/c-Raf Interaction and Activation of MAP Kinase Phosphatases", Cellular Signaling, 2008, vol. 20, pp. 1134-1141.
Panarelli et al., "MicroRNA Expression Aids the Preoperative Diagnosis of Pancreatic Ductal Adenocarcinoma", Pancreas, 2012, vol. 41, No. 5, pp. 685-690.
Papageorgiou et al., "Interferon-α Induces TRAIL Expression and Cell Death via an IRF-1-Dependent Mechanism in Human Bladder Cancer Cells", Cancer Biology & Therapy, 2007, vol. 6, No. 6, pp. 872-879.
Park et al., "Antisense inhibition of microRNA-21 or -221 arrests cell cycle, induces apoptosis, and sensitizes the effects of gemcitabine in pancreatic adenocarcinoma", Pancreas, 2009, vol. 38, No. 7, Abstract Only.
Park et al., "miR-221 Silencing Blocks Hepatocellular Carcinoma and Promotes Survival", Cancer Research, 2011, vol. 71, No. 24, pp. 7608-7616.
Parkin. et al., "Global Cancer Statistics, 2002", CA: A Cancer Journal for Clinicians, 2005, vol. 55, pp. 74-108.
Partha et al., "Early Detection of Ovarian Cancer," Biomarkers in Medicine, 2008, vol. 2, No. 3, pp. 291-303.
Pasche et al., "TβR-I(6A) Is a Candidate Tumor Susceptibility Allele", Cancer Research, 1999, vol. 59, pp. 5678-5682.
Pasquinelli et al., "MicroRNAs: a developing story", Current Opinion in Genetics & Development, 2005, vol. 15, pp. 200-205.
Pathi et al., "GT-094, a NO-NSAID, Inhibits Colon Cancer Cell Growth by Activation of a Reaction Oxygen Species-MircoRNA-27a: ZBTB10-Specificity Protein Pathway", Molecular Cancer Research, 2011, vol. 9, pp. 195-202.
Pawelczyk et al., "Expression in *Escherichia coli* and Simple Purification of Human Fhit Protein", Protein Expression and Purification, 2000, vol. 18, No. 3, pp. 320-326.
Pedersen et al., "Onco-miR-155 targets SHIP1 to promote TNFα-dependent growth of B cell lymphomas", EMBO Molecular Medicine, 2009, vol. 1, pp. 288-295.
Pedersen et al., "Interferon Modulation of Cellular MicroRNAs as an Antiviral Mechanism", Nature, 2007, vol. 449, pp. 919-922.
Pekarsky et al., "Animal Models for Chronic Lymphocytic Leumekia", Journal of Cellular Biochemistry, 2007, vol. 100, pp. 1109-1118.
Pekarsky et al., "Tcl1 Functions as a Transcriptional Regulator and is Directly Involved in the Pathogenesis of CLL", Proceedings of the National Academy of Sciences (PNAS), 2008, vol. 105, No. 50, pp. 19643-19648.
Pekarsky et al., "Tcl1 Expression in Chronic Lymphocytic Leukemia is Regulated by miR-29 and miR-181", Cancer Research, 2006, vol. 66, No. 24, pp. 11590-11593.
Pekarsky et al., "Tcl1 Enhances Akt Kinase Activity and Mediates Its Nuclear Translocation", Proceedings of the National Academy of Sciences (PNAS), 2000, vol. 97, No. 7, pp. 3028-3033.
Petrocca et al., "MicroRNAs Deregulation in Gastric Cancer", American Association for Cancer Research (AACR), Meeting Abstracts, 2006, Abstract #5690.
Petrocca et al., "E2F1-Regulated MicroRNAs Impair TGFβ-Dependent Cell-Cycle Arrest and Apoptosis in Gastric Cancer", Cancer Cell, 2008, vol. 13, pp. 272-286.
Pichiorri et al., "Downregulation of p53-Inducible microRNAs 192, 194, and 215 Impairs the p53/MDM2 Autoregulatory Loop in Multiple Myeloma Development", Cancer Cell, 2010, vol. 18, pp. 367-381.
Pichiorri et al., "MicroRNA Signatures in Multiple Myeloma", American Association for Cancer Research (AACR), 99th Annual Meeting, 2008, Abstract #5047.
Pichiorri et al., "MicroRNAs Regulate Critical Genes Associated with Multiple Myeloma Pathogenesis", Proceedings of the National Academy of Sciences (PNAS), 2008, vol. 105, No. 35, pp. 12885-12890.
Pineau et al., "miR-221 Overexpression Contributes to Liver Tumorigenesis", Proceedings of the National Academy of Sciences (PNAS), 2010, vol. 107, No. 1, pp. 264-269.
Poliseno et al., "MicroRNAs modulate the angiogenic properties of HUVECs", Blood, 2006, vol. 108, No. 9, pp. 3068-3071.
Porkka et al., "MicroRNA Expression Profiling in Prostate Cancer", Cancer Research, 2007, vol. 67, No. 13, pp. 6130-6135.
Pouponnot et al., "Cell Context Reveals a Dual Role for Maf in Oncogenesis", Oncogene, 2006, vol. 25, pp. 1299-1310.
Poy et al., "A pancreatic islet-specific microRNA regulates insulin secretion", Nature, 2004, vol. 432, pp. 226-230.
Prueitt et al., "Expression of MicroRNAs and Protein-Coding Genes Associated with Perineural Invasion in Prostate Cancer", The Prostate, 2008, vol. 68, pp. 1152-1164.
Pruitt et al., "NCBI Reference Sequence (RefSeq): A Curated Non-Redundant Sequence Database of Genomes, Transcripts and Proteins", Nucleic Acids Research, 2005, vol. 33, pp. D501-D504.
Pu et al., "Circulating miR-221 directly amplified from plasma is a potential diagnostic and prognostic marker of colorectal cancer and is correlated with p53 expression", Journal of Gastroenterology and Hepatology, 2010, vol. 25, pp. 1674-1680.
Qin et al., "A Role for the WWOX Gene in Prostate Cancer", Cancer Research, 2006, vol. 66, No. 13, pp. 6477-6481.
Ramkissoon et al., "Hematopoietic-Specific microRNA Expression in Human Cells", Leukemia Research, 2006, vol. 30, pp. 643-647.
Ren et al., "Co-delivery of as-miR-21 and 5-FU by Poly (amidoamine) Dendrimer Attenuates Human Glioma Cell Growth in Vitro", Journal of Biomaterials Science, 2010, vol. 21, pp. 303-314.
Resnick et al., "The detection of differentially expressed microRNAs from the serum of ovarian cancer patients using a novel real-time PCR platform", Gynecologic Oncology, 2009, vol. 112, pp. 55-59.
Ribas et al., "The Transcriptional Regulation of miR-21, its Multiple Transcripts, and Their Implication in Prostate Cancer", Cell Cycle, 2010, vol. 9, No. 5, pp. 923-929.
Rockerfeller University, "For Different Species, Different Functions for Embryonic MircoRNAs", Science Daily, 2009, Retrieved Nov. 8, 2013 from Web address: http://www.sciencedaily.com/release/2009/05/090522171001.htm.
Roldo et al., "MicroRNA Expression Abnormalities in Pancreatic Endocrine and Acinar Tumors Are Associated With Distinctive Pathologic Feature and Clinical Behavior", Journal of Clinical Oncology, 2006, vol. 24, No. 29, pp. 4677-4684.
Rosa et al., "The miR-430/427/302 Family Controls Mesendodermal Fate Specification via Species-Specific Target Selection", Developmental Cell, 2009, vol. 16, pp. 517-527.
Rossi et al., "MicroRNA Fingerprinting of CLL Patients with Chromosome 17p Deletion Identify a miR-21 Score that Stratifies Early Survival", Blood, 2010, vol. 116, No. 6, pp. 945-952.
Rossi,et al., "Modification of MiR gene expression pattern in human colon cancer cells following exposure to 5-fluorouracil in vitro", Pharmacological Research, 2007, vol. 56, No. 3, pp. 248-253.

(56) References Cited

OTHER PUBLICATIONS

Rozovskaia et al., "Expression Profiles of Acute Lymphoblastic and Myeloblastic Leukemias with ALL-1 Rearrangements", Proceedings of the National Academy of Sciences (PNAS), 2003, vol. 100, No. 13, pp. 7853-7858.
Ryu et al., "Aberrant MicroRNA-155 Expression is an Early Event in the Multistep Progression of Pancreatic Adenocarcinoma", Pancreatology, 2010, vol. 10, pp. 66-73.
Sah et al., "Translation Inhibitors Sensitize Prostate Cancer Cells to Apoptosis Induced by Tumor Necrosis Factor-related Apoptosis-inducing Ligand (TRAIL) by Activating c-Jun N-terminal Kinase", The Journal of Biological Chemistry, 2003, vol. 278, pp. 20593-20602.
Saini et al., "Annotation of Mammalian Primary microRNAs", BioMed Central Genomics, 2008, vol. 9, No. 564, pp. 1-19.
Saito et al., "Specific Activation of microRNA-127 with Downregulation of the Proto-Oncogene BCL6 by Chromatin-Modifying Drugs in Human Cancer Cells", Cancer Cell, 2006, vol. 9, pp. 435-443.
Salovaara et al., "Population-Based Molecular Detection of Hereditary Nonpolyposis Colorectal Cancer", Journal of Clinical Oncology, 2000, vol. 18, No. 11, pp. 2193-2200.
Santanam et al., "Chronic Lymphocytic Leukemia Modeled in Mouse by Targeted miR-29 Expression", Proceedings of the National Academy of Sciences (PNAS), 2010, vol. 107, No. 27, pp. 12210-12215.
Sarver et al., "Human Colon Cancer Profiles Show Differential microRNA Expression Depending on Mismatch Repair Status and are Characteristic of Undifferentiated Proliferative States", BioMed Central Cancer, 2009, vol. 9, No. 401, pp. 1-15.
Sasaki, et al., "Coordinated Expression of ncRNAs and HOX mRNAs in the Human HOXA Locus", Biochemical and Biophysical Research Communications, 2007, vol. 357, pp. 724-730.
Schagen et al., "Genetic Targeting of Adenovirus Vectors Using a Reovirus σ1-Based Attachment Protein", Molecular Therapy, 2006, vol. 13, No. 5, pp. 997-1005.
Schetter et al., "Association of Inflammation-Related and microRNA Gene Expression with Cancer Specific Mortality of Colon Adenocarcinoma", Clinical Cancer Research, 2009, vol. 15, No. 18, pp. 5878-5887.
Schetter et al., "MicroRNA Expression Profiles Associated With Prognosis and Therapeutic Outcome in Colon Adenocarcinoma", Journal of the American Medical Association (JAMA,) 2008, vol. 299, No. 4, pp. 425-436.
Schmittgen et al., "A High-Throughput Method to Monitor the Expression of MicroRNA Precursors", Nucleic Acids Research, 2004, vol. 32, No. 4, pp. 1-10.
Schrump et al.,"Targeting the Epigenome for the Treatment and Prevention of Lung Cancer", Seminars in Oncology, 2005, vol. 32, pp. 488-502.
Seike et al., "MiR-21 is an EGFR-Regulated Anti-Apoptotic Factor in Lung Cancer in Never-Smokers", Proceedings of the National Academy of Sciences (PNAS), 2009, vol. 106, No. 29, pp. 12085-12090.
Seike et al., "MiR-21 is an EGFR-Regulated Anti-Apoptotic Factor in Lung Cancer in Never-Smokers", Proceedings of the National Academy of Sciences (PNAS), 2009, vol. 106, No. 29, pp. 12085-12090, Supporting Information.
Seike, "MicroRNA Expression Profiles in Lung Cancer Cooperated with Drug Sensitivity to EGFR Tyrosine Kinase Inhibitor", Journal of Nippon Medical School, 2009, vol. 76, No. 5, pp. 275-276.
Selvendiran et al., "NCX-4016 a Nitro-derivative of Aspirin, Inhibits EGFR and STAT3 signaling and modulates bcl-2 Proteins in Cisplatin Resistant Human Ovarian Cancer Cells and Xenografts", Cell Cycle, 2008, vol. 7, No. 1, pp. 81-88.
Seth, "Vector-Mediated Cancer Gene Therapy", Cancer Biology & Therapy, 2005, vol. 4, No. 5, pp. 512-517.
Sevinsky et al., "Extracellular Signal-Regulated Kinase Induces the Megakaryocyte GPIIb/CD41 Gene Through MafB/Kreisler", Molecular and Cellular Biology, 2004, vol. 24, No. 10, pp. 4534-4545.
Sharma et al., "Development of Inhalational Agents for Oncologic Use", Journal of Clinical Oncology, 2001, vol. 19, No. 6, pp. 1839-1847, Abstract Only.
Shen et al., "Novel genetic variants in miR-191 gene and familial ovarian cancer", BMC Cancer, 2010, vol. 10, No. 47, pp. 1-8.
Shen et al., "A Novel Polymorphism in Human Cytosine DNA-Methyltransferase-3B Promoter is Associated with an Increased Risk of Lung Cancer", Cancer Research, 2002, vol. 62, pp. 4992-4995.
Shin et al., "Exosomal microRNAs Step into the Biomarker Arena", Gynecologic Oncology, 2008, vol. 110, pp. 1-2.
Skalsky et al., "Kaposi's Sarcoma-Associated Herpesvirus Encodes an Ortholog of miR-155", Journal of Virology, 2007, vol. 81, No. 23, pp. 12836-12845.
Slaby et al., "Altered Expression of miR-21, miR-31, miR-143 and miR-145 is Related to Clinicopathologic Features of Colorectal Cancer", Oncology, 2007, vol. 72, pp. 397-402.
Slack, "Big Roles for Small RNAs", Nature, 2010, vol. 463, p. 616.
Sonoki et al., "Insertion of microRNA-125b-1, A Human Homologue of lin-4, into a Rearranged Immunoglobulin Heavy Chain Gene Locus in a Patient with Precursor B-cell Acute Lymphoblastic Leukemia", Leukemia, 2005, vol. 19, pp. 2009-2010.
Stamatopoulos, B. et al., "MicroRNA-29c and MicroRNA-233 Down-Regulation has In Vivo Significance in Chronic Lymphocytic Leukemia and Improves Disease Risk Stratification," Blood, May 2009, pp. 5237-5245, vol. 113, No. 21.
Stenvang et al., "The utility of LNA in microRNA-based cancer diagnostics and therapeutics", Seminars in Cancer Biology, 2008, vol. 18, pp. 89-102.
Suarez-Saiz et al., "MicroRNA Expression Profiling in Acute Myelogenous Leukemia", Canada Blood, 2004, p. 320A, Abstract #1131.
Sugito et al., "RNASEN regulates Cell Proliferation and Affects Survival in Esophageal Cancer Patients", Clinical Cancer Research, 2006, vol. 12, No. 24, pp. 7322-7328.
Suh et al., "Human embryonic stem cells express a unique set of microRNAs", Developmental Biology, 2004, vol. 270, pp. 488-498.
Sun et al., "Analysis of microRNA Expression Patterns in Hepatocellular Carcinoma and Non-Tumorous Tissues by Liquichip Assay", Chinese Journal of Experimental Surgery, 2006, vol. 23, No. 8, p. 945-947.
Sun et al., "MicroRNA-221 inhibits CDKN1C/p57 expression in human colorectal carcinoma", Acta Pharmacologica Sinica, 2011, vol. 32, pp. 375-384.
Suzuki et al., "RNA Interference-Mediated Knockdown of DNA Methyltransferase 1 Leads to Promoter Demethylation and Gene Re-Expression in Human Lung and Breast Cancer Cells", Cancer Research, 2004, vol. 64, pp. 3137-3143.
Szymanski et al., "A new frontier for molecular medicine: Noncoding RNAs", Biochimica et Biophysica Acta, 2005, vol. 1756, pp. 65-75.
Taccioli et al., "Ucbase & miRfunc: A Database of Ultraconserved Sequences and MicroRNA Function", Nucleic Acids Research, 2009, vol. 37, pp. D41-D48.
Takamizawa et al., "Reduced Expression of the let-7 MicroRNAs in Human Lung Cancers in Association with Shortened Postoperative Survival", Cancer Research, 2004, vol. 64, pp. 3753-3756.
Tam,"The Emergent Role of MicroRNAs in Molecular Diagnostics of Cancer", Journal of Molecular Diagnostics, 2008, vol. 10, No. 5, pp. 411-414.
Tang et al., "A Simple Array Platform for microRNA Analysis and its Application in Mouse Tissues", RNA Journal, 2007, vol. 13, pp. 1-20.
Tanner et al., "BAALC, the human member of a novel mammalian neuroectoderm gene lineage, is implicated in hematopoiesis and acute leukemia", Proceedings of the National Academy of Sciences (PNAS), 2001, vol. 98, No. 24, pp. 13901-13906.

(56) References Cited

OTHER PUBLICATIONS

Tanzer etal., "Molecular Evolution of a MicroRNA Cluster", Journal of Molecular Biology, 2004, vol. 339, pp. 327-335.
Tatsuya et al., "Oncogenic All1 fusion proteins target Drosha-mediated microRNA processing", Proceedings of the National Academy of Sciences (PNAS), 2007, vol. 104, No. 26, pp. 10980-10985.
Tavazoie et al., "Endogenous Human mircoRNAs that Suppress Breast Cancer Metastasis", Nature, 2008, vol. 451, pp. 147-152.
Taylor et al., "MicroRNA Signatures of Tumor-Derived Exosomes as Diagnostic Biomarkers of Ovarian Cancer", Gynecologic Oncology, 2008, vol. 110, pp. 13-21.
Teachey et al., "Mammalian target of rapamycin inhibitors and their potential role in therapy in leukemia and other haematogical malignancies", British Journal of Haematology, 2009, vol. 145, pp. 569-580.
Teng et al., "Shhh! Silencing by microRNA-155," Philosophical Transactions of the Royal Society B, 2009, vol. 364, pp. 631-637.
Thomson et al., "A Custon Microarray Platform for Analysis of MicroRNA Gene Expression", Nature Methods, 2004, vol. 1, No. 1, pp. 1-7, Supplementary Data.
Thomson et al., "Extensive post-transcriptional regulation of microRNAs and its implications for cancer", Genes and Development, 2006, vol. 20, pp. 2202-2207.
Thomson et al., "A Custom Microarray Platform for Analysis of MicroRNA Gene Expression", Nature Methods, 2004, vol. 1, No. 1, pp. 1-7.
Thorgeirsson et al., "Functional Genomics of Hepatocellular Carcinoma", Hepatology, 2006, vol. 43, No. 2, Supplement 1, pp. S145-S150.
Thorgeirsson et al., "Molecular pathogenesis of human hepatocellular carcinoma", Nature Genetics, 2002, vol. 31, pp. 339-346.
Tibshirani et al., "Diagnosis of multiple cancer types by shrunken centroids of gene expression", Proceedings of the National Academy of Sciences (PNAS), 2002, vol. 99, No. 10, pp. 6567-6572.
Tili et al., "Expression and Function of micro RNAs in Immune Cells During Normal or Disease State", International Journal of Medicine Sciences, 2008, vol. 5, No. 2, pp. 73-79.
Tili et al., "Mutator Activity Induced by microRNA-155 (miR-155) Links Inflammation and Cancer", Proceedings of the National Academy of Sciences (PNAS), 2011, vol. 108, No. 12, pp. 4908-4913.
Tkachuk et al., "Involvement of a Homolog of *Drosophila* Trithorax by 11q23 Chromosomal Translocations in Acute Leukemias", Cell, 1992, vol. 71, pp. 691-700.
Tockman et al., "Considerations in Bringing a Cancer Biomarker to Clinical Application", Cancer Research, 1992, vol. 52, pp. 2711s-2718s.
Tokarz et al., "The Role of microRNA in metastatic colorectal cancer and its significance in cancer prognosis and treatment", ACTA Biochimica Polonica, 2012, vol. 59, No. 4, pp. 467-474.
Trapasso et al., "Fhit Interaction with Ferredoxin Reductase Triggers Generation of Reactive Oxygen Species and Apoptosis of Cancer Cells", The Journal of Biological Chemistry, 2008, vol. 283, No. 20, pp. 13736-13744.
Tricoli et al., "MicroRNA: Potential for Cancer Detection, Diagnosis, and Prognosis", Cancer Research, 2007, vol. 67, No. 10, pp. 4553-4555.
Tsunoda et al., "Oncogenic KRAS regulates miR-200c and miR-221/222 in a 3D-specific manner in colorectal cancer cells", Anticancer Research, 2011, vol. 31, No. 7, pp. 2453-2459, Abstract Only.
Tusher et al., "Significance analysis of microarrays applied to the ionizing radiation response", Proceedings of the National Academy of Sciences (PNAS), 2001, vol. 98, No. 9, pp. 5116-5121.
Ueda et al., "Relation Between microRNA Expression and Progression and Prognosis of Gastric Cancer: A microRNA Expression Analysis", The Lancet—Oncology, 2009, pp. 1-11.
Uil et al., "Generation of an Adenoviral Vector Containing an Addition of a Heterologous Ligand to the Serotpe 3 Fiber Knob", Cancer Gene Therapy, 2003, vol. 10, pp. 121-124.
Ulivi et al., "p16INK4A and CDH13 Hypermethylation in Tumor and Serum of Non-Small Cell Lung Cancer Patients", Journal of Cellular Physiolpogy, 2006, vol. 206, pp. 611-615.
Valeri et al., "MicroRNA-21 induces resistance to 5-fluorouracil by down-regulating human DNA MutS homolog 2 (hMSH2)", Proceedings of the National Academy of Sciences (PNAS), 2010, vol. 107, No. 49, pp. 21098-21103.
Valeri et al., "Pathogenetic and Clinical Relevance of microRNAs in Colorectal Cancer," Cancer Genomics Proteomics, 2009, vol. 6, No. 4, pp. 195-204, Abstract Only.
Valeri et al., "Epigenetics, miRNAs, and Human Cancer: A New Chapter in Human Gene Regulation", Mamm Genome, 2009, vol. 20, pp. 573-580.
Valeri et al., "Modulation of Mismatch Repair and Genomic Stability by miR-155", Proceedings of the National Academy of Sciences (PNAS), 2010, vol. 107, No. 15, pp. 6982-6987.
Van Den Eynde et al., "Is Tailored Adjuvant Treatment for Colon Cancer Possible?", Clinical Colorectal Cancer, 2010, vol. 9, No. 1, pp. 15-21.
Varnholt et al., "MicroRNA Gene Expression Profile of Hepatitis C Virus-Associated Hepatocellular Carcinoma", Hepatology, 2008, vol. 47, No. 4, pp. 1223-1232.
Varotti et al., "Comparison between the fifth and sixth editions of the AJCC/UICC TNM staging systems for hepatocellular carcinoma: multicentric study on 393 cirrhotic resected patients", European Journal of Surgical Oncology, 2005, vol. 31, pp. 760-767.
Vassilev, "Small-Molecule Antagonists of p53-MDM2 Binding", Cell Cycle, 2004, vol. 3, No. 4, pp. 419-421.
Vatolin et al., "A Novel Method to Detect Functional MicroRNA Targets", Journal of Molecular Biology, 2006, vol. 358, pp. 983-996.
Verschuur, "Acute Megakaryoblastic Leukemia", Orphanet Encyclopedia, 2004, pp. 1-5.
Virgilio et al., "Identification of the TCL1 Gene Involved in T-cell Malignancies," Proceedings of the National Academy of Sciences (PNAS), 1994, vol. 91, pp. 12530-12534.
Visone et al., "MiRNAs and Cancer", The American Journal of Pathology, 2009, vol. 174, No. 4, pp. 1131-1138.
Volinia et al., "Breast cancer signatures for invasiveness and prognosis defined by deep sequencing of microRNA", Proceedings of the National Academy of Sciences (PNAS), 2012, vol. 109, No. 8, pp. 3024-3029.
Volinia et al., "Prognostic microRNA/mRNA signature from the integrated analysis of patients with invasive breast cancer", Proceedings of the National Academy of Sciences (PNAS), 2013, Early Edition, pp. 1-5.
Volinia et al., "A MicroRNA Expression Signature of Human Solid Tumors Defines Cancer Gene Targets", Proceedings of the National Academy of Sciences (PNAS), 2006, vol. 103, No. 7, pp. 2257-2261.
Volinia et al., "Reprogramming of miRNA Networks in Cancer and Leukemia", Genome Research, 2010, vol. 20, pp. 589-599.
Wang et al., "Association Between CpG Island Methylation of the WWOX Gene and Its Expression in Breast Cancers", Tumor Biology, 2009, vol. 30, pp. 8-14.
Wang et al., "Ontogeny and Oncogenesis Balance the Transcriptional Profile of Renal Cell Cancer", Cancer Research, 2004, vol. 64, pp. 7279-7287.
Watson et al., "MicroRNA Expression Profiles in Barrett's Oesophagus", RACS Annual Scientific Congress, 2007, p. A45, Abstract #HP24.
Weidhaas, "Using microRNAs to Understand Cancer Biology", The Lancet—Oncology, 2009, p. 1.
Wiemer, "The Role of MicroRNAs in Cancer: No Small Matter", European Journal of Cancer, 2007, vol. 43, pp. 1529-1544.
Wijermans, "Low Dose Azanucleosides for High Risk (s)MDS and AML", Haematologica Reports, 2006, vol. 2, No. 15, pp. 74-76.
Wildi et al., "Critical evaluation of the different staging systems for hepatocellular carcinoma", British Journal of Surgery, 2004, vol. 91, pp. 400-408.

(56) References Cited

OTHER PUBLICATIONS

Wu et al., "Lenalidomide Enhances natural Killer Cell and Monocyte-Mediated Antibody-Dependent Cellular Cytotoxicity of Rituximab-Treated CD20+ Tumor Cells", Clinical Cancer Research, 2008, vol. 14, No. 14, pp. 4650-4657.
Wu et al., "Micro-RNA: A New Kind of Gene Regulators", Agricultural Sciences in China, 2006, vol. 5, No. 1, pp. 77-80.
Xi et al., "Prognostic Values of microRNAs in Colorectal Cancer", Biomarker Insights, 2006, vol. 1, pp. 113-121.
Yamamichi et al., "Locked Nucleic Acid In situ Hybridization Analysis of miR-21 Expression during Colorectal Cancer Development", Clinical Cancer Research, 2009, vol. 15, No. 12, pp. 4009-4016.
Yamashita et al., "Activation of Hepatic Stem Cell Marker EpCAM by Wnt-β-Catenin Signaling in Hepatocellular Carcinoma", Cancer Research, 2007, vol. 67, No. 22, pp. 10831-10839.
Yamashita et al., "EpCAM and α-Fetoprotein Expression Defines Novel Prognostic Subtypes of Hepatocellular Carcinoma", Cancer Research, 2008, vol. 68, No. 5, pp. 1451-1461.
Yanaihara et al., "Unique MicroRNA Molecular Profiles in Lung Cancer Diagnosis and Prognosis", Cancer Cell, 2006, vol. 9, pp. 189-198.
Yang et al., "Analysis of Sequence Variations in 59 MicroRNAs in Hepatocellular Carcinomas", Mutation Research, 2008, vol. 638, pp. 205-209.
Ye et al., "Predicting hepatitis B virus-positive metastatic hepatocellular carcinomas using gene expression profiling and supervised machine learning", Nature Medicine, 2003, vol. 9, No. 4, pp. 416-423.
Yekta et al., "MicroRNA-Directed Cleavage of HOXB8 mRNA", Science, 2004, vol. 304, pp. 594-596.
Yendamuri et al., "WW Domain Containing Oxidoreductase Gene Expression is Altered in Non-Small Cell Lung Cancer", Cancer Research, 2003, vol. 63, pp. 878-881.
Yi et al., "Exportin-5 mediates the nuclear export of pre-microRNAs and short hairpin RNAs", Genes & Development, 2003, vol. 17, pp. 3011-3016.
Yoo et al., "Epigenetic therapy of cancer: past, present and future", Nature Reviews Drug Discovery, 2006, vol. 5, pp. 37-50.
Yoon et al., "Prediction of Regulatory Modules Comprising MicroRNAs and Target Genes", Bioinformatics Genes and Genomes, 2005, vol. 21, Supplement 2, pp. ii93-ii100.
Yu et al., "Context-Dependent Bidirectional Regulation of the MutS Homolog 2 by Transforming Growth Factor β Contributes to Chemoresistance in Breast Cancer Cells", Molecular Cancer Research, 2010, vol. 8, No. 12, pp. 1633-1642.
Yu et al., "Human microRNA clusters: Genomic organization and expression profile in leukemia cell lines", Biochemical and Biophysical Research Communications, 2006, vol. 349, pp. 59-68.
Yu et al., "Protein Phosphatase 2A, a Negative Regulator of the ERK Signaling Pathway, Is Activated by Tyrosine Phosphorylation of Putative HLA Class II-Associated Protein I (PHAPI)/pp32 in Response to the Antiproliferative Lectin, Jacalin", The Journal of Biological Chemisty, 2004, vol. 279, No. 40, pp. 41377-41383.
Yuki et al., "Growth and Spread of Hepatocellular Carcinoma", Cancer, 1990, vol. 66, No. 10, pp. 2174-2179.
Zaman et al., "Current status and implications of microRNAs in ovarian cancer diagnosis and therapy", Jouranl of Ovarian Research, 2012, vol. 5, No. 44, pp. 1-11.
Zawacka-Pankau et al., "Expression and Simple, One-Step Purification of Fragile Histidine Triad (Fhit) Tumor Suppressor Mutant Forms in *Escherichia coli* and their Interaction with Protoporphyrin IX", Biotechnology Letters, 2007, vol. 29, pp. 877-883.
Zeng et al., "Recognition and Cleavage of Primary microRNA Precursors by the Nuclear Processing Enzyme Drosha", The EMBO Journal, 2005, vol. 24, pp. 138-148.
Zhang et al., "Genomic and Epigenetic Alterations Deregulate microRNA Expression in Human Epithelial Ovarian Cancer", Proceedings of the National Academy of Sciences (PNAS), 2008, vol. 105, No. 19, pp. 7004-7009, Supporting Information.
Zhang et al., "In Vitro Study on effect of up-regulation of PETN expression by knowck-down of miR-221 and miR-222 in lung cancer cell line A549 cells on radiosensitization", Proceedings of the 5th Chinese Academic Conference on Tumors, 2008, p. 317.
Zhang et al., "Inhibitory effect of knocking down microRNA-221 and microRNA-222 on glioma cell growth in vitro and in vivo", Chinese Journal of Oncology, 2009, vol. 31, No. 10, pp. 721-726, Abstract Only.
Zhang et al., "Genomic and Epigenetic Alterations Deregulate microRNA Expression in Human Epithelial Ovarian Cancer", Proceedings of the National Academy of Sciences (PNAS), 2008, vol. 105, No. 19, pp. 7004-7009.
Zhang et al., "microRNAs Exhibit High Frequency Genomic Alterations in Human Cancer", Proceedings of the National Academy of Sciences (PNAS), 2006, vol. 103, No. 24, pp. 9136-9141.
Zhang et al., "Three Biomarkers Identified from Serum Proteomic Analysis for the Detection of Early Stage Ovarian Cancer", Cancer Research, 2004, vol. 64, pp. 5882-5890.
Zhang, "In vitro study on effect of up-regulation of TIMP3 expression by antisense miR-221 and miR-222 on inhibition of invasiveness of glioblastoma cell U251", The 8th Conference and Symposium Proceedings, China Genetic Association, 2004-2008, p. 139.
Zhao et al., "p53 Mediates the Negative Regulation of MDM2 by Orphan Receptor TR3", The EMBO Journal, 2006, vol. 25, pp. 5703-5715.
Zhou et al., "Binding of NF-kappaB p65 subunit to the promoter elements is involved in LPS-induced transactivation of miRNA genes in human biliary epithelial cells", Nucleic Acids Research, 2010, vol. 38, No. 10, pp. 3222-3232.
Zhu et al., "MicroRNA-21 Targets the Tumor Suppressor Gene Tropomyosin 1 (TPM 1)", The Journal of Biological Chemistry, 2007, vol. 282, No. 19, pp. 14328-14336.

\* cited by examiner

CD9 (red) distribution in macrophages
higher magnification

Nuance-converted
miR-29a (blue) and F-11 (green)

Nuance-converted
Cytokeratin (red) and miR-29a (blue)

Nuance-converted
*TLR7* (green) and miR-29a (blue)

| miRNAs | Sequences |
|---|---|
| miR-16 | UAGCAGCACGUAAAUAUUGGCG |
| miR-21 | UAGCUUAUCAGACUGAUGUUGA |
| miR-21 G18 modified | UAGCUUAUCAGACUGAUUUUGA |
| miR-21 U20 modified | UAGCUUAUCAGACUGAUGUGGA |
| miR-21 G18+U20 modified | UAGCUUAUCAGACUGAUUUGGA |
| miR-29a | UAGCACCAUCUGAAAUCGGUUA |
| miR-29a U20 modified | UAGCACCAUCUGAAAUCGGGUA |
| miR-29a U21 modified | UAGCACCAUCUGAAAUCGGUCA |
| miR-29a U20+U21 modified | UAGCACCAUCUGAAAUCGGGCA |

Fig. 14B

SEQUENCE LISTING

<160> NUMBER OF SEQ ID NOS: 12

<210> SEQ ID NO 1
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1
guagugugug guagugugug                                              20

<210> SEQ ID NO 2
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 2
ugagugugug ugugugagug ugu                                             23

<210> SEQ ID NO 3
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 3
gugugaggaa augcuucugc                                                 20

<210> SEQ ID NO 4
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 4
uagcagcacg uaaauauugg cg                                              22

<210> SEQ ID NO 5
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 5
uagcuuauca gacugauguu ga                                              22

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 6
uagcuuauca gacugauuuu ga                                              22

<210> SEQ ID NO 7
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 7
uagcuuauca gacugaugug ga                                              22

```
<210> SEQ ID NO 8
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uagcuuauca gacugauuug ga                                                   22

<210> SEQ ID NO 9
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uagcaccauc ugaaaucggu ua                                                   22

<210> SEQ ID NO 10
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uagcaccauc ugaaaucggg ua                                                   22

<210> SEQ ID NO 11
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
uagcaccauc ugaaaucggu ca                                                   22

<210> SEQ ID NO 12
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
uagcaccauc ugaaaucggg ca                                                   22
```

METHODS AND COMPOSITIONS RELATED TO MIR-21 AND MIR-29A, EXOSOME INHIBITION, AND CANCER METASTASIS

CROSS-REFERENCE TO RELATED APPLICATIONS

This application claims the benefit of U.S. Provisional Application No. 61/644,980 filed May 9, 2011, and of U.S. Provisional Application No. 61/569,862 filed Dec. 13, 2011, the disclosures of which are incorporated herein by reference for all purposes.

STATEMENT REGARDING FEDERALLY SPONSORED RESEARCH

This invention was made with U.S. Government financial support under R01 CA135030 and R01 CA124541, awarded by the National Institutes of Health. The U.S. government has certain rights in the invention.

REFERENCE TO SEQUENCE LISTING

This application is being filed electronically via the USPTO EFS-WEB server, as authorized and set forth in MPEP§1730 II.B.2(a)(A), and this electronic filing includes an electronically submitted sequence (SEQ ID) listing. The entire content of this sequence listing is herein incorporated by reference for all purposes. The sequence listing is identified on the electronically filed .txt file as follows: 604_53483_SEQ_LIST_2012-066.txt, created on Dec. 11, 2012, and is 3,171 bytes in size.

BACKGROUND OF THE INVENTION

MicroRNAs are small non-coding RNAs (ncRNAs), 19-24 nucleotides in length that regulate gene expression, and are aberrantly expressed in most types of cancer. MiRNAs have also been detected in the blood of cancer patients, and can serve as circulating biomarkers. Secreted miRNAs within exosomes can be transferred from cell to cell, and can regulate gene expression in the receiving cells by canonical binding to their target messenger RNAs.

MicroRNAs (miRNAs) regulate gene expression and interact directly with proteins. Members of the Toll-like receptor family (namely, murine TLR7, and human TLR8) can recognize and bind viral single-stranded RNA (ssRNA) sequences on dendritic cells and B-lymphocytes, leading to cell activation and cytokine production. TLRs are a family of receptors through which the mammalian innate immune system recognizes the presence of invading pathogens. Both murine TLR7 and human TLR8 bind to, and are activated by 20 nucleotide (nt) long single stranded RNAs (ssRNAs), which represent physiological ligands for these two receptors, located in intracellular endosomes.

Cells of various types are known to produce and shed into their surroundings exosomes, also known as microvesicles, microparticles, ectosomes, or argosomes. Exosomes were historically regarded as cellular debris with no apparent function. However, a growing body of experimental data has suggested that exosomes have numerous biological activities. For example, platelet-derived microvesicles were shown to stimulate selected cells via membrane surface proteins (e.g., Thromb. Haemost. (1999), 82:794, or J. Biol. Chem. (1999), 274:7545). In other examples, specific effects of bioactive lipids in platelet microvesicles on certain target cells were reported (e.g., J. Biol. Chem. (2001), 276: 19672; or Cardiovasc. Res. (2001), 49(5):88). In still further examples, platelet microvesicles increased adhesion of mobilized CD34+ endothelial cells by transfer of certain surface components to the mobilized cells (e.g., Blood (2001), 89:3143). More recently, microvesicles have also been shown to comprise RNA that, at least in part, reflects the RNA content of the cell from which the exosome originated.

There is no admission that the background art disclosed in this section legally constitutes prior art.

TECHNICAL FIELD OF THE INVENTION

The present invention relates to biotechnology and medicine, including miRNAs and cancer.

SUMMARY OF THE INVENTION

In a first broad aspect, miRNAs are secreted by cancer cells in the surrounding tumor microenvironment, within exosomes (also known as microvesicles). Exosome-contained miRNAs, namely, miR-21 and miR-29a, can be engulfed by the immune cells surrounding cancer cells and then bind to Toll-like Receptor 8 (TLR8) present in the immune cells. As a consequence, TLR8 is activated and the immune cells release interleukin-6 (IL-6) and tumor necrosis factor alpha (TNF-alpha), which increase tumor growth and metastatic potential. Tumor secreted miR-21 and miR-29a can function by binding as ligands to receptors of TLRs in immune cells, triggering a TLR-mediated prometastatic inflammatory response, which leads to tumor growth and metastasis. Thus, by acting as paracrine agonists of TLRs, secreted miRNAs are key regulators of the tumor microenvironment. This mechanism of action of miRNAs is implicated in the tumor-immune system communication, and is important in tumor growth and spread, therefore is important in cancer treatment.

Embodiments of the present invention provide methods to inhibit metastasis of at least one cancer cell, comprising decreasing the levels of miR-21 and/or miR-29a in at least one cancer cell and inhibiting metastasis.

Also provided are such methods wherein miR-21 and/or miR-29a is decreased via a means selected from the group consisting of: gene therapy, small molecule, or biologic.

Also provided are such methods wherein miR-21 and/or miR29a is decreased via administration of at least one exosome inhibitor.

Also provided are such methods wherein miR-21 and/or miR-29a is decreased via administration of antisense miR-21 and/or antisense miR-29a.

Also provided are such methods wherein miR-21 and/or miR-29a is decreased via administration of locked nucleic acid anti-miR-21 inhibitor and/or locked nucleic acid anti-miR-29a inhibitor.

Embodiments of the present invention provide methods to inhibit TLR-mediated prometastatic response of at least one cancer cell, comprising decreasing the levels of miR-21 and/or miR-29a in at least one TLR-expressing cancer cell and inhibiting TLR-mediated prometastatic response.

Also provided are such methods wherein the TLR expressed is TLR7 or TLR8.

Embodiments of the present invention provide methods to inhibit tumor growth of at least one cancer cell, comprising decreasing the levels of miR-21 and/or miR-29a in at least one cancer cell and inhibiting tumor growth.

Embodiments of the present invention provide methods to inhibit miR-21 and miR-29a agonism of toll-like receptors in least one miR-21 and miR-29a expressing cancer cell, comprising decreasing the levels of miR-21 and/or miR-29a in at least one cancer cell expressing miR-21 and miR-29a, and inhibiting miR-21 and miR-29a agonism of toll-like receptors.

Embodiments of the present invention provide methods to inhibit metastasis of at least one cancer cell, comprising decreasing the levels of miR-21 and/or miR-29a in at least one non-cancerous cell in proximity to at least one cancer cell.

Embodiments of the present invention provide compositions of matter comprising at least one locked nucleic acid anti-21 inhibitor and at least one locked nucleic acid anti-29a inhibitor in at least one pharmaceutically-acceptable carrier or excipient.

Also provided are such compositions which further comprise an additional chemotherapeutic compound.

Also provided are methods to ameliorate cancer metastasis in a subject with cancer, comprising administering a composition herein to a subject with cancer.

Embodiments of the present invention provide methods to increase overall survival in a subject with cancer, comprising administering a composition herein to a subject with cancer.

Also provided are methods to decrease tumor multiplicities in a subject with cancer, comprising administering a composition herein to a subject with cancer.

Embodiments of the present invention provide methods of diagnosing risk of cancer metastasis in a subject, comprising: a.) indentifying the relative miR-21 and miR-29a expression compared to control, and b.) diagnosing increased risk of cancer metastasis in the subject if the subject has increased miR-21 and miR-29a expression compared to control, or c.) diagnosing no increased risk of cancer metastasis in the subject if the subject does not have increased miR-21 and miR-29a expression compared to control.

Also provided are such methods which further comprise designing a treatment plan based on the diagnosis.

Also provided are such methods which further comprise administration of a treatment based on the diagnosis.

Also provided are such methods which further comprise administering at least one exosome inhibitor.

Also provided are such methods which further comprise administering at least one antisense miR-21 and/or antisense miR-29a in the event that cancer metastasis is diagnosed.

Also provided are such methods which further comprise determining prognosis based on the diagnosis.

Also provided are such methods comprising: a.) reverse transcribing miR-21 RNA and miR-29a RNA from a test sample obtained from the subject to provide a set of target oligodeoxynucleotides; b.) hybridizing the target oligodeoxynucleotides to a microarray comprising miR-21-specific and miR-29a-specific probe oligonucleotides to provide a hybridization profile for the test sample; and c.) comparing the profile of step (b.) to control.

Also provided are such methods wherein step (c.) comprises comparing the test sample hybridization profile to a hybridization profile generated from a control sample.

Also provided are such methods wherein step (c.) comprises comparing the test sample hybridization profile to a database, statistics, or table of miR levels associated with samples.

Also provided are such methods wherein at least one additional miR is included in the microarray.

Embodiments of the present invention provides methods of diagnosing risk of prometastatic inflammatory response in a subject, comprising: a.) indentifying the relative miR-21 and miR-29a expression compared to control, and b.) diagnosing increased risk of prometastatic inflammatory response in the subject if the subject has increased miR-21 and miR-29a expression compared to control, or c.) diagnosing no increased risk of prometastatic inflammatory response in the subject if the subject does not have increased miR-21 and miR-29a expression compared to control.

Also provided are such methods which further comprise administering at least one antisense miR-21 and/or antisense miR-29a in the event that cancer metastasis is diagnosed.

Also provided are such methods wherein the cancer is lung cancer selected from the group consisting of: Lewis lung carcinoma; squamous cell carcinoma; non-small cell lung carcinoma; small cell lung carcinoma.

Also provided are such methods wherein the cancer is an adenocarcinoma selected from the group consisting of: alveolar basal epithelial; lung; colon; cervix, prostate; breast; esophagus, pancreas; and stomach.

Various objects and advantages of embodiments of this invention will become apparent to those skilled in the art from the following detailed description, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 1 Levels of miRNAs in exosomes derived from lung cancer cell lines and HEK-293 cells.

FIG. 2. miR-21 and miR-29a interact with murine TLR7 and human TLR8 in the endosomes.

FIG. 3. miR-21, -29a, and -147 induce TLR activation.

FIG. 4. miRNA-induced TLR7 activation increases formation of lung multiplicities in mice.

FIG. 6. NF-κB is required for miR-21 and 29a dependent (and TLR mediated) secretion of TNF-α. FIG. 14 (FIG. 6B)) for 24 h, and QUANTIBlue Assay was performed. Dotap alone was used as a negative control, and ssRNA40 as positive control for NF-κB activation. The experiment was conducted in quintuplicate and presented as average±s.d. **, P<0.0001.

FIG. 8. Only miR-29a expressing cancer cells are able to form lung tumor multiplicities. In situ hybridization for miR-29a (left panel), and for anti miR-29a (right panel) in a lung multiplicity developed by a mouse injected with LLC cells transfected with LNA anti miR-21/29a. Blue is the probe staining and pink is the counterstain. This image is representative of findings in all studied multiplicities from mice injected with LNA anti miR-21/29a.

FIG. 9. Effects of miR-16, 21 and 29a silencing on LLC cell biology.

FIG. 11. Distribution of CD9, CD63 and miR-29a.

FIG. 12. In human lung cancer CD9 is mainly produced at the tumor interface.

FIG. 13. At the tumor interface miR-29a is co-expressed with macrophage marker F-11, with TLR7 receptor but not with cancer-associated epithelial marker cytokeratin.

FIG. 14. miRNA sequence analysis. (FIG. 14B) List of miRNA sequences (SEQ ID NOS 4-12, respectively, in order of appearance) that were taken in consideration for the study of point mutations. miR-21 sequence was mutated in G18 and U20 (in red), while miR-29a was mutated in U20 and U21: these bases were substituted with the bases occupying the same position in the miR-16 sequence. Also a sequence with the combination of the two considered point mutations was generated.

DETAILED DESCRIPTION

Figure 1A:
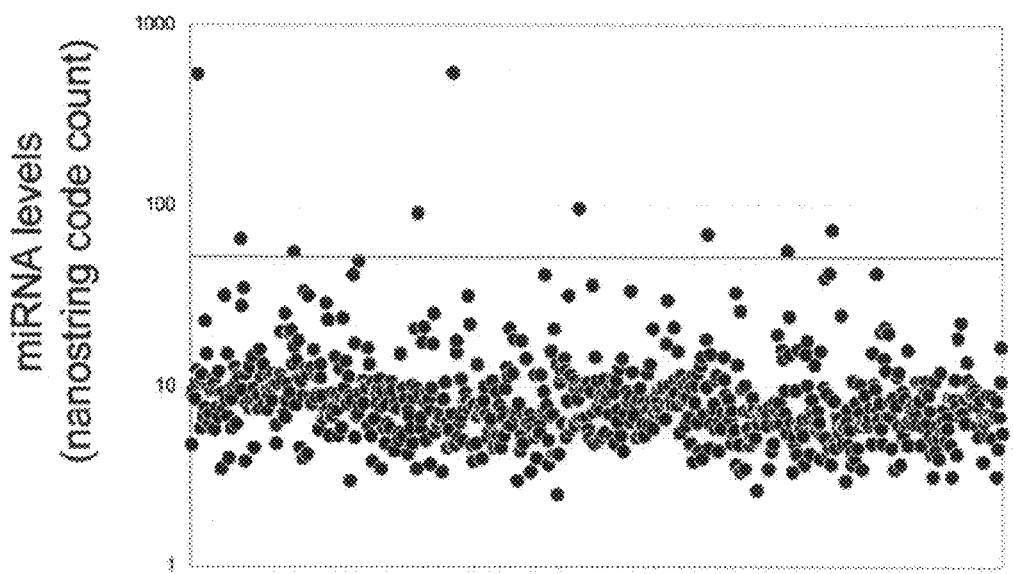
(FIG. 1A) Scatter plot representing the NanoString miRNA profile obtained from A-549 purified exosomes. The red line indicates the threshold of 50 code counts.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Described and applied herein is that tumor-secreted miR-21 and miR-29a can also function by binding as ligands to receptors of the Toll-like receptor family, murine TLR7 and human TLR8, in immune cells, triggering a TLR-mediated prometastatic inflammatory response, which ultimately can lead to tumor growth and metastasis. Thus, by acting as paracrine agonists of TLRs, secreted miRNAs are key regulators of the tumor microenvironment. This mechanism of action of miRNAs is implicated in the tumor-immune system communication, and is important in tumor growth and spread, therefore representing a new target for cancer treatment.

Shown herein is that miR-21 and 29a secreted by tumor cells in exosomes (also known as microvesicles), can bind to TLR8 (and TLR7) and activate these receptors in immune cells, leading to TLR-mediated NF-☐B activation and secretion of prometastatic inflammatory cytokines. It has been shown previously that tumor secretion of the extracellular matrix proteoglycan versican induces a pro-inflammatory response by activating TLR2:TLR6 complexes in myeloid cells. Shown herein is that tumor-secreted miRNAs also participate in the pro-tumoral inflammatory process, by activating the TLR8 response on immune cells. As a result, tumor cells tend to metastasize more, when this paracrine loop is intact. The inventors' data identify a miRNAs, miRNAs in exosomes, and exosomes as agonists of TLR receptor family, and show their effect on tumor-microenvironment and related interactions. Further, drugs affecting exosome secretion by cancer cells significantly reduce the metastatic potential of the cells, and this effect can be rescued by injecting tumor-bearing mice with exosomes secreted by the treated cells.

As used herein interchangeably, a "miR gene product," "microRNA," "miR," or "miRNA" refers to the unprocessed or processed RNA transcript from a miR gene. As the miR gene products are not translated into protein, the term "miR gene products" does not include proteins. The unprocessed miR gene transcript is also called a "miR precursor," and typically comprises an RNA transcript of about 70-100 nucleotides in length. The miR precursor can be processed by digestion with an RNAse (for example, Dicer, Argonaut, RNAse III (e.g., *E. coli* RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having to be processed from the miR precursor. When a microRNA is referred to herein by name, the name corresponds to both the precursor and mature forms, unless otherwise indicated.

In one aspect of the inventive subject matter, methods are described for analyzing a biological sample of a mammal in which exosomes are obtained from a living subject that include a plurality of distinct RNA molecules. The exosomes are then enriched and differentiated to produce a result based on one or more distinct RNA molecules. The RNA analysis may include analysis of a single RNA, of at least two distinct RNAs, or an entire RNA profile. The results are then correlated with a diagnosis (e.g., cancer or a clinical stage of a cancer, including pre-cancerous stages) or prognosis/ diagnosis of a condition of the subject.

As used herein, a "subject" can be any mammal that has, or is suspected of having, cancer. In a preferred embodiment, the subject is a human who has, or is suspected of having, cancer.

The level of at least one miR gene product can be measured in cells of a biological sample obtained from the subject. For example, a tissue sample can be removed from a subject suspected of having cancer, by conventional biopsy techniques. In another embodiment, a blood sample can be removed from the subject, and white blood cells can be isolated for DNA extraction by standard techniques. The blood or tissue sample is preferably obtained from the subject prior to initiation of radiotherapy, chemotherapy or other therapeutic treatment. A corresponding control tissue or blood sample, or a control reference sample, can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of miR gene product produced from a given miR gene in cells from the subject's sample can be compared to the corresponding miR gene product levels from cells of the control sample. Alternatively, a reference sample can be obtained and processed separately (e.g., at a different time) from the test sample and the level of a miR gene product produced from a given miR gene in cells from the test sample can be compared to the corresponding miR gene product level from the reference sample.

The relative miR gene expression in the control and normal samples can be determined with respect to one or more RNA expression standards. The standards can comprise, for example, a zero miR gene expression level, the miR gene expression level in a standard cell line, the miR gene expression level in unaffected tissues of the subject, or the average level of miR gene expression previously obtained for a population of normal human controls. For example, the control may be a database with mean miR expression levels in tumor samples from many patient samples, or a primary tumor sample miR expression, from the subject with suspected metastasis, or a primary tumor sample from another subject having primary cancer of the same type. "Control" therefore may reflect a comparison amongst tumor cell types, eg. primary v. metastatic, or normal v. cancerous. The control may be a known disease state. The control comparison may be made with regard to another point in time, for instance: a prior healthy tissue sample, a pre-diagnosis sample, a post-diagnosis sample, a sample prior to treatment, a sample during remission, and/or a sample at a different cancer stage.

The level of a miR gene product in a sample can be measured using any technique that is suitable for detecting RNA expression levels in a biological sample. Suitable techniques (e.g., Northern blot analysis, RT-PCR, in situ hybridization) for determining RNA expression levels in a biological sample (e.g., cells, tissues) are well known to those of skill in the art. In a particular embodiment, the level of at least one miR gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes (e.g., DNA probes, RNA probes) for Northern blot hybridization of a given miR gene product can be produced from the nucleic acid sequences provided herein and include, but are not limited to, probes having at least about 70%, 75%, 80%, 85%, 90%, 95%, 98% or 99% complementarity to a miR gene product of interest, as well as probes that have complete complementarity to a miR gene product of interest. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference.

For example, the nucleic acid probe can be labeled with, e.g., a radionuclide, such as $^3H$, $^{32}P$, $^{33}P$, $^{14}C$, or $^{35}S$; a heavy metal; a ligand capable of functioning as a specific binding pair member for a labeled ligand (e.g., biotin, avidin or an antibody); a fluorescent molecule; a chemiluminescent molecule; an enzyme or the like.

Probes can be labeled to high specific activity by either the nick translation method of Rigby et al. (1977), J. Mol. Biol. 113:237-251 or by the random priming method of Fienberg et al. (1983), Anal. Biochem. 132:6-13, the entire disclosures of which are incorporated herein by reference. The latter is the method of choice for synthesizing $^{32}$P-labeled probes of high specific activity from single-stranded DNA or from RNA templates. For example, by replacing preexisting nucleotides with highly radioactive nucleotides according to the nick translation method, it is possible to prepare $^{32}$P-labeled nucleic acid probes with a specific activity well in excess of $10^8$ cpm/microgram.

Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such as the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyfide-oxyuridine triphosphate, into the probe molecule. The biotinylated probe oligonucleotide can be detected by reaction with biotin-binding proteins, such as avidin, streptavidin and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miR gene product can be produced from the nucleic acid sequences provided herein, and include, but are not limited to, probes having at least about 70%, 75%, 80%, 85%, 90%, 95%, 98% or 99% complementarity to a miR gene product of interest, as well as probes that have complete complementarity to a miR gene product of interest, as described above.

The relative number of miR gene transcripts in cells can also be determined by reverse transcription of miR gene transcripts, followed by amplification of the reverse-transcribed transcripts by polymerase chain reaction (RT-PCR). The levels of miR gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). Methods for performing quantitative and semi-quantitative RT-PCR, and variations thereof, are well known to those of skill in the art.

In some instances, it may be desirable to simultaneously determine the expression level of a plurality of different miR gene products in a sample. In other instances, it may be desirable to determine the expression level of the transcripts of all known miR genes correlated with a cancer. Assessing cancer-specific expression levels for hundreds of miR genes or gene products is time consuming and requires a large amount of total RNA (e.g., at least 20 µg for each Northern blot) and autoradiographic techniques that require radioactive isotopes.

To overcome these limitations, an oligolibrary, in microchip format (i.e., a microarray), may be constructed containing a set of oligonucleotide (e.g., oligodeoxynucleotide) probes that are specific for a set of miR genes. Using such a microarray, the expression level of multiple microRNAs in a biological sample can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microRNAs have an altered expression level in cancer metastasis and/or recurrence cells. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for a miR" is meant a probe oligonucleotide that has a sequence selected to hybridize to a specific miR gene product, or to a reverse transcript of the specific miR gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue may be distinguished from cancer cells, and within cancer cell types, different prognosis states (for example, good or poor long term survival prospects) may be determined By comparing expression profiles of cells in different states, information regarding which genes are important (including both up- and down-regulation of genes) in each of these states is obtained. The identification of sequences that are differentially expressed in cancer cells or normal cells, as well as differential expression resulting in different prognostic outcomes, allows the use of this information in a number of ways. For example, a particular treatment regime may be evaluated (e.g., to determine whether a chemotherapeutic drug acts to improve the long-term prognosis in a particular patient) Similarly, diagnosis may be done or confirmed by comparing patient samples with known expression profiles. Furthermore, these gene expression profiles (or individual genes) allow screening of drug candidates that suppress the miR or disease expression profile or convert a poor prognosis profile to a better prognosis profile.

A microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs and other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75×TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample. According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 µg of total RNA. The relatively limited number of miRNAs (a few hundred per species) allows the construction of a common microarray for several species, with distinct oligonucleotide probes for each. Such a tool would allow for analysis of trans-species expression for each known miR under various conditions.

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having a cancer profile (eg. metastasis or recurrence) is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal, e.g., noncancerous, control sample. The signal is indicative of the presence of, or propensity to develop, the cancer profile in the subject.

Other techniques for measuring miR gene expression are also within the skill in the art, and include various techniques for measuring rates of RNA transcription and degradation.

Embodiments of the invention also provide methods of determining the prognosis. Examples of an adverse prognosis include, but are not limited to, low survival rate and rapid disease progression.

In certain embodiments, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

Accordingly, embodiments of the present invention encompass methods of treating cancer in a subject. The method comprises administering an effective amount of the at least one isolated antisense miR gene product, or an isolated variant or biologically-active fragment thereof, such that metastasis, recurrence or proliferation of cancer cells in the subject is inhibited. The isolated antisense miR gene product that is administered to the subject can be complementary to an identical to an endogenous wild-type miR gene product or it can be complementary a variant or biologically-active fragment thereof.

As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of a cellular process associated with metastasis or recurrence (e.g., cell differentiation, cell growth, cell death). These variants include species variants and variants that are the consequence of one or more mutations (e.g., a substitution, a deletion, an insertion) in a miR gene. In certain embodiments, the variant is at least about 70%, 75%, 80%, 85%, 90%, 95%, 98%, or 99% identical to a corresponding wild-type miR gene product.

As defined herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of a cellular process associated with cancer metastasis or recurrence. In certain embodiments, the biologically-active fragment is at least about 5, 7, 10, 12, 15, or 17 nucleotides in length. In a particular embodiment, an isolated miR gene product can be administered to a subject in combination with one or more additional anti-cancer treatments. Suitable anti-cancer treatments include, but are not limited to, chemotherapy, radiation therapy and combinations thereof (e.g., chemoradiation).

The terms "treat", "treating" and "treatment", as used herein, refer to ameliorating symptoms associated with a disease or condition, for example, lung cancer metastasis and/or recurrence, including preventing or delaying the onset of the disease symptoms, and/or lessening the severity or frequency of symptoms of the disease or condition. The terms "subject" and "individual" are defined herein to include animals, such as mammals, including, but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

A locked nucleic acid (LNA), sometimes referred to as inaccessible RNA, is a modified RNA nucleotide/oligonucleotide. The ribose moiety of an LNA nucleotide is modified with an extra bridge connecting the 2' oxygen and 4' carbon. The bridge "locks" the ribose in the 3'-endo conformation. LNA nucleotides can be mixed with DNA or RNA residues in the oligonucleotide when desired. Such oligomers are synthesized chemically and are commercially available.

As used herein, an "effective amount" of an isolated miR gene product is an amount sufficient to inhibit proliferation of a cancer cell in a subject suffering from cancer metastasis and/or recurrence. One skilled in the art can readily determine an effective amount of a miR gene product to be administered to a given subject, by taking into account factors, such as the size and weight of the subject; the extent of disease penetration; the age, health and sex of the subject; the route of administration; and whether the administration is regional or systemic.

For example, an effective amount of an isolated miR gene product can be based on the approximate weight of a tumor mass to be treated. The approximate weight of a tumor mass can be determined by calculating the approximate volume of the mass, wherein one cubic centimeter of volume is roughly equivalent to one gram. An effective amount of the isolated miR gene product based on the weight of a tumor mass can be in the range of about 10-500 micrograms/gram of tumor mass. In certain embodiments, the tumor mass can be at least about 10 micrograms/gram of tumor mass, at least about 60 micrograms/gram of tumor mass or at least about 100 micrograms/gram of tumor mass.

An effective amount of an isolated miR gene product can also be based on the approximate or estimated body weight of a subject to be treated. Preferably, such effective amounts are administered parenterally or enterally, as described herein. For example, an effective amount of the isolated miR gene product that is administered to a subject can range from about 5-3000 micrograms/kg of body weight, from about 700-1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

As used herein, an "isolated" miR gene product is one that is synthesized, or altered or removed from the natural state through human intervention. For example, a synthetic miR gene product, or a miR gene product partially or completely separated from the coexisting materials of its natural state, is considered to be "isolated." An isolated miR gene product can exist in a substantially-purified form, or can exist in a cell into which the miR gene product has been delivered. Thus, a miR gene product that is deliberately delivered to, or expressed in, a cell is considered an "isolated" miR gene product. A miR gene product produced inside a cell from a miR precursor molecule is also considered to be an "isolated" molecule. According to embodiments of the invention, the isolated miR gene products described herein can be used for the manufacture of a medicament for treating cancer metastasis and/or recurrence in a subject (e.g., a human). As used herein, a miR gene product may broadly include an anti-miR or antisense, partial or complete, complement of an identified miR.

Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of embodiments of the invention can also comprise inducible or regulatable promoters for expression of the miR gene products in cancer cells.

The miR gene products that are expressed from recombinant plasmids can be isolated from cultured cell expression systems by standard techniques. The miR gene products that are expressed from recombinant plasmids can also be delivered to, and expressed directly in, the cancer cells. The use of recombinant plasmids to deliver the miR gene products to cancer cells is discussed in more detail below.

The miR gene products can be expressed from a separate recombinant plasmid, or they can be expressed from the same recombinant plasmid. In one embodiment, the miR gene products are expressed as RNA precursor molecules from a single plasmid, and the precursor molecules are processed into the functional miR gene product by a suitable processing system, including, but not limited to, processing systems extant within a cancer cell. Other suitable processing systems include, e.g., the in vitro *Drosophila* cell lysate system (e.g., as described in U.S. Published Patent Application No. 2002/0086356 to Tuschl et al., the entire disclosure of which is incorporated herein by reference) and the *E. coli* RNAse III system (e.g., as described in U.S. Published Patent Application No. 2004/0014113 to Yang et al., the entire disclosure of which is incorporated herein by reference).

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296:550-553; Miyagishi et al. (2002), Nat. Biotechnol. 20:497-500; Paddison et al. (2002), Genes Dev. 16:948-958; Lee et al. (2002), Nat. Biotechnol. 20:500-505; and Paul et al. (2002), Nat. Biotechnol. 20:505-508, the entire disclosures of which are incorporated herein by reference.

In one embodiment, a plasmid expressing the miR gene products comprises a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cancer cells. The use of recombinant viral vectors to deliver the miR gene products to cancer cells is discussed in more detail below.

The recombinant viral vectors of embodiments of the invention comprise sequences encoding the miR gene products and any suitable promoter for expressing the RNA sequences. Suitable promoters include, but are not limited to, the U6 or H1 RNA pol III promoter sequences, or the cytomegalovirus promoters. Selection of other suitable promoters is within the skill in the art. The recombinant viral vectors of embodiments of the invention can also comprise inducible or regulatable promoters for expression of the miR gene products in a cancer cell.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of embodiments of the invention can be pseudotyped with surface proteins from vesicular stomatitis virus (VSV), rabies, Ebola, Mokola, and the like. AAV vectors of embodiments of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, J. E., et al. (2002), J. Virol. 76:791-801, the entire disclosure of which is incorporated herein by reference.

Selection of recombinant viral vectors suitable for use in embodiments of the invention, methods for inserting nucleic acid sequences for expressing RNA into the vector, methods of delivering the viral vector to the cells of interest, and recovery of the expressed RNA products are within the skill in the art. See, for example, Dornburg (1995), Gene Therap. 2:301-310; Eglitis (1988), Biotechniques 6:608-614; Miller (1990), Hum. Gene Therap. 1:5-14; and Anderson (1998), Nature 392:25-30, the entire disclosures of which are incorporated herein by reference.

Particularly suitable viral vectors are those derived from AV and AAV. A suitable AV vector for expressing the miR gene products, a method for constructing the recombinant AV vector, and a method for delivering the vector into target cells, are described in Xia et al. (2002), Nat. Biotech. 20:1006-1010, the entire disclosure of which is incorporated herein by reference. Suitable AAV vectors for expressing the miR gene products, methods for constructing the recombinant AAV vector, and methods for delivering the vectors into target cells are described in Samulski et al. (1987), J. Virol. 61:3096-3101; Fisher et al. (1996), J. Virol., 70:520-532; Samulski et al. (1989), J. Virol. 63:3822-3826; U.S. Pat. No. 5,252,479; U.S. Pat. No. 5,139,941; International Patent Application No. WO 94/13788; and International Patent Application No. WO 93/24641, the entire disclosures of which are incorporated herein by reference. In one embodiment, the miR gene products are expressed from a single recombinant AAV vector comprising the CMV intermediate early promoter.

In a certain embodiment, a recombinant AAV viral vector comprises a nucleic acid sequence encoding a miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

The number of cancer cells in the body of a subject can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

A miR gene product can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the tumor.

In the present methods, a miR gene product can be administered to the subject either as naked RNA, in combination with a delivery reagent, or as a nucleic acid (e.g., a recombinant plasmid or viral vector) comprising sequences that express the miR gene product or miR gene expression-inhibiting compound. Suitable delivery reagents include, e.g., the Mirus Transit TKO lipophilic reagent; LIPOFECTIN; lipofectamine; cellfectin; polycations (e.g., polylysine) and liposomes.

Recombinant plasmids and viral vectors comprising sequences that express the miR gene products and techniques for delivering such plasmids and vectors to cancer cells, are discussed herein and/or are well known in the art.

In a particular embodiment, liposomes are used to deliver a miR gene product (or nucleic acids comprising sequences encoding them) to a subject. Liposomes can also increase the blood half-life of the gene products or nucleic acids. Suitable liposomes for use in embodiments of the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al. (1980), Ann. Rev. Biophys. Bioeng. 9:467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to cancer cells. Ligands that bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome can comprise both an opsonization-inhibition moiety and a ligand.

Opsonization-inhibiting moieties for use in preparing the liposomes are typically large hydrophilic polymers that are bound to the liposome membrane. As used herein, an opsonization-inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization-inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) or derivatives thereof; e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization-inhibiting polymer can be a block copolymer of PEG and either a polyamino acid, polysaccharide, polyamidoamine, polyethyleneamine, or polynucleotide. The opsonization-inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or a derivative thereof. Liposomes modified with PEG or PEG-derivatives are sometimes called "PEGylated liposomes."

The opsonization-inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example, solid tumors (e.g., lung cancer metastasis and/or recurrences), will efficiently accumulate these liposomes; see Gabizon, et al. (1988), Proc. Natl. Acad. Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products (or nucleic acids comprising sequences encoding them) to tumor cells.

The miR gene products can be formulated as pharmaceutical compositions, sometimes called "medicaments," prior to administering them to a subject, according to techniques known in the art. Accordingly, embodiments of the invention encompass pharmaceutical compositions for treating cancer metastasis and/or recurrence. In one embodiment, the pharmaceutical composition comprises at least one isolated miR gene product, or an isolated variant or biologically-active fragment thereof, and a pharmaceutically-acceptable carrier.

EXAMPLES

Identification of Specific miRNAs Released in Cancer Cell-Derived Exosomes.

Figure 11A:
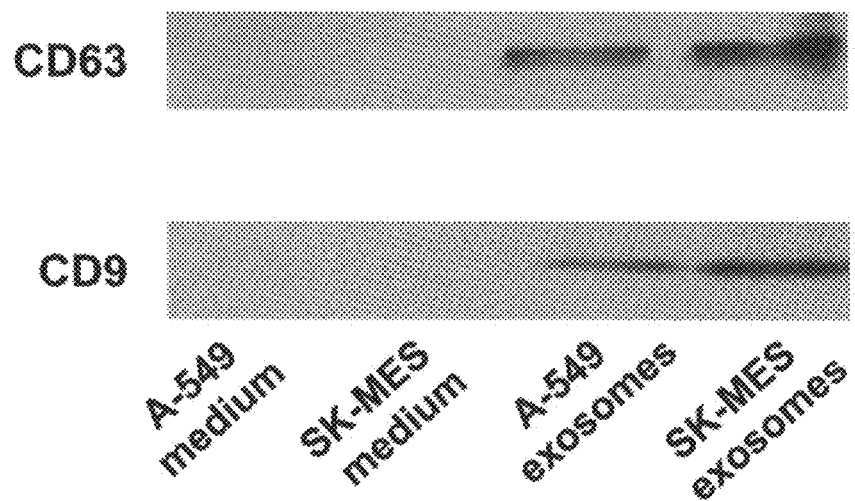
(FIG. 11A) Immunoblotting for CD9 and CD63 showing that the purified fractions from the supernatants of A-549 and SK-MES are enriched in CD9 and CD63 proteins, two well known markers of exosomes.

To identify which miRNAs are present in tumor-secreted exosomes, exosomes were isolated from the supernatant of A-549 and SK-MES lung cancer cell lines. First, the purified supernatant exosome fraction was assessed for enrichment in CD9 and CD63, two known exosome markers (FIG. 11A). By performing NanoString analysis, it was observed that nine miRNAs (miR-16, -21, -27b, -29a, -133a, -193a-3p, -544, -563, and -1283) were present in exosomes derived from both cell lines at an expression level higher than 50 code counts (FIG. 1A).

TABLE 1

NanoString code count for miRNAs contained in exosomes secreted by A-549 and SK-MES lung cancer cell lines, and whose code count is above 50.

|  | A-549 code count | SK-MES code count |
| --- | --- | --- |
| miR-133a | 528.2 | 766.3 |
| miR-193a-3p | 65.8 | 107.8 |
| miR-29a | 50.3 | 63.0 |
| miR-21 | 92.2 | 173.3 |
| miR-27b | 540.3 | 992.5 |
| miR-16 | 96.8 | 145.8 |
| miR-544 | 70.5 | 151.0 |
| miR-1283 | 57.0 | 110.3 |
| miR-563 | 74.7 | 130.8 |

Figure 1B:
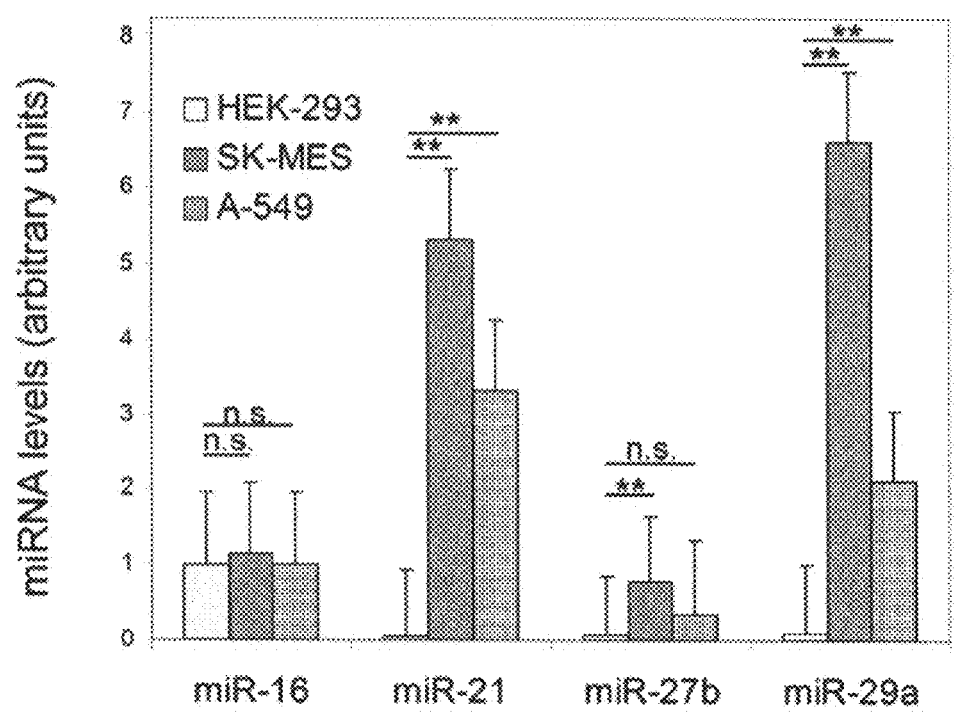
(FIG. 1B) Validation of the NanoString results in A-549 and SK-MES purified exosomes compared with HEK-293 purified vesicles by quantitative real-time PCR. The experiments were conducted in hextuplicate; results are presented as average±SD. **$P<0.0001$.

To validate these data, we performed quantitative real-time PCR for all nine miRNAs (plus miR-15a as a negative control), using the same exosome-derived RNAs from A-549 and SK-MES and RNA derived from exosomes purified from the supernatant of HEK-293 cells. We confirmed that miR-15a expression was not detectable in the exosomes of any of the three cell lines and that the expression of miR-16 was not significantly different among the three cell lines (FIG. 1B). However, the expression of miR-21, -27b, and -29a was significantly higher in exosomes derived from A-549 and SK-MES cells than in exosomes from HEK-293 cells (P<0.001), suggesting a cancer-specific pattern of secreted miRNAs (FIG. 1B). The NanoString expression data for miR-133a, -193a-3p, -544, -563, and -1283 were not confirmed by quantitative real-time PCR.

MiRNAs in Cancer-Released Exosomes Can Reach and Bind TLRs.

Figure 2A:
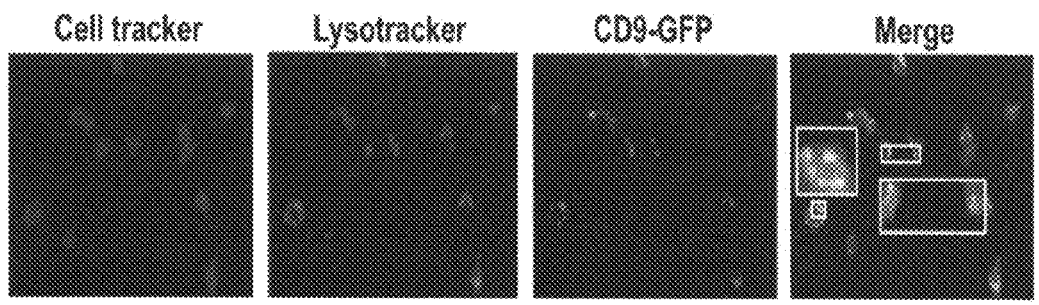
(FIG. 2A) Confocal images of RAW 264.7 cells stained with cell tracker (blue) and with LysoTracker endosome marker (red) and cocultured with HEK-293-secreted CD9-GFP exosomes (green). Colocalization is indicated in yellow (merged image).
Figure 2B:
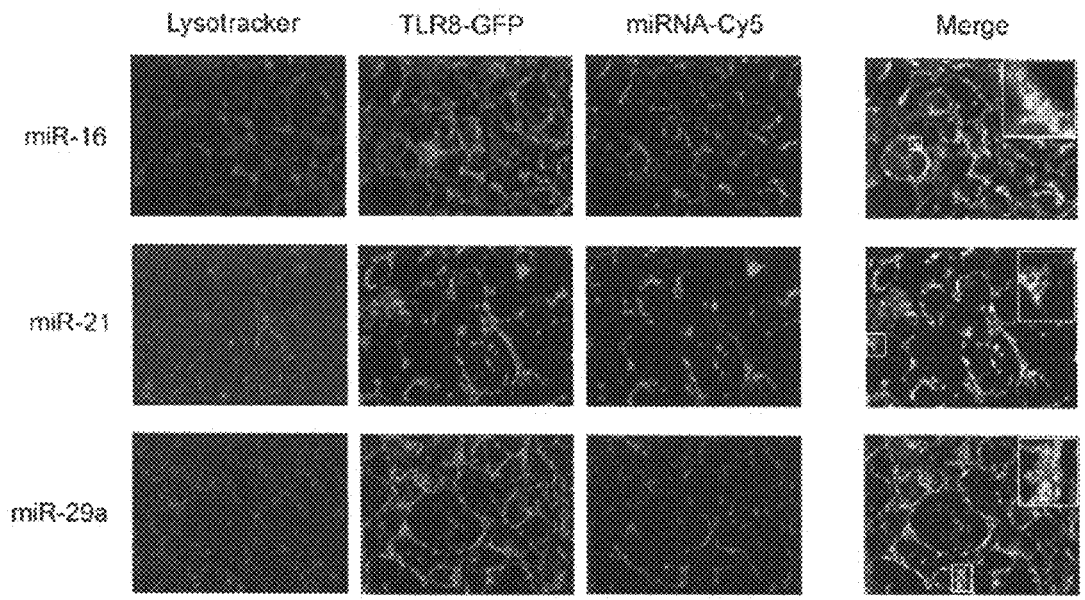
(FIG. 2B) Confocal images of HEK-293 cells cotransfected with endosome LysoTracker (blue), GFP-tagged TLR8 (TLR8-GFP) (green), and Cy5-conjugated mature miRNAs (miRNA-Cy5) (red). Colocalization is indicated in yellow (merged image).
Figure 2C:
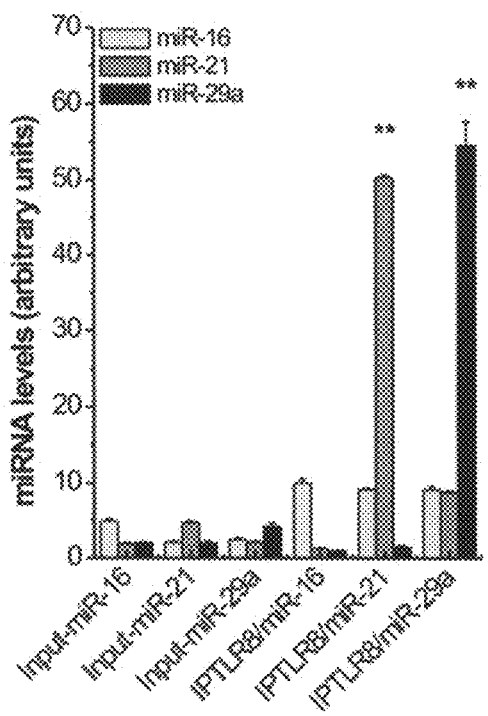
(FIG. 2C) Levels of miR-16, miR-21, and miR-29a in the coimmunoprecipitates for TLR8 (IPTLR8/miR-16, IPTLR8/miR-21, and IPTLR8/miR-29a, respectively) in TLR8-HEK-293 cells detected by quantitative real-time PCR. Results are shown as means±SD. **$P<0.001$.
Figure 2D:
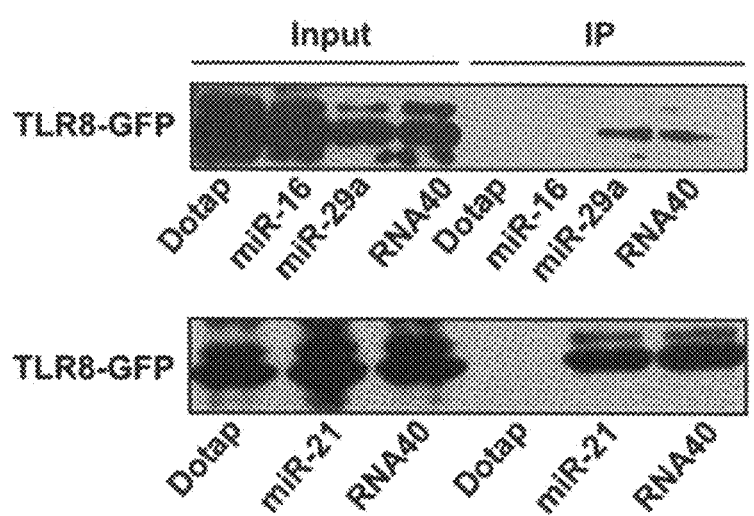
(FIG. 2D) Immunoblotting with anti-GFP antibody for TLR8-GFP complex performed on immunoprecipitates derived from TLR8-GFP-HEK-293 cells.
Figure 2E:
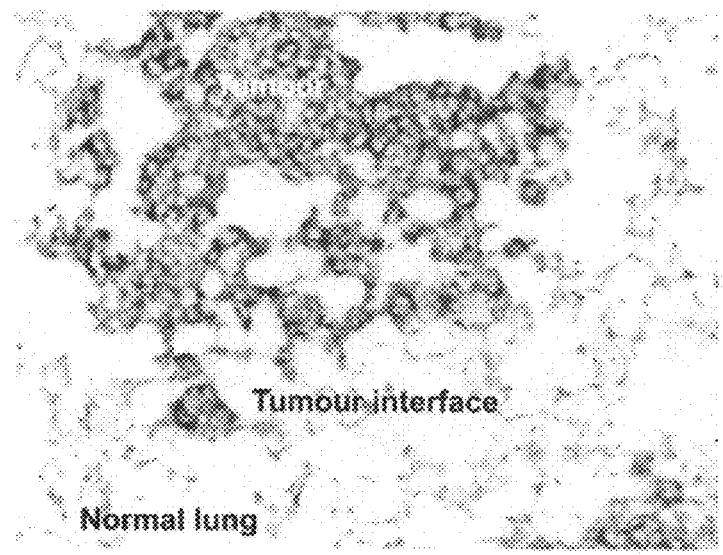
(FIG. 2E) LNA-ISH for miR-29a (blue) performed on mice tumors.
Figure 2F:
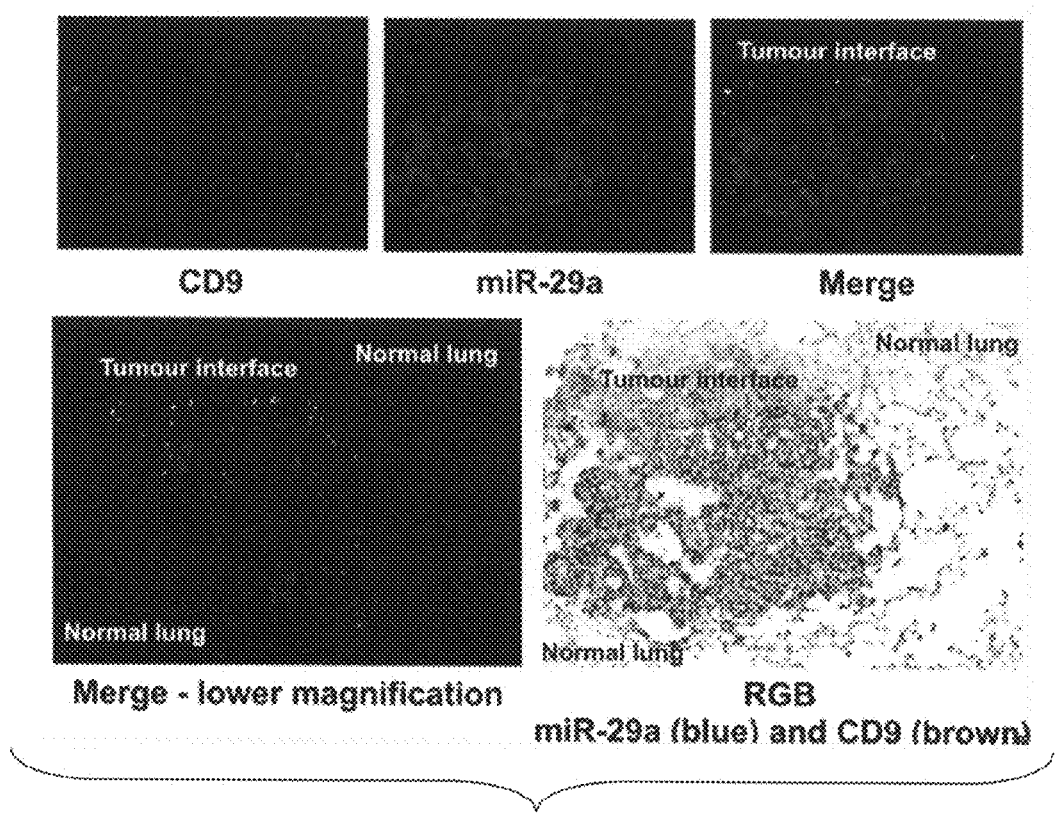
(FIG. 2F) (Upper) ISH of CD9 (red) and miR-29a (blue) in mouse tumors. Coexpression is indicated in yellow (merged image). (Lower Left) Merged image with lower magnification indicates coexpression of CD9 and miR-29a at the tumor interface. (Lower Right) Corresponding red/green/blue image (miR-29a is stained in blue and CD9 in brown).
Figure 11B:
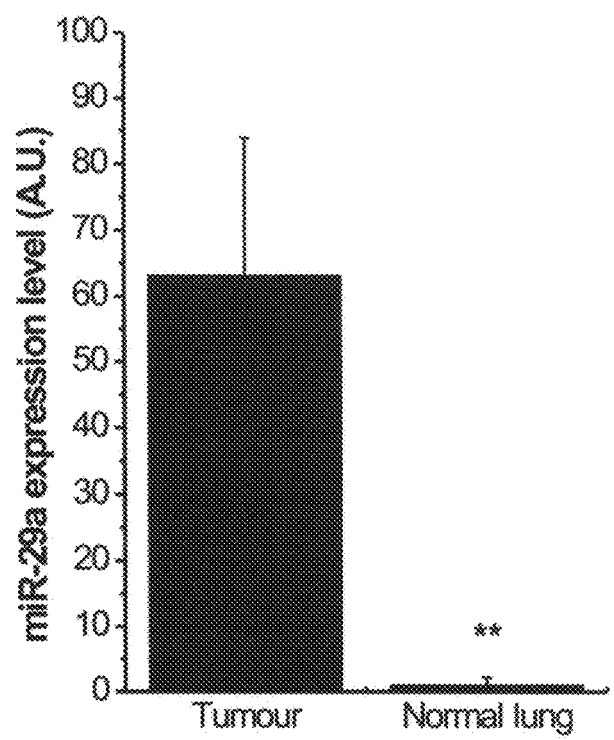
(FIG. 11B) Statistical analysis performed on mouse tumor samples processed for in situ hybridization for miR-29a. Cancer cells were considered positive for miR-29a when their blue signal was at least 5 fold greater than the background stain as measured by the Nuance system. miR-29 positive cancer cells were counted in multiple 200× fields for the different slides tested, then mean±s.d. were determined by using InStat software. **, P<0.005.
Figure 12A:
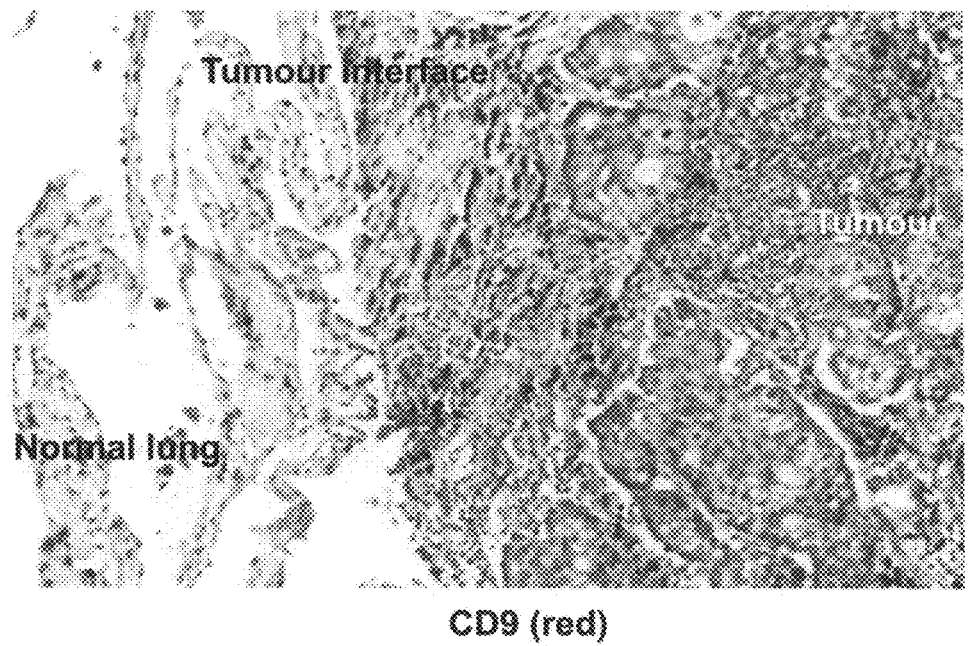
(FIG. 12A) ISH for exosomal marker CD9 performed on human lung cancer samples. The arrow depicts cells highly enriched in CD9, stained in red, at the tumor interface. In blue is haematoxylin counterstain.
Figure 12B:
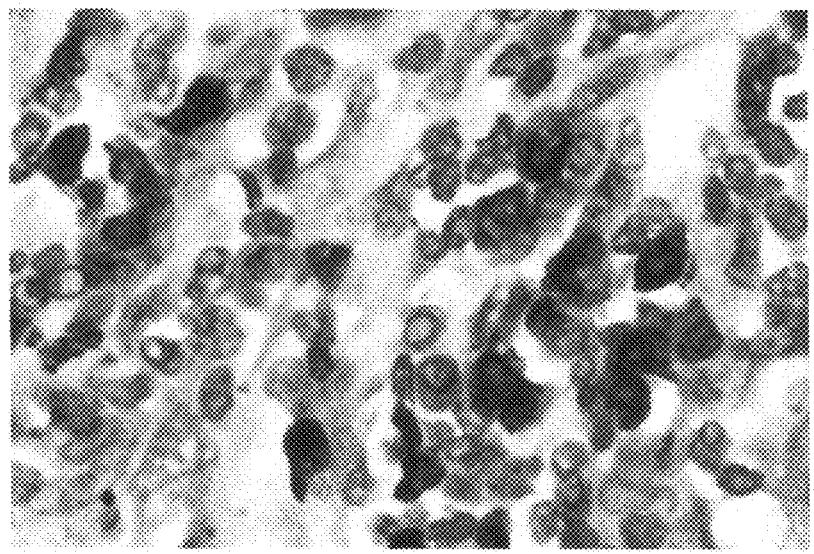
(FIG. 12B) Higher magnification of tumor interface in human lung cancer sample as seen in panel A. CD9 is mainly located in cells that display the oval/folded nuclei and ample cytoplasm features typical of macrophages.
Figure 13A:
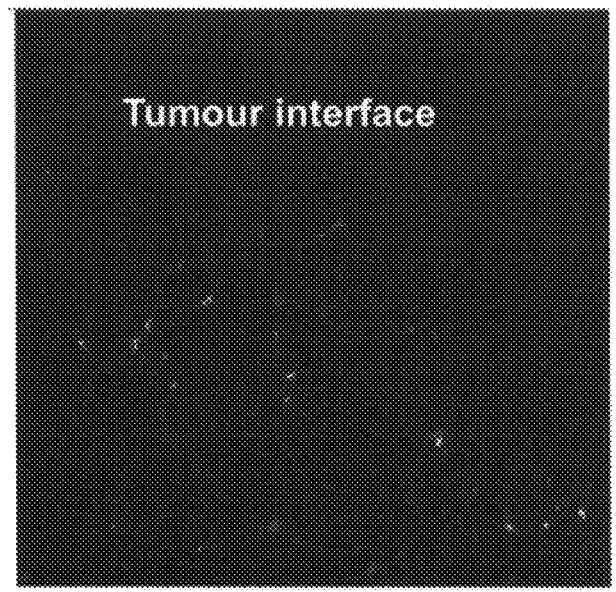
(FIG. 13A) LNA-ISH performed on mouse tumor showing that miR-29a and macrophage marker F-11 are co-expressed only at the level of tumor interface but not in the adjacent normal lung. The Nuance-converted image depicts miR-29a as fluorescent blue and F-11 as fluorescent green, while fluorescent yellow indicates their co-expression.
Figure 13B:
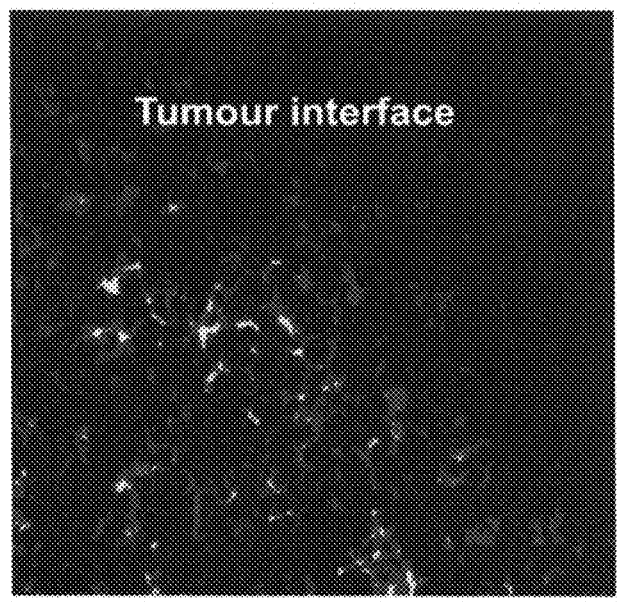
(FIG. 13B) Mouse tumors were stained for miR-29a LNA-ISH and the cancer-associated epithelial marker cytokeratin AE1/3. Cells positive for miR-29a (fluorescent blue) co-localize with cytokeratin only in the tumor (fluorescent yellow), but not in the tumor interface, where there are cells miR-29a positive and cytokeratin negative.
Figure 13C:
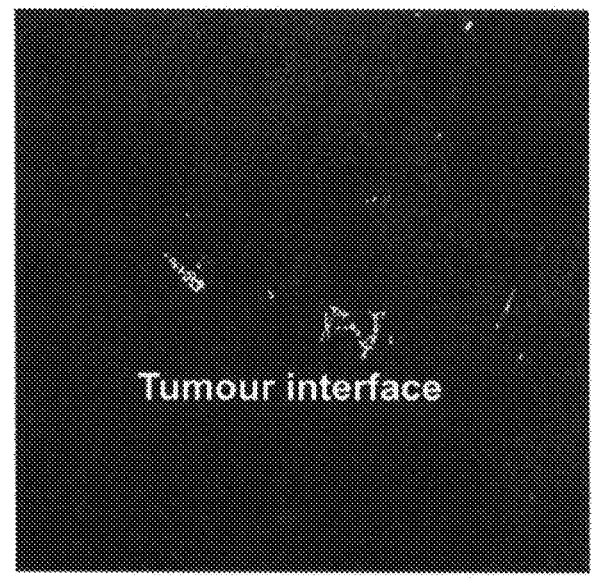
(FIG. 13C) LNA-ISH of miR-29a and TLR7 on a mouse tumor. The Nuance-converted image shows miR-29a as fluorescent blue and TLR7 as fluorescent green. Their co-expression is indicated by fluorescent yellow signal.

Because both murine TLR7 and human TLR8 are located in intracellular endosomes, an initial inquiry was made as to whether cell-released exosomes are able to reach TLR-containing endosomes in a "receiving" cell. Therefore, cocultured HEK-293 cells previously transfected with a plasmid encoding a CD9 exosome marker conjugated with GFP with RAW 264.7 murine macrophages stained with a vital blue cell tracker, in which TLR-containing endosomes also were labeled with red LysoTracker. It was observed that RAW macrophages incorporated CD9-GFP exosomes released by HEK-293 cells, and these exosomes colocalized with endosomes in RAW cells (FIG. 2A). Next, we asked whether extracellular miR-16, -21, and -29a can reach TLR8 within intracellular endosomes. To this aim, Dotap liposomal formulations of the miRNAs of interest was used (mimicking the exosomes in which they are enclosed). HEK-293 cells, which do not express TLR8, were transfected with a plasmid expressing GFP-tagged TLR8 protein. After 48 h, cells were treated with a Dotap liposome formulation containing Cy5-conjugated mature miR-16, -21, or -29a, and then blue LysoTracker was added to the culture medium to label cellular endosomes. Colocalization of miRNA, TLR8, and endosomes was detected for all three miRNAs (FIG. 2B), showing that exogenous miRNAs can reach TLR8 in cellular endosomes. To determine whether these miRNAs bind to TLR8, we performed coimmunoprecipitation assays for TLR8 in HEK-293 cells expressing GFP-TLR8 and treated with Dotap-miR-16, Dotap-miR-21, Dotap-miR-29a, or Dotap alone and determined miRNA levels by quantitative real-time PCR. Although miR-16 was almost undetectable in the GFP-TLR8 coimmunoprecipitate, miR-21 and miR-29a expression was highly enriched (>50-fold) (FIG. 2C). Also treated were HEK-293 cells expressing GFP-TLR8 with Dotap alone or with Dotap formulations of 5'-biotinylated miR-16, -21, or -29a. As a positive control, cells were treated with 5'-biotinylated ssRNA40, a 20mer ssRNA previously shown to activate TLR8. After coimmunoprecipitation of miRNAs and ssRNA40, TLR8 was detected in the ssRNA40-, miR-21-, and -29a-treated cells (FIG. 2D) but not in the cells treated with Dotap alone or with Dotap-miR-16. To investigate whether this interaction also occurs in vivo, we injected B6 mice with Lewis lung carcinoma (LLC) cells, which tend to localize to the lung after injection into the tail, and analyzed lung tumors 15 d after injection. By ISH we showed that miR-29a is produced by cancer cells and not by cells in the adjacent normal lung tissue (FIG. 2E and FIG. 11B). These findings also were confirmed in samples of human primary lung cancer, where an enrichment of the exosome marker CD9 also was observed in macrophages at the tumor-normal tissue interface (FIG. 12). Also, by locked nucleic acid in situ hybridization (LNA ISH) it was observed that miR-29a and exosomes colocalized at the tumor-normal tissue interface in samples of mouse and human lung cancer (FIG. 2F), but not in normal tissue, at distance 1 mm from the tumor. Also, we showed that, although miR-29a colocalized with the cancer-associated epithelial marker cytokeratin in the center of the tumor (confirming that cancer cells are the main producers of miR-29a), at the periphery of tumor miR-29a is coexpressed with the macrophage marker F-11, but not cytokeratin, suggesting that miR-29a is present in macrophages at the tumor interface (FIGS. 13A and 13B). We also showed that miR-29a colocalized with TLR7 of the macrophages at the tumor interface (FIG. 13C). Overall, these data indicate that cancer cells secrete miR-29a in exosomes and that this miRNA colocalizes with TLR7 and TLR8 in macrophages at the tumor-normal tissue interface.

MiRNAs in Cancer-Released Exosomes Functionally Activate TLRs.

Figure 14A:
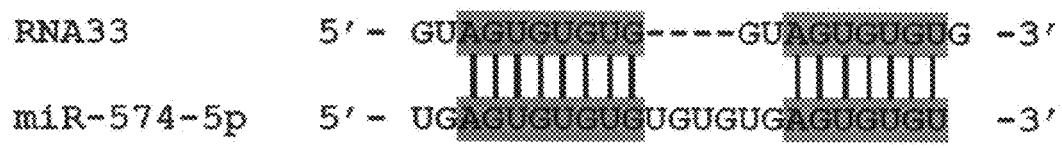
(FIG. 14A) BLAST analysis showing the similarity between the sequences of mature miR-147 (SEQ ID NO: 3) and 574-5p (SEQ ID NO: 2) with that of RNA33 (SEQ ID NO: 1). RNA33 corresponds to a GU-rich oligonucleotide which has been demonstrated to induce the secretion of cytokines in human and murine immune cells via human TLR8 and murine TLR7, respectively. The exact matching bases are highlighted in red.
Figure 14A:
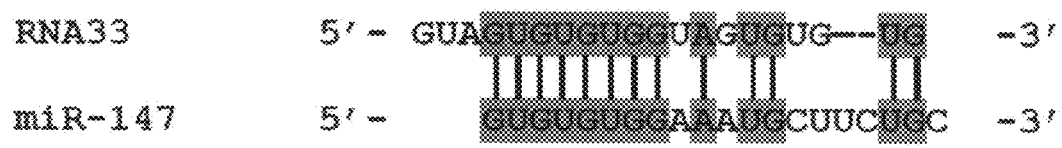

Experiments were performed to determine whether the miRNA-TLR interaction is functional, and assessed whether the miRNAs of interest induce the secretion of cytokines such as TNF-α and IL-6, whose production is increased by TLR activation. We isolated peritoneal macrophages from WT and TLR7$^{-/-}$ B6 mice. Cells were treated with Dotap alone or with Dotap formulations of miR-16, -21, -29a, and -147, and an ELISA for TNF-α and IL-6 was performed. In the functional assays, included also were miR-147 and -574-5p, because they have a mature viral-derived sequence that induces cytokine production through the activation of TLR8 and TLR7, similar to that of RNA33 (FIG. 14A). Although Dotap alone and Dotap-miR-16 did not induce cytokine secretion, miR-21, -29a, and -147 increased TNF-α and IL-6 production in WT but not in TLR7$^{-/-}$ mice (FIGS. 3 A and B). We also treated spleen cells from WT and TLR7$^{-/-}$ mice with the same miRNAs and assessed expression of CD69, an early activation marker of cells which has a role in inflammation and proliferation and which also is activated by TLR3. Polyinosinic:polycytidylic acid [poly (I:C)], a known agonist of TLR3, served as positive control. Cytofluorimetry showed that miR-21, -29a, and -147, but not miR-16 or Dotap alone, induced CD69 activation in spleen cells from WT but not TLR7$^{-/-}$ mice (FIGS. 3C and 3D), indicating that these miRNAs induce a TLR7-mediated spleen cell activation.

Figure 3A:
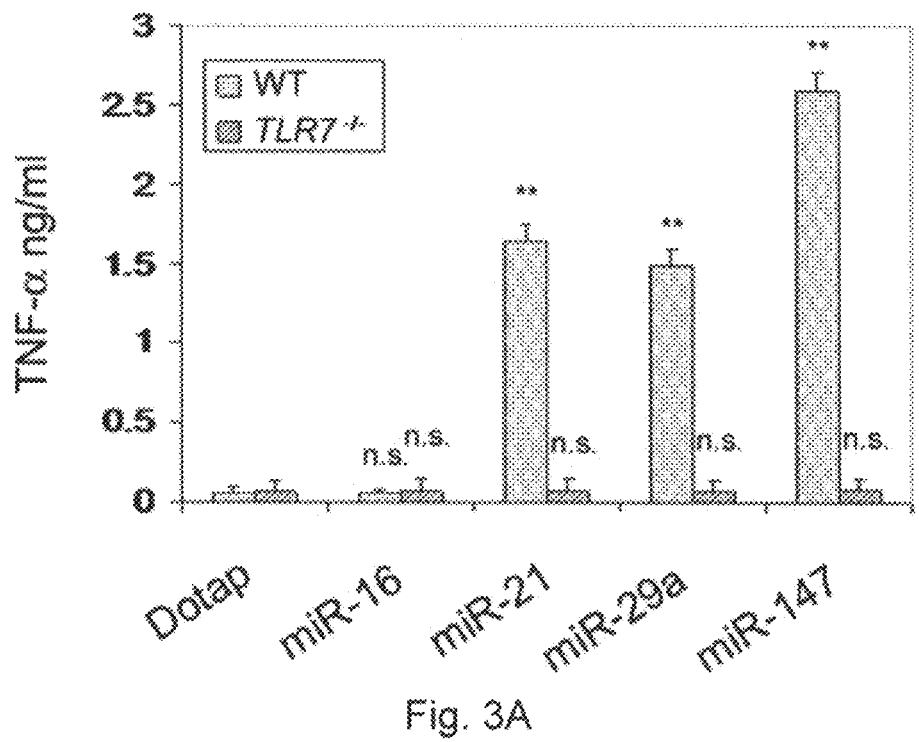
(FIG. 3A and FIG. 3B) ELISA for TNF-α (FIG. 3A) and IL-6 (FIG. 3B) performed on peritoneal macrophages isolated from WT (n=4) and TLR7$^{-/-}$ (n=4) mice and treated with Dotap formulations of the indicated miRNAs.
Figure 3B:
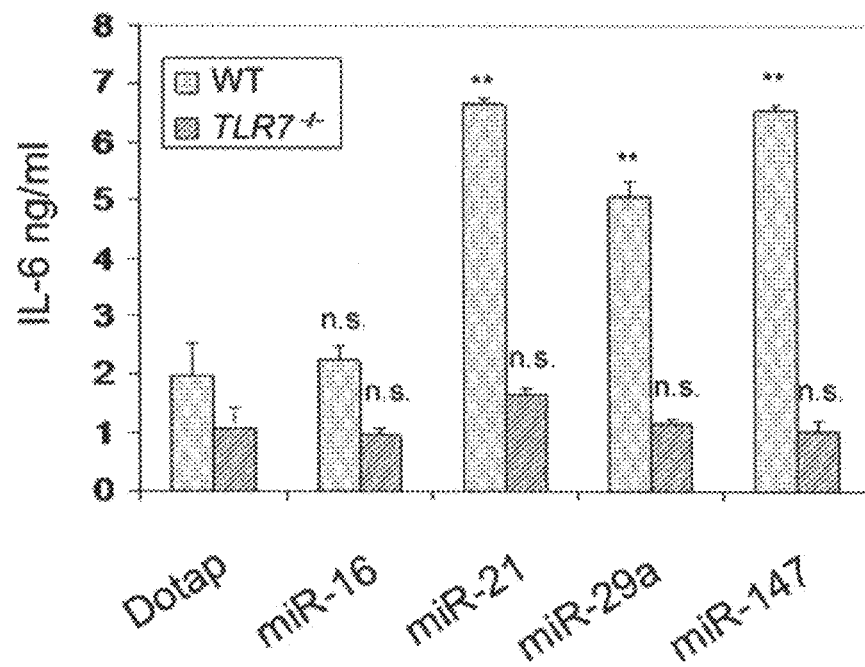
Figure 3C:
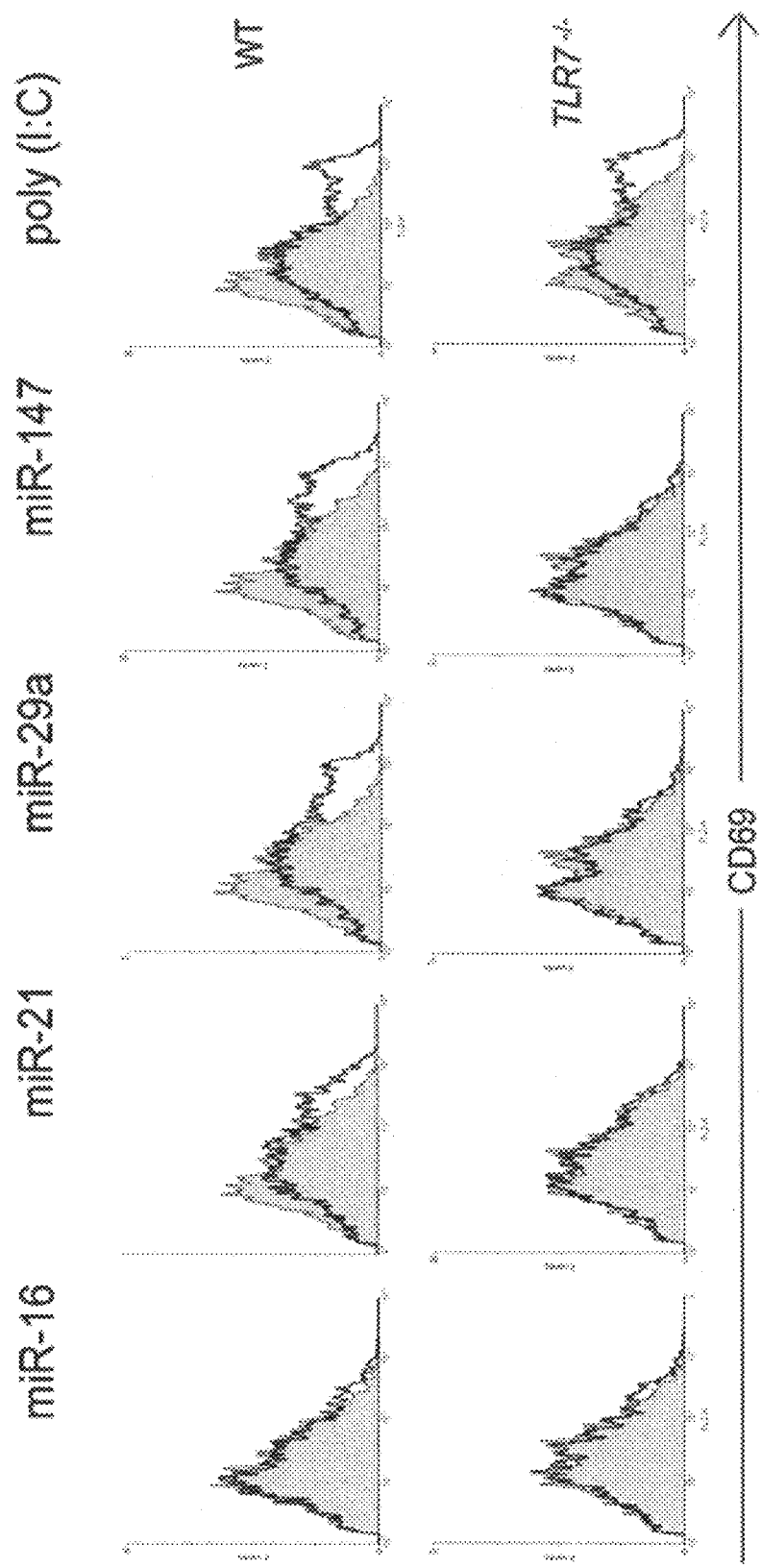
(FIG. 3C) Flow-cytometric analysis of CD69 in spleen cells of WT and TLR7$^{-/-}$ mice treated with the indicated miRNAs.
Figure 3D:
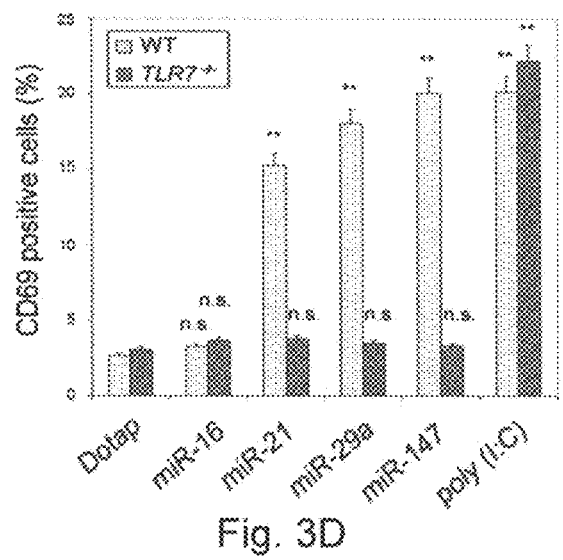
(FIG. 3D) Graphic representation of the results presented in C. Poly (I:C) was used as a positive control for TLR3-mediated CD69 activation.
Figure 3E:
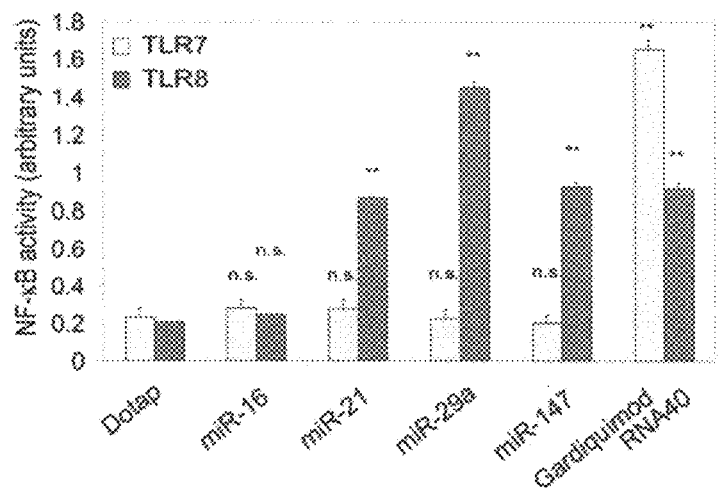
(FIG. 3E) NF-κB activity in TLR7- and TLR8-HEK-293 cells treated with Dotap alone or with Dotap formulations of the indicated miRNAs. Gardiquimod and ssRNA40 were used as positive controls for TLR7- and TLR8-mediated NF-κB activation, respectively.
Figure 3F:
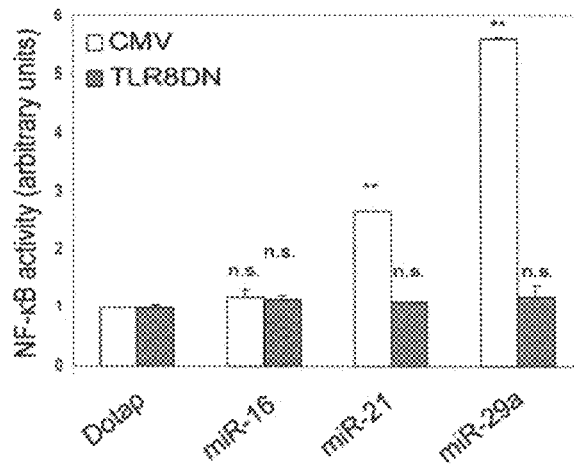
(FIG. 3F) NF-κB activity in TLR8-HEK-293 cells transfected with a plasmid encoding a dominant negative form of TLR8 (TLR8DN), or its empty vector counterpart (CMV) and treated with Dotap alone or with Dotap formulations of the indicated mature miRNAs.
Figure 3G:
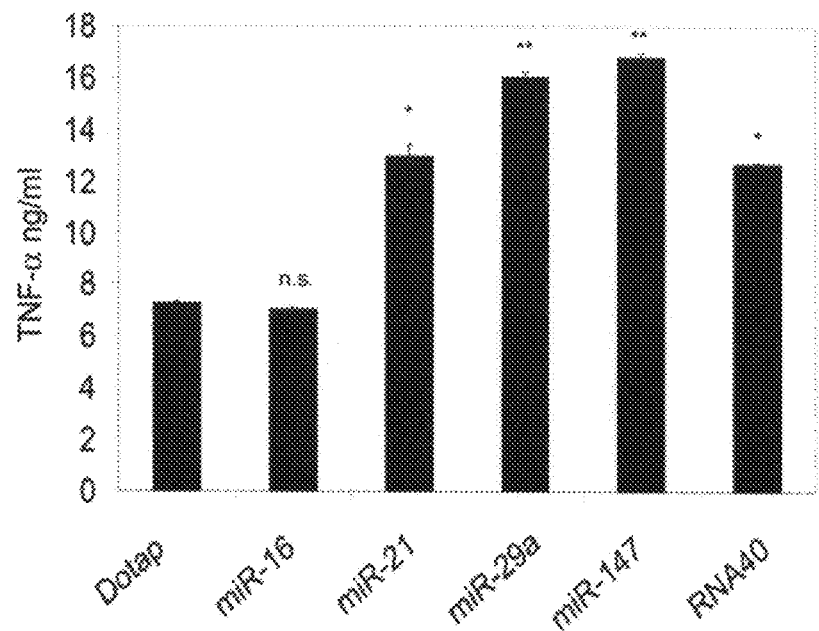
(FIG. 3G and FIG. 3H), ELISA for TNF-α (FIG. 3G) and IL-6 (FIG. 3H) performed on human PBMC isolated from the blood of two healthy donors and treated with Dotap alone or with Dotap formulations of the indicated mature miRNAs. ssRNA40 sequence was used as positive control for TLR8-mediated cytokine secretion. Results in A-H are shown as means±SD. *P<0.05; **P<0.01.
Figure 3H:
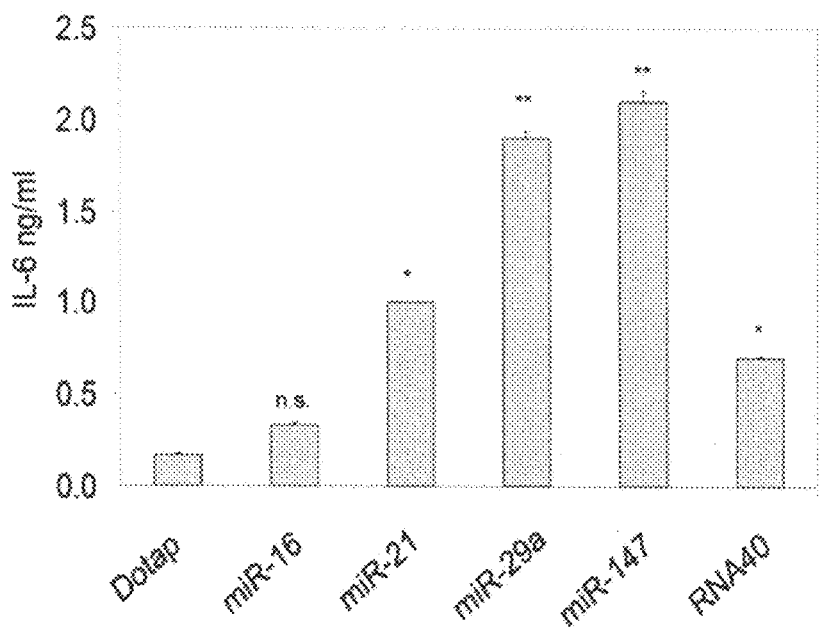
Figure 3I:
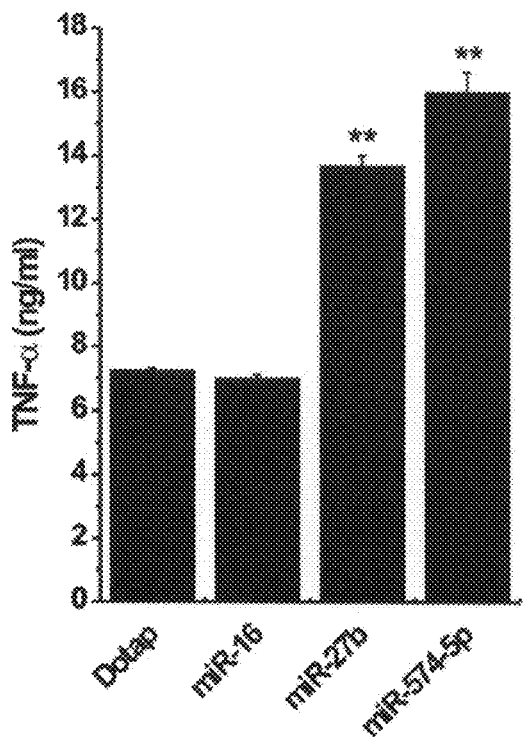
(FIG. 3I and FIG. 3J) ELISA for TNF-α and IL-6 performed on human PBMCs treated with Dotap formulations of mature miR-27b and −574-5p for 24 h. Incubation with Dotap alone and with miR-16 was used as negative control. The experiments were conducted in triplicate. Results are presented as average±SD. *P<0.01; **P<0.0001.
Figure 3J:
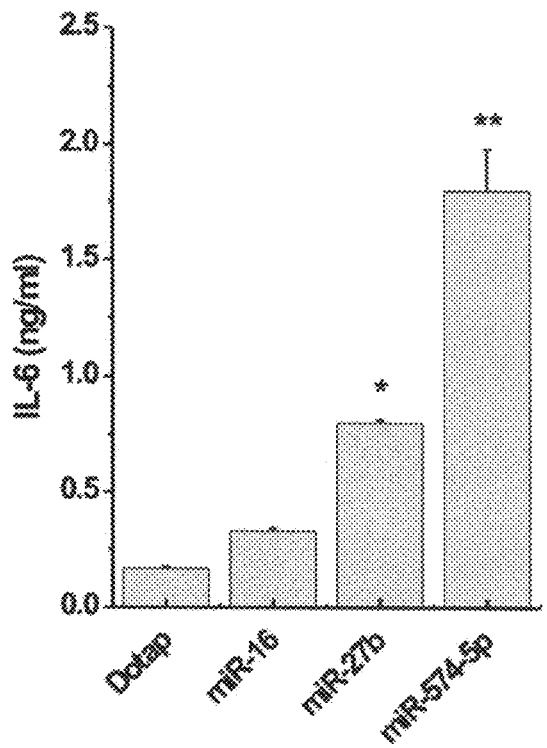
Figure 5:
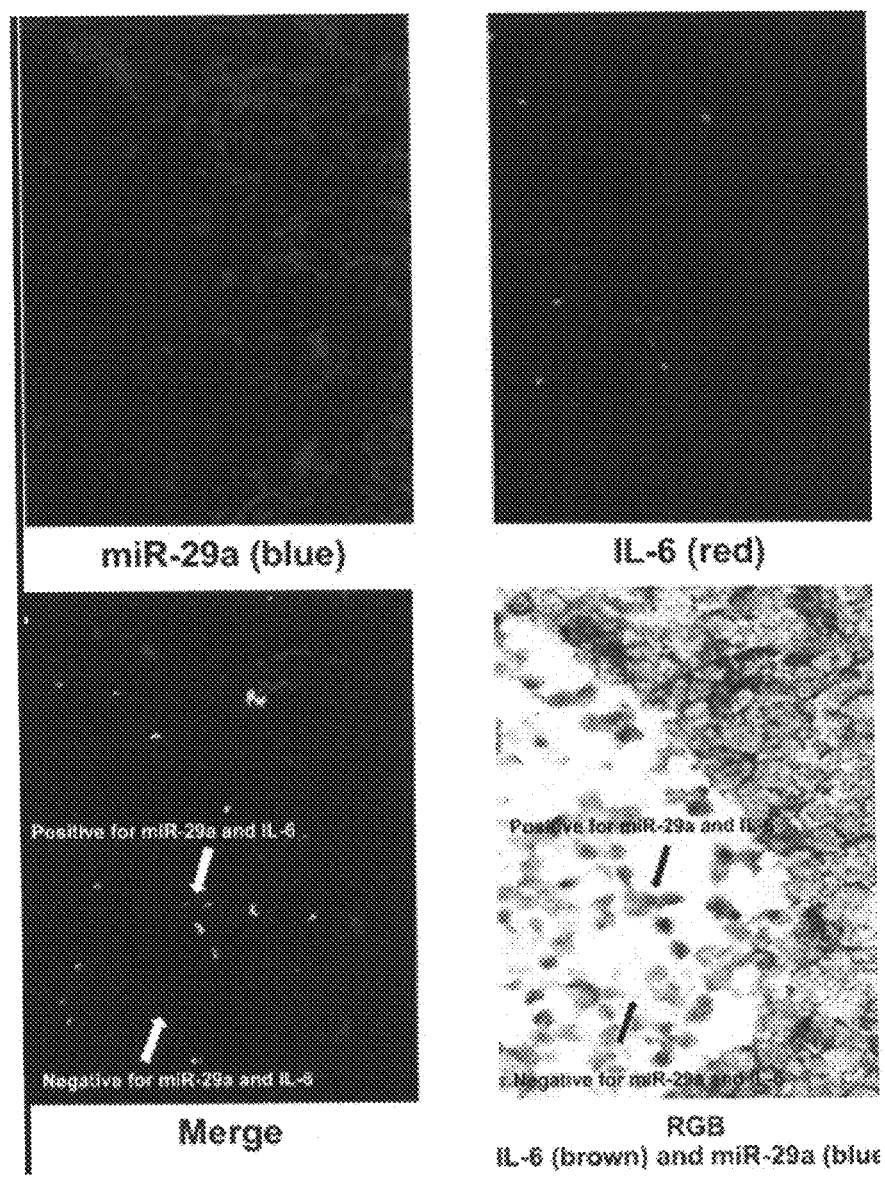
FIG. 5. Co-expression of miR-29a and IL-6 in human macrophages. LNA-ISH (Nuanceconverted image) for miR-29a (depicted as fluorescence blue, upper-left panel) and IL-6 (fluorescent red, upper-right panel) performed on a human lung cancer sample. The merged image (lower-left panel) displays in fluorescent yellow macrophages that coexpress both miR-29a and IL-6. The lower-right panel is the corresponding RGB image: its comparison with the merged image confirms that only macrophages that express miR-29a at the tumor interface also co-express IL-6 (see arrow). Conversely, macrophages that do not express miR-29a do not express IL-6 either.

To investigate whether miRNA-induced activation of TLRs also occurs in human cells, an NF-κB reporter assay was performed in HEK-293 cells. NF-κB, a transcription factor modulating the expression of several cytokine genes, is activated by several TLRs, including the only ssRNA-binding human TLRs, TLR7 and TLR8. Therefore, we treated HEK-293 cells expressing human TLR7 or TLR8 (hereafter, TLR7- and TLR8-HEK-293 cells, respectively) with Dotap alone or with Dotap formulations of miR-16, -21, -29a, or -147 and performed an NF-κB reporter assay. As positive controls Gardiquimod and ssRNA40 were used, specific agonists of TLR7 and TLR8, respectively. NF-κB was activated only in TLR8-HEK-293 cells by each of the tested miRNAs except miR-16 (FIG. 3E). These results suggest that miRNA-induced NF-κB activation is mediated by TLR8 and not by TLR7 in human cells. To confirm this conclusion, transfected were TLR8-HEK-293 cells with a plasmid encoding a dominant negative form of TLR8 (TLR8DN) and treated these cells with the miRNAs of interest. In TLR8DN cells, the activation of NF-κB by miR-21 and miR-29a was abolished (FIG. 3F). Also, incubated were TLR7- and TLR8-expressing human peripheral blood mononuclear cells (PBMCs) from two healthy donors with Dotap alone or Dotap formulations of miR-16, -21, -27b, -29a, -147, -574-5p, or ssRNA40 and an ELISA was performed for TNF-α and IL-6. With the exception of PBMCs treated with Dotap alone and with Dotap-miR-16, each of the other miRNAs and ssRNA40 induced the production of TNF-α and IL-6 (FIGS. 3G-3J). Also, in human primary lung tumors we observed coexpression of miR-29a and IL-6 in macrophages at the tumor interface (FIG. 5). Interestingly, at the tumor interface only the miR-29a-positive macrophages were also IL-6 positive (FIG. 5).

Figure 6A:
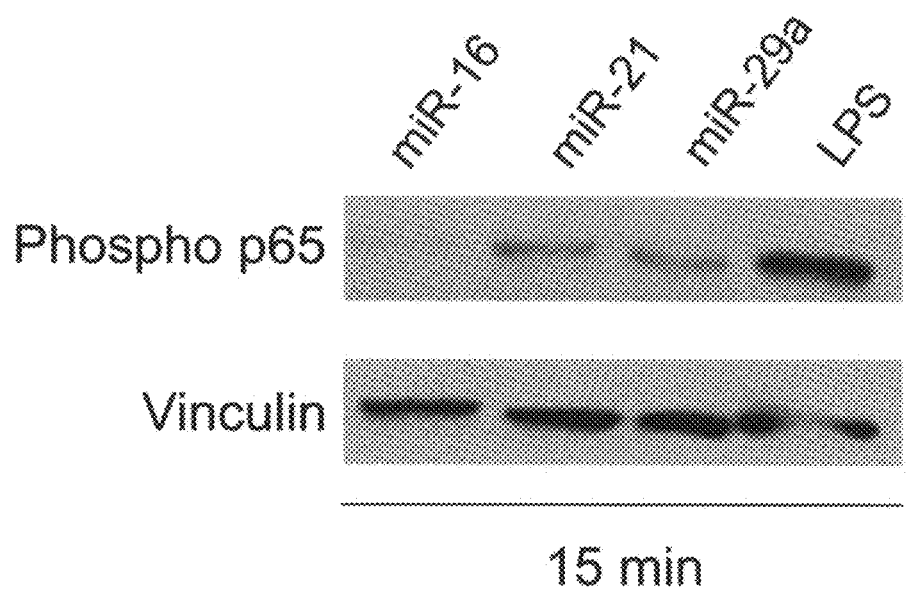
(FIG. 6A) Immunoblotting for phospho p65 in RAW 264.7 cells incubated with Dotap formulations of miR-16, 21 and 29a or treated with LPS (as a positive control). Vinculin was used as a normalizer to show equal protein loading.
Figure 6B:
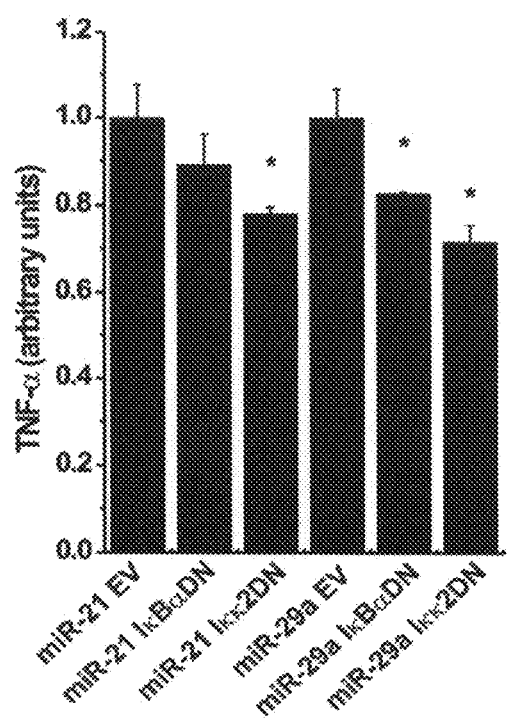
(FIG. 6B) ELISA assay for TNF-α performed on conditioned medium of RAW 264.7 cells transfected with a plasmid encoding a dominant negative form of IκBα (nuclear factor of kappa light polypeptide gene enhancer in B-cells inhibitor, alpha, indicated as "IκBαDN"), a dominant negative form of Iκκ2 (inhibitor of kappa light polypeptide gene enhancer in Bcells, kinase beta, indicated as "Iκκ2DN") or the corresponding empty vector (indicated as "EV") as a control. The assay was performed 48 h after cells were treated with Dotap formulations of the indicated miRNAs. The experiment was conducted in triplicate and data are presented as average±s.d. *, P<0.05.

It was also observed that NF-κB pathway activation is required for miR-21- and -29a-induced secretion of TNF-α and IL-6, because phospho-p65 was induced by miR-21 and -29a (but not miR-16), and transfection with IκBα or IKK2 dominant negative plasmids reduced TNF-α secretion in RAW 264.7 cells (FIGS. 6A and 6B). Overall, the data show that miRNAs secreted by lung cancer cells in exosomes can bind to TLR8 in macrophages at the tumor interface and induce TLR8-mediated activation of NF-κB and NF-κB-mediated secretion of proinflammatory cytokines TNF-α and IL-6.

Figure 6C:
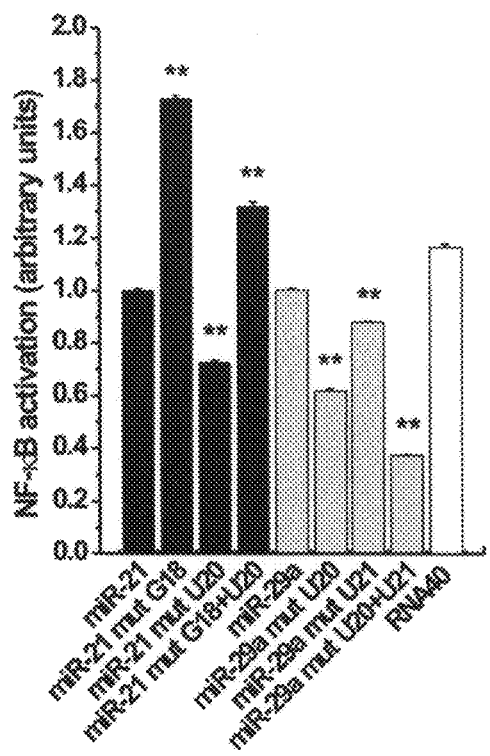
(FIG. 6C) Study of the structural features in the sequence of miR-21 and 29a. TLR8-HEK-293 cells were incubated with Dotap formulations of the indicated mature miRNAs (cfr.

It was investigated which structural features in the sequence of miR-21 and -29a confer the capacity to activate TLR8. It was observed that, unlike miR-16, both miR-21 and -29a presented a GU motif in the nucleotide region 18-21 (GUUG for miR-21 and GGUU for miR-29a), and GU motifs are predominant in the TLR-activating RNA33 (FIG. 14A). Therefore, an experiment disrupted the GU motifs by substituting bases no. 18, 20, and 18+20 in the miR-21 sequence and bases no. 20, 21, and 20+21 in the miR-29a sequence with the corresponding bases of miR-16 for each specific position (FIG. 14B). It was observed that base no. 20 was very important in modulating TLR-mediated activation of NF-κB for both miR-21 and -29a, whereas the G-U mutation in miR-21 base no. 18 significantly increased miR-21 activation of TLR8 in TLR8-HEK-293 cells (FIG. 6C). Overall, it was determined that the specific nature and position of nucleotides in the mature sequence of miRNAs is involved in TLR activation.

MiRNAs in Cancer-Released Exosomes Affect Tumor Growth and Spread by Binding and Activating TLRs in Surrounding Immune Cells.

LLC cells are not a standard model of lung metastasis but represent a well-known model of inflammation-related lung cancer. It has been demonstrated that TNF-α secretion induced by the host myeloid cell is important for the formation of multiplicities in the lungs of mice injected with LLC cells. Thus, it was reasoned that cytokine secretion induced by immune cells stimulated by lung cancer-secreted miRNAs could be involved in the formation of LLC lung multiplicities.

Figure 4A:
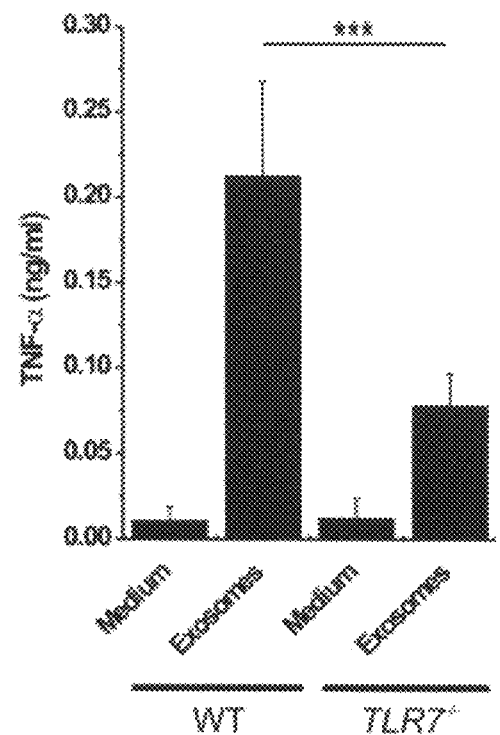
(FIG. 4A and FIG. 4B) ELISA for TNFα (FIG. 4A) and IL-6 (FIG. 4B) performed on conditioned medium of peritoneal macrophages isolated from WT (n=3) and TLR7$^{-/-}$ (n=3) mice, incubated with RPMI (Medium; negative control) or exosomes purified from LLC cells for 48 h.
Figure 4B:
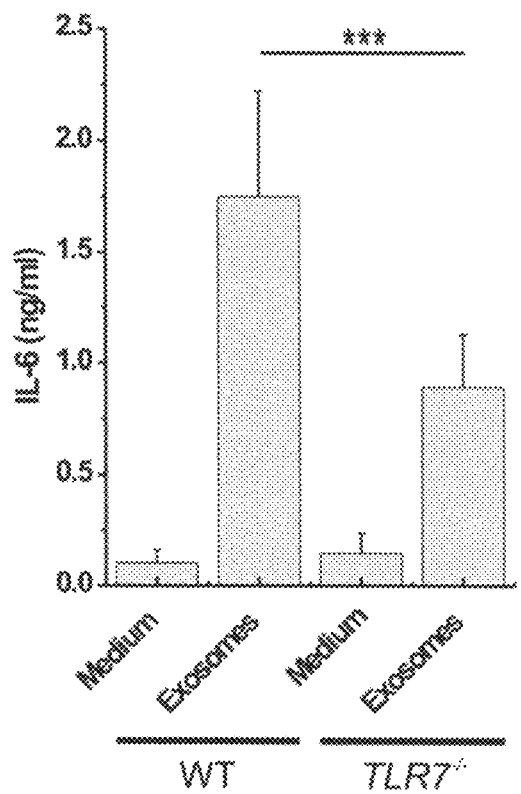
Figure 4C:
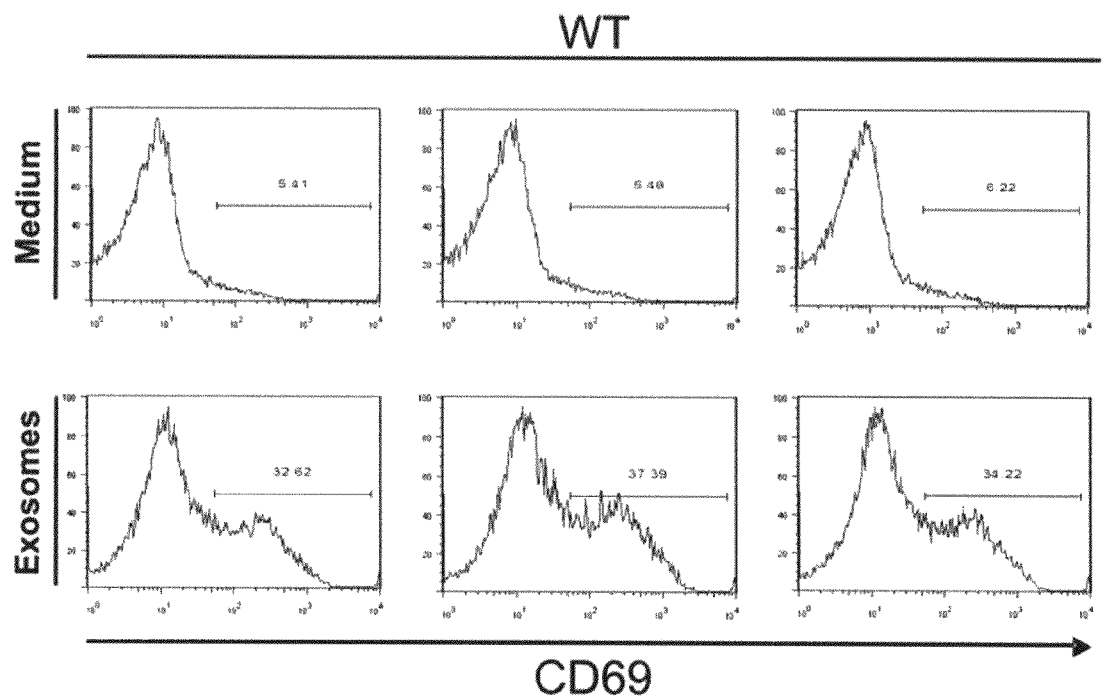
(FIG. 4C and FIG. 4D) Flow-cytometric analysis of CD69 in spleen cells isolated from WT and TLR7$^{-/-}$ mice treated as in FIG. 4A and FIG. 4B.
Figure 4D:
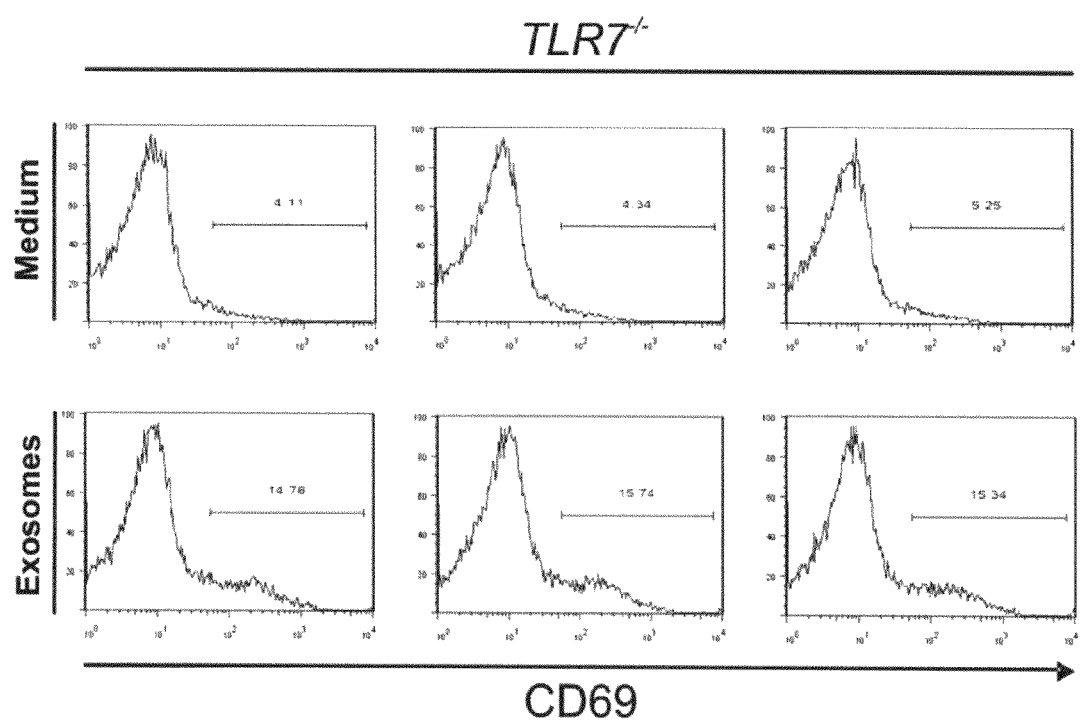
Figure 7A:
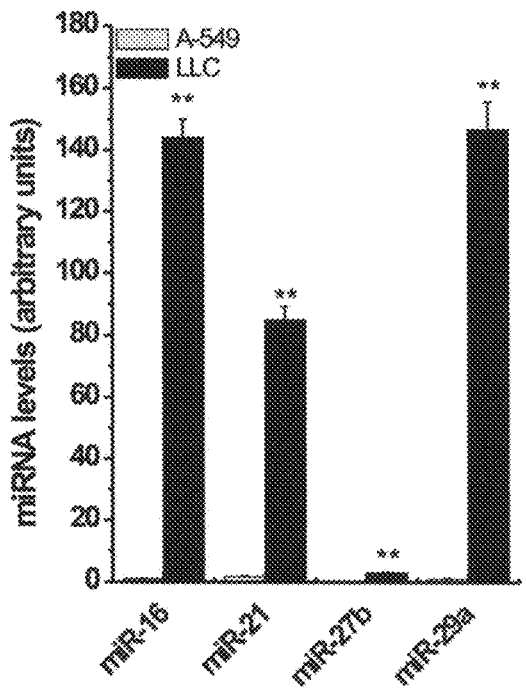
FIG. 7. Functional studies performed with miRNA-containing exosomes. (A) Quantitative Real-Time PCR for miR-16, 21, 27b, and 29a in the RNA extracted from exosomes in the supernatant of LLC and A-549 cells. The experiments were conducted in triplicate and presented as average±s.d. , P<0.0001.
(FIGS. 7B, 7C) ELISA assay for TNF-α (FIG. 7B) and IL-6 (FIG. 7C) performed on conditioned medium of peritoneal macrophages isolated from WT (n=3) B6 mice and incubated with LLC supernatant containing exosomes (Conditioned Medium) or with LLC supernatant after removal of exosomes by ultracentrifugation (Ultra-centrifuged Medium).
(FIG. 7D) CD69 activation detected by cytofluorimetry performed on spleen cells isolated from WT (n=3) B6 mice and treated as in FIG. 7B and FIG. 7C. Data are presented as average±s.d. , P<0.005. (E) NF-κB activation in TLR8-HEK-293 cells treated with LLC-released exosomes. TLR8-HEK-293 cells were not pre-treated ("Exosomes" group), or pre-treated with Bafilomycin A ("Exosomes+Bafilo" group). As a positive control, TLR8-HEK-293 cells were treated with artificial exosomes containing the TLR8 activator ssRNA40 ("ssRNA40" group). The experiments were conducted nine times, and presented as average±s.d. , P<0.0005 ("Exosomes" vs "Exosomes+Bafilo").
(FIG. 7F) LLC cells were transfected with LNA anti scrambled (control), or LNA anti miRNAs for miR-16 (LNA anti miR-16) and for both miR-21 and 29a (LNA anti miR-21/29a). After 48 h cells were collected and RNA extracted from both LLC cells and exosomes purified from their supernatants. The level of all three miRNAs was detected by quantitative Real-Time PCR both in LLC cells (left panels, labeled as "LLC cells"), and in the exosomes purified from their supernatants (right panels, labeled as "LLC Exosomes"). The experiments were conducted in triplicate and presented as average±s.d. , P<0.001.
(FIG. 7G) Lung multiplicities in B6 mice injected with wild type LLC cells followed by injections of Dimethylsulphoxide (DMSO) (n=5, group "LLC wtctrl"), with wild type LLC cells followed by injections of the miRNA and exosome release inhibitor GW4869 (n=5, group "LLC wt-GW4869"), or with wild type LLC cells followed by injections of GW4869 and two intra-tail vein rescue injections of LLC derived exosomes (n=5, group "LLC wt-GW4869 rescue"). Data are presented as mean±s.d. *, P<0.05; **, P<0.005.
Figure 7B:
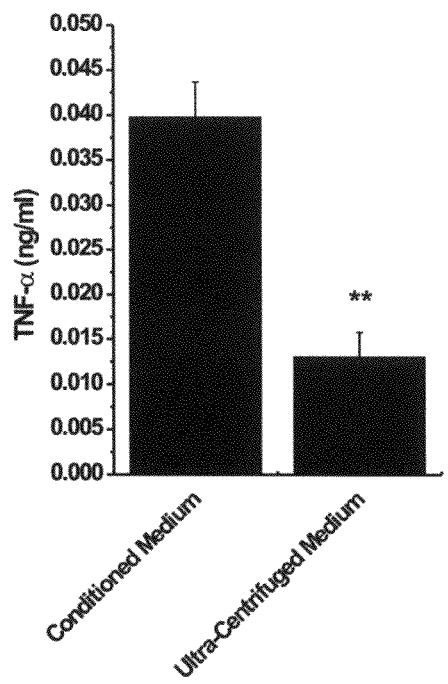
Figure 7C:
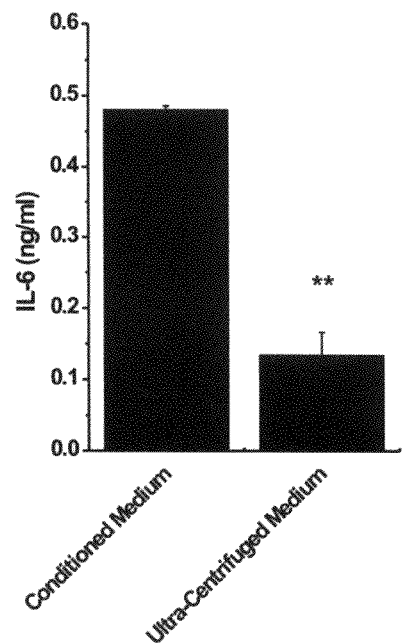
Figure 7D:
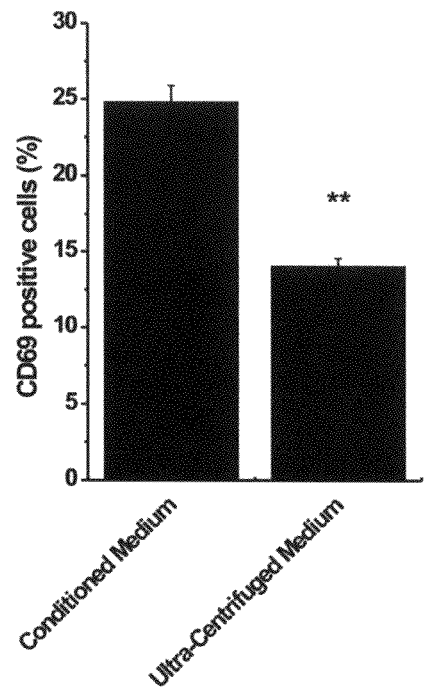

Exosomes were purified from the supernatant of LLC and A-549 cells and assessed for miR-16, -21, -27b, and -29a by quantitative real-time PCR. LLC cells released the highest level of miR-16, -21, and -29a (FIG. 7A), confirming that these cells represent a good model. LLC-derived exosomes (or empty medium as a control) were co-cultured with peritoneal macrophages isolated from WT or TLR7$^{-/-}$ mice and observed significantly increased TNF-α and IL-6 secretion in the presence of exosomes and in WT versus TLR7$^{-/-}$ mice (FIGS. 4A and 4B). Also co-cultured were LLC-derived exosomes (or empty medium as a control) with spleen cells isolated from WT or TLR7$^{-/-}$ mice and observed a significantly higher activation of CD69 in the presence of exosomes and in WT versus TLR7$^{-/-}$ mice (FIGS. 4C and 4D). Finally performed was an ultracentrifugation of LLC supernatant and co-cultured conditioned medium or ultracentrifuged (and presumably exosome-depleted) medium with peritoneal macrophages and spleen cells of WT mice and confirmed that removing exosomes significantly reduced TNF-α and IL-6 secretion by macrophages and CD69 activation by spleen cells of WT mice (FIG. 7B-7D).

Figure 4E:
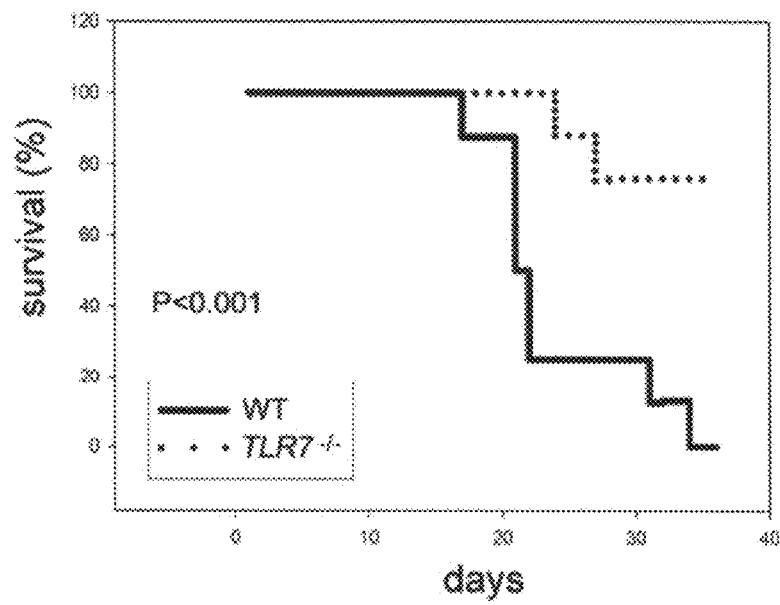
(FIG. 4E) Kaplan-Meier curves for WT (n=7) and TLR7$^{-/-}$ (n=7) mice after tail injection of LLC cells.
Figure 4F:
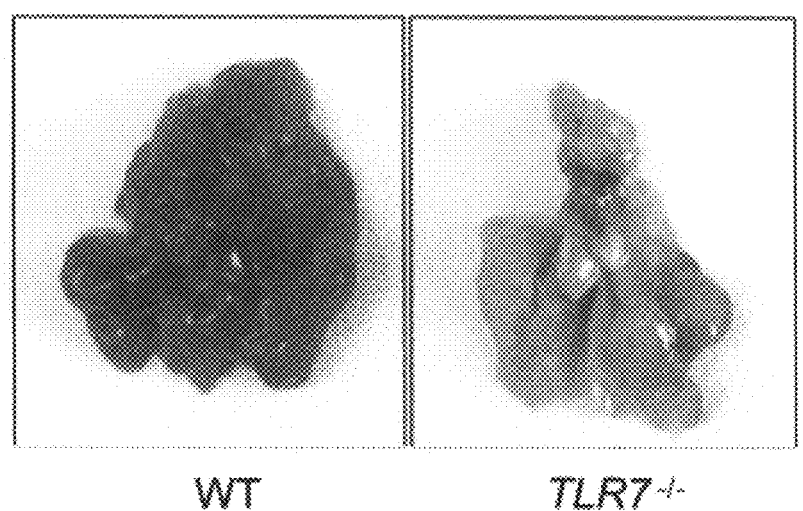
(FIG. 4F) Representative images of different tumor multiplicities detected in lungs in the WT and the TLR7$^{-/-}$ mouse groups.
Figure 4G:
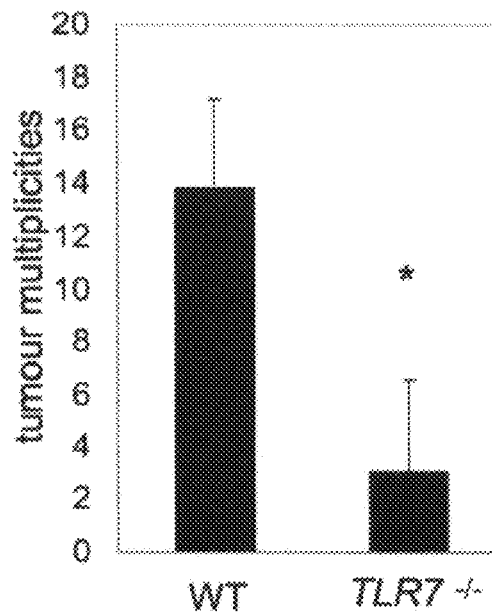
(FIG. 4G) Tumor multiplicities in the WT and TLR7$^{-/-}$ mouse groups, after tail injection of LLC cells.
Figure 7E:
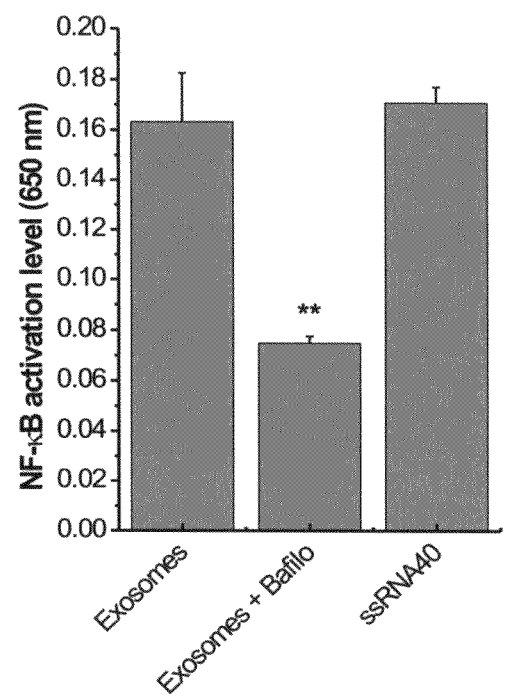

Interestingly, some TNF-α and IL-6 secretion and CD69 activation also were observed in TLR7$^{-/-}$ mice in the presence of exosomes showing that these vesicles also carry other signals able to activate cytokine secretion and CD69 activation. Also co-cultured were LLC-derived exosomes (or ssRNA40 as a positive control) with WT TLR8-HEK-293 cells or with TLR8-HEK-293 cells pretreated with Bafilomycin A (an antibiotic that perturbates endosomal function) and observed significantly reduced NF-κB activation (P<0.0005) in the presence of Bafilomycin A (FIG. 7E). Next, LLC cells were injected into the tails of WT and TLR7$^{-/-}$ mice and the overall survival of the animals and number of lung multiplicities after necropsy was assessed. The Kaplan-Meier curves indicate significantly shorter overall survival of LLC-injected WT mice versus TLR7$^{-/-}$ mice (P<0.001) (FIG. 4E). Also, lung tumor multiplicities were significantly higher in LLC-injected WT mice than in LLC-injected TLR7$^{-/-}$ mice (average number of multiplicities, 13.8 versus 3.8, respectively; P<0.05) (FIGS. 4F and 4G). These data confirm the importance of TLR7 activation in the development of lung cancer multiplicities.

Figure 4H:
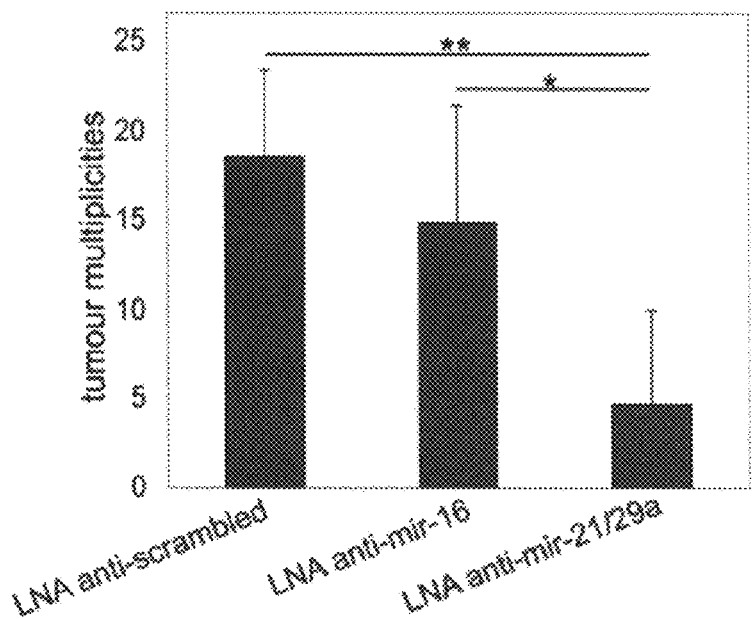
(FIG. 4H) Tumor multiplicities in B6 mice injected with LLC cells transfected with LNA anti-scrambled (control; n=6), LNA anti-miR-16 (n=6), or LNA anti-miR-21/29a (n=6).
Figure 4I:
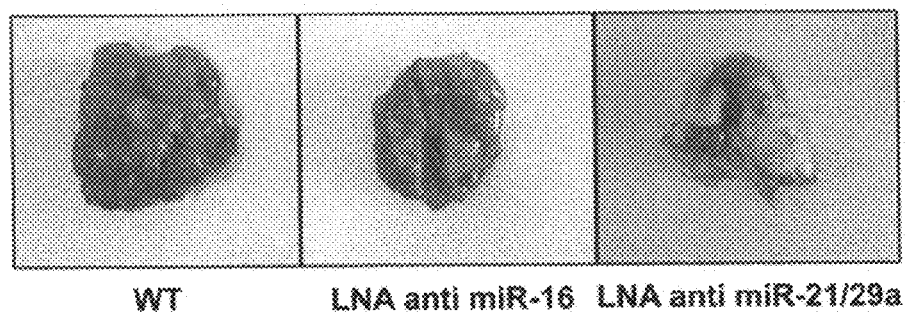
(FIG. 4I) Representative images of lungs in mice injected with LLC cells transfected as indicated. Results in FIGS. 4A-E, G, and H are shown as means±SD. *P<0.05; P<0.01; *P≤0.005.
Figure 7F:
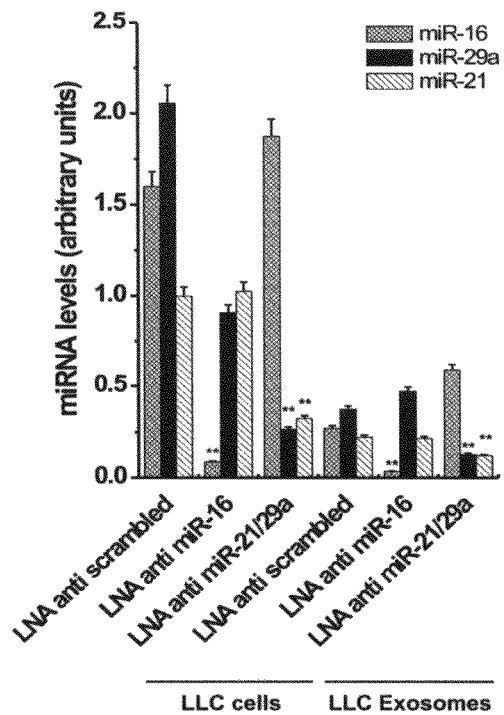
Figure 7G:
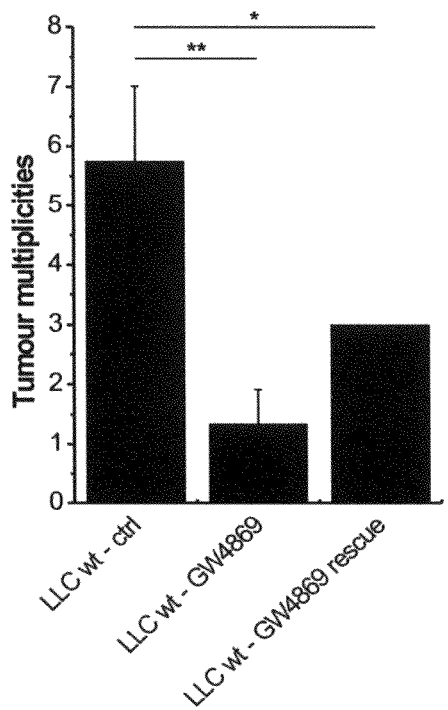

Finally, to assess the role of miRNAs released from lung cancer exosomes in TLR7 activation and in the metastatic process, the expression was silenced of miR-16 or of miR-21 and -29a combined in LLC cells by Locked Nucleic Acid (LNA) anti-miRNA inhibitors. After anti-miRNA transfection, the levels of the silenced miRNAs were reduced in the exosomes derived from these cells (FIG. 7F). The transfected cells were injected into the tail vein of B6 mice, and lung multiplicities were counted. Mice injected with LLC cells not expressing miR-21/29a in their exosomes formed fewer lung multiplicities (FIGS. 4H and 4I). It was also observed that WT mice treated with GW4869, an inhibitor of miRNA and exosome secretion, produced a significantly lower number of lung multiplicities when injected with LLC cells. This effect could be rescued at least in part when LLC-derived exosomes were injected i.v. in GW4869-treated mice (FIG. 7G). We further investigated which miRNAs are expressed in cancer cells and adjacent normal lung tissues in mice injected with anti-scrambled LLCs or anti-miR-21/29a LLCs. Cancer cells in lung tumors developed by mice injected with anti-scrambled LLC were positive for the anti-scrambled oligonucleotide.

Figure 8:
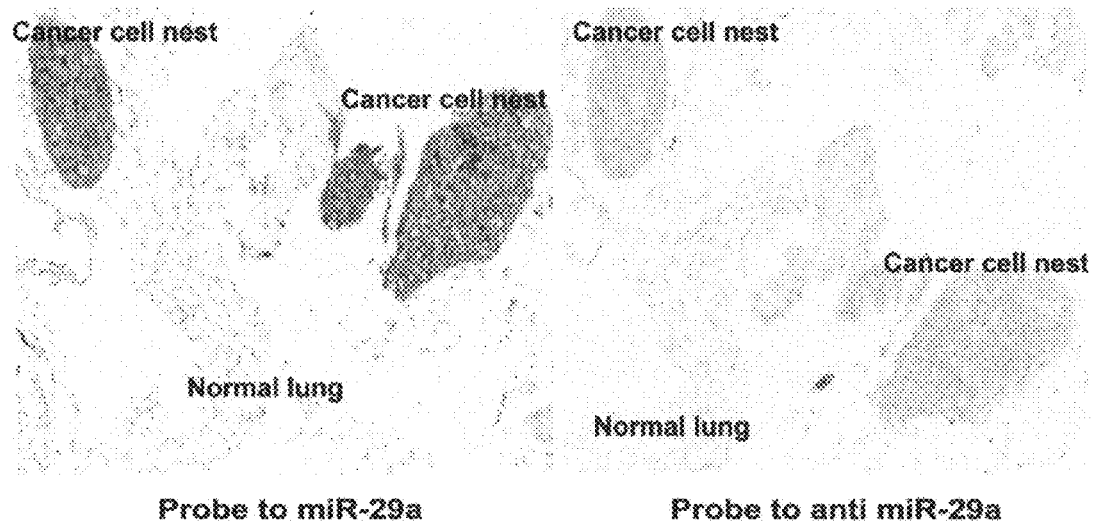
Figure 9A:
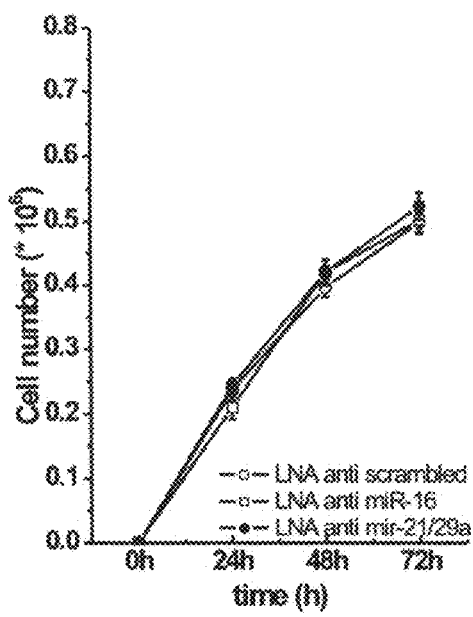
(FIG. 9A) Growth curve of LLC cells determined 24 h, 48 h and 72 h after transfection with LNA anti scrambled (control), LNA anti miR-16 or LNA anti miR-21 and 29a in combination (LNA anti miR-21/29a).
Figure 9B:
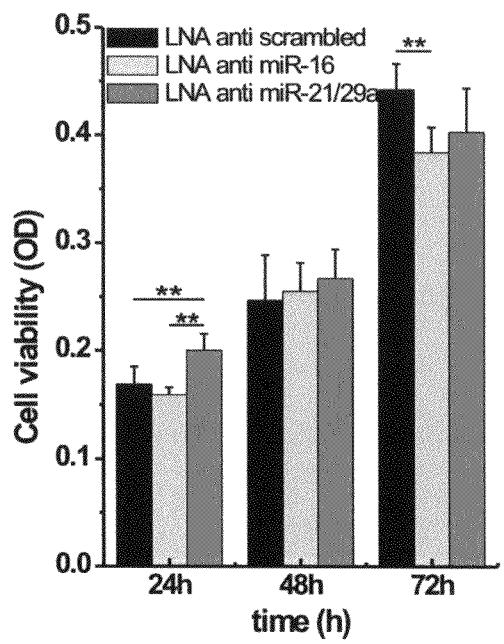
(FIG. 9B) MTS assay on LLC transfected cells at the indicated time points. LLC viability is represented as the OD value obtained by reading the plate at 490 nm.
Figure 9C:
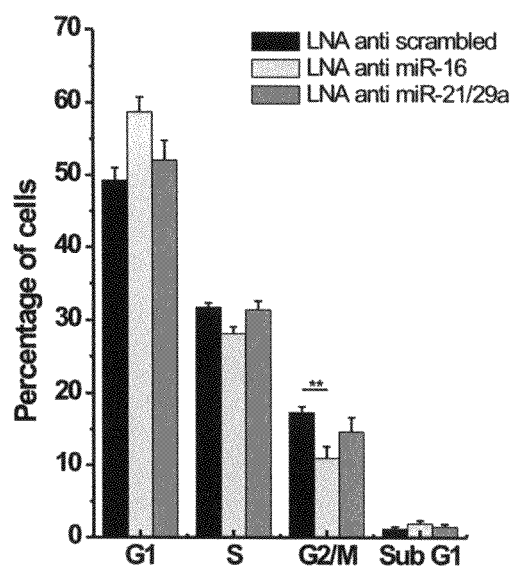
(FIG. 9C) Cell cycle assay of LLC cells collected 48 h after transfection and performed by cytofluorimetry.
Figure 9D:
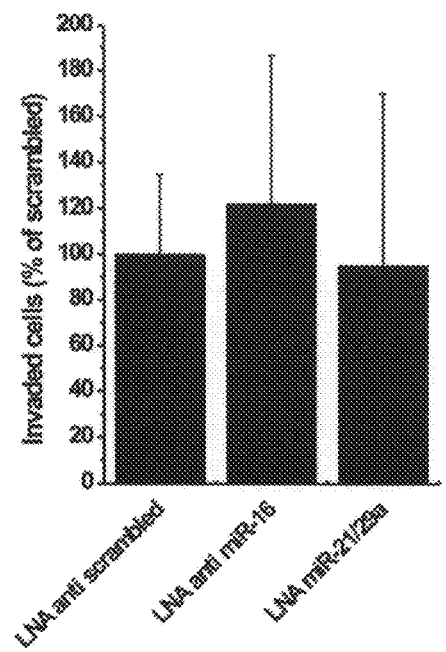
(FIG. 9D) Invasiveness assay performed on transfected LLC. The percentage of cell invasion for each treatment was normalized with respect to the control (LNA anti scrambled).
Figure 9E:
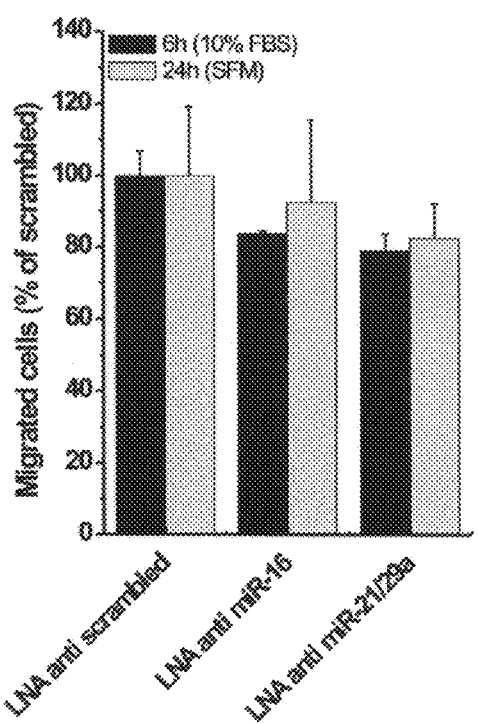
(FIG. 9E) Migration assay of transfected LLC cells assessed by incubating the cells in the transwell with 10% FBS-supplemented medium for 6 h or with serum-free medium for 24 h.
Figure 9F:
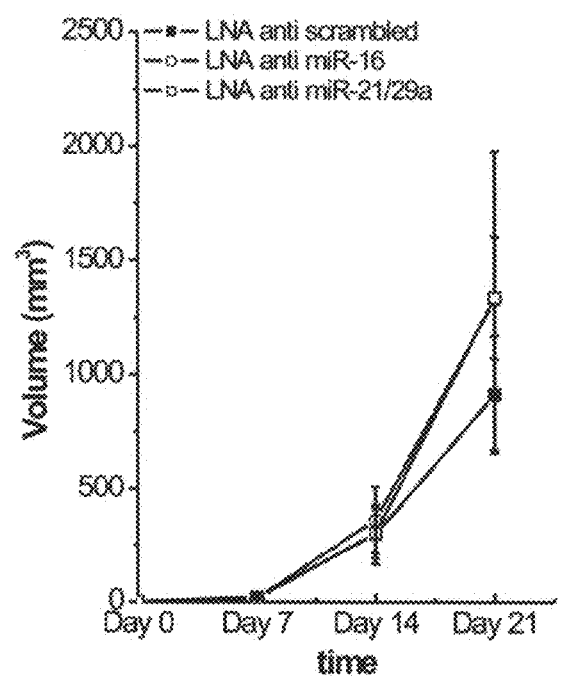
(FIG. 9F) Tumor growth in xenograft nude mice (n=9) injected subcutaneously with LLC cells transfected with LNA anti scrambled (control), LNA anti miR-16 (LNA anti miR-16) or LNA anti miR-21 and miR-29a (LNA anti miR-21/29a). Data are normalized with respect to the control. The experiments were conducted in triplicate unless otherwise specified and presented as average±s.d. **, P<0.005.
Figure 10:
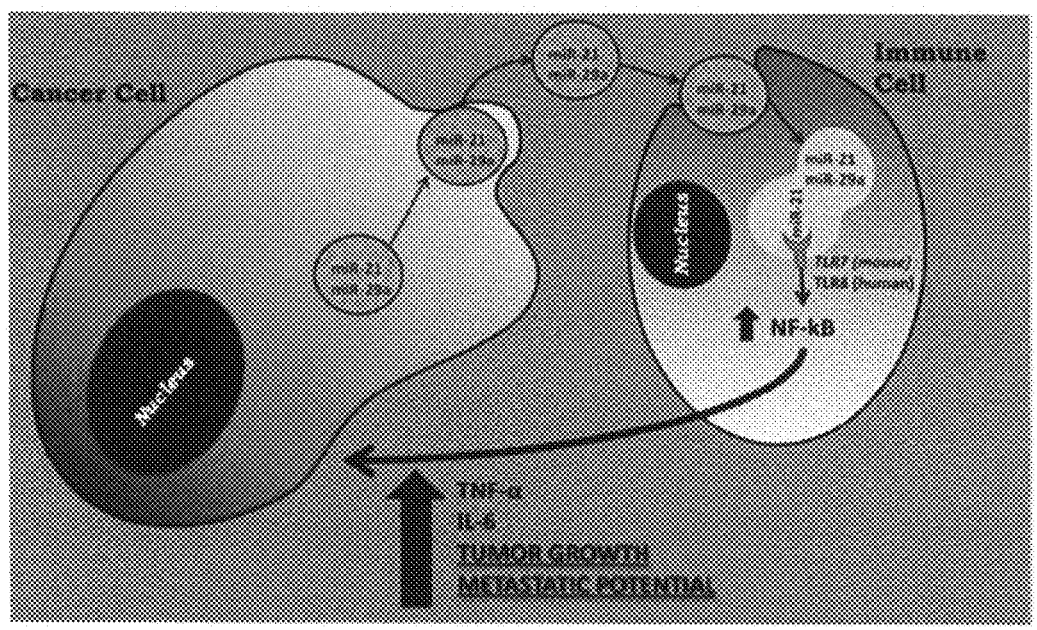
FIG. 10. MiRNAs are secreted by cancer cells in exosomes and can reach and bind TLR7 (in mice) or TLR8 (in humans) in the endosomes of surrounding immune cells. As a result, TLRs are activated, and the immune cells release cytokines, such as TNF-α and IL-6, which promote cancer growth and dissemination.

Interestingly, in mice injected with anti-miR-21/29a LLC cells, all cancer cells localized in the lung were positive for miR-29a expression and negative for the anti-miR-29a oligonucleotide expression (FIG. 8). These findings indicate that only the LLC cells in which miR-29a was not successfully silenced by the LNA anti-miR-21/29a transfection were able to localize to the lung.

To exclude the possibility that the observed differences were caused by the effects of miRNA silencing unrelated to their exosome release, the effects of miR-16 and -21/29a silencing on LLC biology were investigated. When miR-16 or miR-21/29a was silenced, no difference was observed in LLC growth curve, cell viability, cell cycle, LLC invasiveness, or LLC migration capabilities or in tumor growth in in vivo xenograft mouse models (FIG. 9). Results show that miR-21 and -29a secreted by tumor cells in exosomes can bind to TLR8 (and TLR7) and activate these receptors in immune cells, leading to TLR-mediated NF-κB activation and secretion of prometastatic inflammatory cytokines. It has been shown previously that tumor secretion of the extracellular matrix proteoglycan versican induces a proinflammatory response by activating TLR2:TLR6 complexes in myeloid cells. It is now shown herein that tumor-secreted miRNAs play an important role in the protumoral inflammatory process by activating the TLR8 response on immune cells. As a result, tumor cells tend to generate more lung multiplicities when this paracrine loop is intact. Although LLC cells are not a standard model of lung cancer metastasis, the data identify a mechanism of action of miRNAs as agonists of a specific receptor family and that this mechanism is involved in the tumor microenvironment interaction.

The binding of miR-21 and -29a to TLR7 and TLR8 induces activation of immune cells (indicated by activation of CD69) and this effect is not mediated by binding to human TLR7. Moreover, in an in vivo mouse model of lung cancer [mice injected with Lewis Lung Carcinoma (LLC) cells] it is shown that, by binding to TLR7, cancer cell-secreted miR-21 and -29a in exosomes metastasize preferentially to the lung and reduce overall survival, compared with TLR knockout mice in which this mechanism is impaired. Drugs affecting exosome secretion by cancer cells significantly reduce the metastatic potential of LLC cells, and this effect can be rescued by injecting tumor-bearing mice with exosomes secreted by LLC cells.

The finding here that miRNAs act as ligands, able to bind and activate a receptor in a hormone-like fashion, has broader implications beyond cancer. For example, these mechanisms impact autoimmune diseases and inflammatory diseases. This reveals a mechanism by which cancer cells cross-talk with surrounding immune cells and induce them to release cytokines that increase tumor growth and spread. The present study demonstrates the importance of the tumor microenvironment in cancer growth and dissemination and provides molecular targets for the development of anticancer treatments.

Methods

Cell Culture, Transfection, and Treatment.

All cell lines were purchased from American Type Culture Collection unless indicated otherwise. Human HEK-293 cells were maintained using standard conditions and were grown in DMEM (Gibco), supplemented with 10% (vol/vol) FBS. Human HEKBlue-TLR7 and TLR8 293 cells (Invivogen) (indicated as TLR7-HEK-293 or TLR8-HEK-293, respectively) were cultured in DMEM supplemented with 10% (vol/vol) FBS, Normocin (50 µg/mL), Blasticidin (10 µg/mL), and Zeocin (100 µg/mL) (Invivogen).

Human A-549 and SK-MES and murine LLC cells were maintained in RPMI 1640, supplemented with 10% (vol/vol) FBS. RAW 264.7 cells were maintained in DMEM supplemented with 20% (vol/vol) FBS. All cells were transfected using Lipofectamine LTX and Plus Reagent (Invitrogen) following the manufacturer's instructions.

For all experiments, cells were treated with 15 µg of HPLC-purified synthetic miRNAs (Integrated DNA Technologies) complexed with Dotap Liposomal Transfection Reagent (Roche) as previously described.

For the experiment with Bafilomycin A, TLR8-HEK-293 cells were seeded in a 24-well plate at a density of 200,000 cells per well. The next day cells were preincubated with 10 nM Bafilomycin A (Sigma) for 30 min and then were treated for 24 h with exosomes purified from LLC cells in the presence or absence of 10 nM Bafilomycin A. Cell supernatants were collected and harvested, and the QUANTI-Blue Assay was performed.

Exosome Purification.

Serum-free conditioned medium was collected from all the mentioned cell lines at the indicated time points after cell treatment. Medium then was harvested at 14,000×g for 15 min to eliminate cell debris. Exosomes were precipitated by using exosome precipitation solution (ExoQuick; System Bioscience) following the manufacturer's instructions.

Immunofluorescence.

HEK-293 cells were seeded 24 h before transfection onto 60-mm plates and allowed to grow to 50% confluence. Then they were transfected with 1 µg of plasmid encoding GFP-TLR8 (Origene). After 48 h cells were treated with the indicated mature miRNA oligos conjugated to Cy-5 fluorophore as described above, washed four times with PBS, and incubated for 15 min with LysoTracker blue DND-22 (Invitrogen) diluted 1:25,000 in PBS.

For the immunofluorescence experiment with physiological exosomes, HEK-293 cells were transfected with 1 µg of plasmid encoding GFP-CD9 (Origene). After 24 h cells were detached and cocultured with RAW 264.7 cells previously seeded onto a 40-mm coverslip at a density of 700,000 cells/mL and stained with blue cell tracker (Invitrogen). After 30 min of incubation, allowing HEK-293 cells to seed, the coculture was finally stained with LysoTracker red DND-99 (Invitrogen) diluted 1:25,000 in PBS, and coverslips were analyzed with a confocal microscope.

NanoString® nCounter® Assays.

Both cells and exosomes purified from 300 µl of SKMES and A-549 conditioned media were processed in hextuplicate for RNA extraction, using Trizol reagent (Invitrogen) and following the manufacturer's instructions. The RNA concentration and quality were estimated by Nanodrop assay (Nanodrop Spectrophotometer 2000), and 100 ng were used as input for nCounter® miRNA sample preparation reactions. All sample preparation was performed according to manufacturer's instructions (NanoString Technologies). Preparation of small RNA samples involves the ligation of a specific DNA tag onto the 3' end of each mature miRNA. These tags are designed to normalize the melting temperatures of the miRNAs as well as to provide a unique identification for each miRNA species in the sample. The tagging is accomplished in a multiplexed ligation reaction using reverse-complementary bridge oligonucleotides to direct the ligation of each miRNA to its designated tag. Following the ligation reaction, excess tags and bridges are removed, and the resulting material is hybridized with a panel of miRNA: tag-specific nCounter® capture and barcoded reporter probes. Hybridization reactions were performed according to manufacturer's instructions with 5 µl of the 5-fold diluted sample preparation reaction. All hybridization reactions were incubated at 64° C. for a minimum of 18 h. Hybridized probes were purified using the nCounter® Prep Station (NanoString Technologies) following the manufacturer's instructions to remove excess capture and reporter probes and to immobilize transcript-specific ternary complexes on a streptavidin-coated cartridge. Data collection was carried out on the nCounter® Digital Analyzer (NanoString Technologies) following the manufacturer's instructions to count individual fluorescent barcodes and quantify target RNA molecules present in each sample. For each assay, a high-density scan (600 fields of view) was performed. For the analysis, only the miRNAs that in both cell lines had a number of code counts ≥50 (twice as much as the average negative controls of 25 code counts) were further considered. The threshold for FIG. 1A was chosen in order to eliminate the background noise and make sure that the levels of identified miRNAs represented real exosome enrichment. The average plus a multiple of the standard deviation of all negative control probe counts in a lane could be defined as background for that lane. Therefore, and also as recommended in the NanoString Expression Data Analysis Guide, we operated as follows:
1. For each lane, the average of all the negative control counts was calculated.
2. For each lane, the standard deviation of all the negative control counts was calculated.
3. A multiple of the standard deviation was added to the average. Specifically, the standard deviation was multiplied by two before adding to the average.
4. The background threshold was thereby determined.
5. In order to restrict the analysis to those miRNAs that are really over-expressed in the exosomes, an even more stringent threshold was used, by further doubling the background threshold (as calculated in 4). This calculation gave a threshold value of 51.04, which was rounded to 50.

Quantitative Real-Time PCR.

Quantitative Real-Time PCR analysis for miRNAs was performed in triplicate with the TaqMan MicroRNA assays kit (Applied Biosystems), according to the instructions of the manufacturer. RNU44 (human samples) or snoRNA234 (murine samples) was used to normalize the quantitative Real-Time PCR on RNAs extracted from the cells. Total RNA concentration was used to normalize quantitative Real-Time PCR performed on miRNAs purified from exosomes.

Co-Immunoprecipitation Experiments.

TLR8-HEK-293 cells were treated with the indicated miRNAs and incubated at 37° C. for 20 min They were then extensively washed with 1.5 ml of ice-cold PBS, collected and lysis performed through a 5 min incubation with 150 μl of Polysome lysis buffer on ice. Lysates were finally frozen in dry ice for 1 h, and then harvested at 14,000 g for 15 min 100 μl of each lysate was added to 50 μl of A/G protein (Santa Cruz), which was previously pre-incubated with 25 μl of NT2 buffer 5% BSA for 1 h and then with 100 μl of anti-TLR8 antibody in rotation at 4° C. overnight. Lysates were further incubated with beads (extensively washed with NT2 buffer, according to the manufacturer's protocol) (Mylteni) in a final volume of 850 μl of NT2 buffer supplemented with 1 μl of 1M DTT and 34 μl of 0.5M EDTA Immunoprecipitation was performed for 5 h at 4° C. in rotation. Beads were washed 4× with NT2 buffer, and was incubated with 100 μl of NT2 buffer and Proteinase K (Qiagen) at 55° C. for 30 min, then RNA was extracted with Trizol and processed for real-time analysis, as previously reported.

The miRNA immunoprecipitation for TLR8 was performed as follows. TLR8-GFP-HEK-293 cells were treated with 5'-biotinylated mature miR-16, 29 or RNA40 (15 μg/mL final concentration) at 37° C. for 20 min Cells were fixed and lysed as previously described2, and co-immunoprecipitation was performed by using streptavidin-conjugated magnetic beads (Miltenyi), according to the manufacturer's instructions. TLR8-GFP protein was detected with anti-GFP antibody.

Western Blotting.

Cells were washed in PBS, scraped and collected in a 15 ml tube, then harvested at 1,500 g for 10 min. The pellet was resuspended in NP-40 Cell Lysis Buffer (Invitrogen) supplemented with protease inhibitors (Roche) for 30 min at 4° C. The suspension was finally harvested at 14,000 g for 10 min and the supernatant, containing solubilized proteins, collected. Proteins were quantified using Bio-Rad Protein Assay (Bio-Rad), following the manufacturer's instructions, and 30 μg of each sample were loaded on a Criterion Tris-HCl 4-20% pre-cast gel (Bio-Rad), transferred onto PVDF membranes and probed with anti-GFP (Novus Biologicals) and anti-TLR8 (Santa Cruz) antibodies. Isotype-matched, horseradish-peroxidase-conjugated secondary antibodies (GE Healthcare) were used, followed by chemiluminescence detection (Denville Scientific, Inc.). Also, for immunoblotting the following antibodies were used: anti-CD9, and anti-CD63 (Santa Cruz), and anti-phospho p65 (Cell Signaling). LNA-ISH Our protocol for protein/microRNA as well as protein/protein co-expression analysis has been previously published. In brief, in situ hybridization for the microRNA is done using the 5' digoxigenin tagged LNA probe (Exiqon). After the in situ hybridization, we used the Benchmark LT automated system from Ventana Medical Systems according to the manufacturer's specifications to do the immunohistochemistry for CD9 (1:200, antigen retrieval for 30 min), TLR7 (1:250, antigen retrieval for 30 min), and IL-6 antibodies (1:300, antigen retrieval for 30 min) The data was then analyzed with the Nuance system (Cambridge Research Institutes) which separates the colorimetric based signal for the different chromogens, converts these to fluorescence-based signals, then mixes them using a computer-based analysis system.

Animals

WT B6 mice, B6 TLR7$^{-/-}$ mice, and nude mice were purchased from Jackson Laboratories. Seven WT B6 mice and seven TLR7$^{-/-}$ B6 mice matched for age and sex (7 wk-old males) were injected with $1.8 \times 10^6$ LLC cells in the tail vein and were followed for survival. Necropsy was performed at the moment of death or when the surviving mice were killed 36 d after injection, and multiplicities of lung metastases were photographed and counted.

The in vivo experiment with LLC cells transfected with anti-miRNAs was conducted in six 7-wk-old male B6 mice per group (total n=18). "LNA anti-scrambled" refers to mice injected with LLC cells transfected with LNA anti-scrambled used as control; "LNA anti-miR-16" refers to mice injected with LLC cells transfected with LNA anti-miR-16; "LNA anti-miR-21/29a" refers to mice injected with LLC cells transfected with LNA anti-miR-21 and LNA anti-miR-29a. Mice were injected with $1.8 \times 10^6$ LLC cells in the tail vein and were killed 15 d later. Necropsy was performed, and lung multiplicities were photographed and counted.

The in vivo rescue experiment with LLC cells was conducted in 15 male, 7-wk-old B6 mice. Mice were injected with $1.8 \times 10^6$ LLC cells in the tail vein in 300 μL of volume ($T_0$). After 4 d ($T_4$), i.p. injections were started for 10 mice with GW4869 (1.25 mgkg$^{-1}$d$^{-1}$), an inhibitor of exosome secretion also able to reduce the content of miRNAs in secreted exosomes, and of five mice with DMSO (a solvent of GW4869) as a control, daily for 5 d consecutively. One week after the first injection of GW4869 ($T_{11}$), the tails of five of the GW4869-treated mice were injected with 1 mL of exosomes purified from WT LLC supernatant. The same mice received a second injection of LLC-derived exosomes 3 d later ($T_{14}$). All mice were killed at $T_{18}$, necropsy was performed, and lung multiplicities were counted.

LLC cells transfected with the above-mentioned anti-miRNAs also were injected s.c. into the left flanks of nine nude mice ($8 \times 10^6$ cells per mouse, three mice per condition), and tumor growth was monitored for the following 3 wk. Tumor size was assessed once a week using a digital caliper. Tumor volumes were determined by measuring the length (l) and the width (w) of the tumor and calculating the volume ($V=lw^2/2$).

All procedures used in this study complied with federal guidelines and institutional policies of the Ohio State University Animal Care and Use Committee.

Isolation of Primary Human and Murine Cells.

Total splenocytes derived from WT and TLR7$^{-/-}$ age- and sex-matched mice were prepared by harvesting the spleen and preparing a single-cell suspension. Red blood cells were eliminated by osmotic lysis using red blood cell lysis buffer (eBioscience). Total splenocytes were seeded in a 96-well plate (1×10$^6$ cells in 200 μL of medium per well) and then were stimulated with synthetic miRNAs or with purified exosomes for 18 h. Cells were stained with phycoerythrin-conjugated anti-CD69 (BioLegend) antibody and analyzed using FACSCalibur flow cytometer (Becton Dickinson).

Macrophages derived from the peritoneal cavity were isolated from WT and TLR7$^{-/-}$ age- and sex-matched mice.

PBMC were isolated from heparinized blood of healthy donors by Ficoll-Paque (Pharmacia) centrifugation (500×g) following the manufacturer's instructions and were plated immediately for stimulation. Human PBMCs or murine peritoneal macrophages (300,000 cells) were stimulated with synthetic miRNAs for 24 h; then ELISAs for TNF-α and IL-6 were performed on the conditioned media using Multi-Analyte ELISArray Kits (SABiosciences) following the manufacturer's instructions.

Growth Curve, Cell Viability and Cell Cycle.

For the determination of the growth curve, cells were seeded at a density of 10,000 cells/ml in a 48 well plate. After 24, 48, and 72 h cells were collected and counted with a haemocytometer (Beckman Coulter). Cell viability was examined with 3-(4,5-dimethylthiazol-2-yl)-2,5-diphenilterazolium bromide (MTS)-Cell Titer 96 Aqueous One Solution Cell Proliferation Assay (Promega) following the manufacturer's instructions. Metabolically active cells were detected by adding 20 μl of MTS to each well. After 1 h of incubation, the plate was analyzed in a Multilabel Counter (Bio-Rad Laboratories). Cell cycle analysis was performed by propidium iodide staining (50 μg/ml in PBS) of cells fixed in methanol followed by flow cytometry analysis (FACScan Becton-Dickinson).

Cell Migration and Invasion.

Cell migration and invasion through a 3D-extracellular matrix was assessed by using transwell migration chamber (Corning). Briefly, for migration, transwells were saturated 1 hr at room temperature with PBS 1% BSA. LNA-transfected cells were seeded in the transwell upper chamber and the incubated at 37° C. for 6 h or 24 h. The lower chamber was filled with serum free medium or serum supplemented with 10% FBS, as indicated. After 24 or 6 h, filters were washed, fixed, and stained with Coomassie Brilliant Blue (Sigma-Aldrich Corp.). Cells that had invaded to the lower surface of the filter were counted under the microscope. For invasion experiments, transwells were coated overnight at 4° C. with 80 μg/ml Matrigel™ (Becton Dickinson) and then saturated 2 h at room temperature with PBS 1% BSA. LNA-transfected cells were then processed as described above and allowed to invade the matrix up to 24 h.

NF-κB Activity Assay.

NF-κB activity was assessed by QUANTI-Blue Assay (Invivogen). HEK-Blue-TLR7 and TLR8 293 cells allow verification of the activation of NF-κB after the stimulation of the respective TLRs. Both these cell lines were obtained by co-transfection of the TLR7 and 8 genes and an optimized secreted embryonic alkaline phosphatase reporter gene (SEAP) under the control of the IFN-α minimal promoter fused to five NF-κB and AP-1-binding sites into HEK-293 cells. Stimulation with a TLR7 or 8 ligand activates NF-κB and AP-1, which induces the production of SEAP. Levels of SEAP can be easily determined with QUANTI-Blue, a detection medium that turns purple/blue in the presence of alkaline phosphatase. Supernatants derived from treated TLR7-HEK-293 and TLR8-HEK-293 cells were harvested at 14,000 g for 15 min to eliminate debris; 20 μl were then transferred into a 96-well plate and added to 180 μl of QUANTI-Blue solution (Invivogen). The plate was then incubated at 37° C. for 1-3 h and SEAP levels were determined by reading the plate with a spectrophotometer at 620-655 nm (SpectraMax, Molecular Devices).

Statistical Analysis of Data.

Statistical data are presented as mean±SD unless otherwise specified. Significance was calculated by Student's t test or by ANOVA test with Bonferroni correction. Kaplan-Meier survival curves were calculated with the log-rank (Mantel-Cox) method using the SPSS statistics software (IBM).

For the LNA-ISH analysis, mean and SD were calculated by using InStat software, and significance was determined by Student's t test via InStat.

While the invention has been described with reference to various embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

What is claimed is:

1. A method to inhibit metastasis of at least one cancer cell in a subject having lung cancer, comprising decreasing the levels of expressions of miR-21 and/or miR-29a in exosomes from the lung cancer cell,
    wherein expression level of miR-21 and/or miR-29a is decreased via administration of at least one exosome inhibitor selected from the group consisting of: an antisense miR-21 exosome inhibitor, and an antisense miR-29a exosome inhibitor; and,
    wherein the at least one exosome inhibitor is administered in an amount sufficient to inhibit metastasis of the at least one cancer cell in the subject.

2. A method to inhibit tumor growth of at least one lung cancer tumor, comprising decreasing the levels of miR-21 and/or miR-29a expression in exosomes from cell of the lung cancer,
    wherein expression levels of miR-21 and/or miR-29a is decreased via administration of at least one exosome inhibitor selected from the group consisting of: an antisense miR-21 exosome inhibitor, and an antisense miR-29a exosome inhibitor; and, wherein the at least one exosome inhibitor is administered in an amount sufficient to inhibit tumor growth of the lung cancer in the subject.

3. The method of claim 1, wherein the lung cancer is selected from the group consisting of: Lewis lung carcinoma; squamous cell carcinoma; non-small cell lung carcinoma; and, small cell lung carcinoma.

4. The method of claim 1, where in the antisense miR-21 exosome inhibitor comprises a locked nucleic acid anti-miR-21 exosome inhibitor.

5. The method of claim 1, wherein the antisense miR-29a exosome inhibitor comprises a locked nucleic acid anti-miR-29a exosome inhibitor.

6. The method of claim 1, wherein the antisense miR-21 exosome inhibitor comprises an antisense miR-21 having a modification in a GU motif in the nucleotide region 18-21 of miR-21 sequence.

7. The method of claim 6, wherein the modification in the GU motifs comprises substituting one or more bases at base numbers 18 and 20 in the miR-21 sequence.

8. The method of claim 6, wherein the modification comprises GUUG.

9. The method of claim 1, wherein the antisense miR-29a exosome inhibitor comprises an antisense miR-29a having a modification in a GU motif in the nucleotide region 18-21 of miR-29a sequence.

10. The method of claim 9, wherein the modification in the GU motifs comprises substituting one or more bases at base numbers 20 and 21 in the miR-21 sequence.

11. The method of claim 9, wherein the modification comprises GGUU.

12. The method of claim 2, wherein the lung cancer is selected from the group consisting of: Lewis lung carcinoma; squamous cell carcinoma; non-small cell lung carcinoma; and, small cell lung carcinoma.

13. The method of claim 2, where in the antisense miR-21 exosome inhibitor comprises a locked nucleic acid anti-miR-21 exosome inhibitor.

14. The method of claim 2, wherein the antisense miR-29a exosome inhibitor comprises a locked nucleic acid anti-miR-29a exosome inhibitor.

15. The method of claim 2, wherein the antisense miR-21 exosome inhibitor comprises an antisense miR-21 having a modification in a GU motif in the nucleotide region 18-21 of miR-21 sequence.

16. The method of claim 15, wherein the modification in the GU motifs comprises substituting one or more bases at base numbers 18 and 20 in the miR-21 sequence.

17. The method of claim 15, wherein the modification comprises GUUG.

18. The method of claim 2, wherein the antisense miR-29a exosome inhibitor comprises an antisense miR-29a having a modification in a GU motif in the nucleotide region 18-21 of miR-29a sequence.

19. The method of claim 18, wherein the modification in the GU motifs comprises substituting one or more bases at base numbers 20 and 21 in the miR-21 sequence.

20. The method of claim 18, wherein the modification comprises GGUU.

* * * * *